(12) United States Patent
Aaronson et al.

(10) Patent No.: US 8,691,580 B2
(45) Date of Patent: Apr. 8, 2014

(54) SINGLE CHEMICAL ENTITIES AND METHODS FOR DELIVERY OF OLIGONUCLEOTIDES

(75) Inventors: Jeffrey G. Aaronson, Philadelphia, PA (US); Stanley F. Barnett, North Wales, PA (US); René Bartz, Lawrenceville, NJ (US); Steven L. Colletti, Princeton Junction, NJ (US); Vasant R. Jadhav, Harleysville, PA (US); Aaron A. Momose, Blue Bell, PA (US); Anthony W. Shaw, Harleysville, PA (US); David M. Tellers, Lansdale, PA (US); Thomas J. Tucker, North Wales, PA (US); Weimin Wang, Churchville, PA (US); Yu Yuan, Orlando, FL (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/639,952

(22) PCT Filed: Apr. 4, 2011

(86) PCT No.: PCT/US2011/031080
§ 371 (c)(1),
(2), (4) Date: Oct. 8, 2012

(87) PCT Pub. No.: WO2011/126974
PCT Pub. Date: Oct. 13, 2011

(65) Prior Publication Data
US 2013/0041133 A1 Feb. 14, 2013

Related U.S. Application Data

(60) Provisional application No. 61/322,422, filed on Apr. 9, 2010.

(51) Int. Cl.
*C07H 21/02* (2006.01)

(52) U.S. Cl.
USPC ............ 435/455; 424/78.08; 514/23; 514/54; 514/75; 514/79

(58) Field of Classification Search
None
See application file for complete search history.

(56) References Cited

U.S. PATENT DOCUMENTS

| | | | |
|---|---|---|---|
| 2003/0166512 A1 | 9/2003 | Xie | |
| 2003/0216296 A1 | 11/2003 | Park et al. | |
| 2004/0204377 A1 | 10/2004 | Rana | |
| 2005/0153337 A1 * | 7/2005 | Manoharan | 435/6 |
| 2005/0260756 A1 | 11/2005 | Troy et al. | |
| 2007/0027097 A1 * | 2/2007 | Lewis | 514/44 |
| 2008/0085869 A1 | 4/2008 | Yamada et al. | |
| 2009/0186802 A1 * | 7/2009 | Alluis et al. | 514/2 |
| 2009/0264636 A1 | 10/2009 | Vargeese et al. | |

FOREIGN PATENT DOCUMENTS

| | | | | |
|---|---|---|---|---|
| WO | WO 9964460 A1 * | 12/1999 | | C07K 16/00 |
| WO | 2009126933 | 10/2009 | | |
| WO | WO 2010021718 A1 * | 2/2010 | | A61K 47/48 |

OTHER PUBLICATIONS

Deshayes, S. et al; "Cell penetrating peptides: tools for intracellular delivery of therapeutics." Cell. Mol. Life Sci. (2005) 62 p. 1839-1849.*

Turner et al., "RNA targeting with peptide conjugates of oligonucleotides, siRNA and PNA"; Blood Cells Mol. Dis., vol. 38, No. 1, pp. 1-7, (2007).

* cited by examiner

*Primary Examiner* — Cecilia J Tsang
*Assistant Examiner* — Fred Reynolds
(74) *Attorney, Agent, or Firm* — Yong Zhao; Laura Ginkel

(57) ABSTRACT

In an embodiment the instant invention discloses a modular composition comprising 1) an oligonucleotide; 2) one or more linkers, which may be the same or different, selected from Table 1, wherein the linkers are attached to the oligonucleotide at any 3' and/or 5' end; 3) one or more peptides, which may be the same or different, selected from SEQ ID NOs: 1-59, wherein the peptides are attached to the linkers; and optionally one or more lipids, solubilizing groups and/or targeting ligands attached to the oligonucleotide.

6 Claims, 8 Drawing Sheets

US 8,691,580 B2

SINGLE CHEMICAL ENTITIES AND METHODS FOR DELIVERY OF OLIGONUCLEOTIDES

REFERENCE TO SEQUENCE LISTING SUBMITTED ELECTRONICALLY

The sequence listing of the present application is being submitted electronically via EFS-Web as an ASCII formatted sequence listing with a file name "MRLMIS00023USPCT-SEQTXT-05OCT2012.txt", creation date of Oct. 5, 2012 and a size of 19,787 bytes. This sequence listing submitted via EFS-Web is part of the specification and is herein incorporated by reference in its entirety.

BACKGROUND OF THE INVENTION

Scientific efforts focused on the delivery of oligonucleotides systemically for therapeutic purposes are ongoing. Three highlighted approaches to oligonucleotide delivery include 1) lipid nanoparticle (LNP) encapsulation, 2) polymer conjugation and 3) single chemical conjugation. Single chemical conjugation typically employs a targeting ligand or a lipid or a solubilizing group or an endosomolytic peptide or a cell penetrating peptide and/or a combination of two or all four attached to an oligonucleotide. Linkers may be present in the conjugate as well as other functionalities. Single chemical conjugates are known and attachment of the oligonucleotide occurs either at the 5'- or 3'-end of the oligonucleotide, at both ends, or internally. See WO2005/041859; WO2008/036825 and WO2009/126933.

The single chemical conjugates of the instant invention must contain a peptide, which may be considered an endosomolytic component, cell penetrating peptide and/or a fusigenic peptide, at the 5'- and/or 3'-end of the oligonucleotide. Linkers must be present between the peptide and the oligonucleotide as well. Other functionalities, such as targeting ligands, solubilizing agents, lipids, and/or masking agents are optionally present. Typically the oligonucleotide is an siRNA. Further the oligonucleotide is the passenger strand or the guide strand of the siRNA.

SUMMARY OF THE INVENTION

In an embodiment the instant invention discloses a modular composition comprising 1) an oligonucleotide; 2) one or more linkers, which may be the same or different, selected from Table 1, wherein the linkers are attached to the oligonucleotide at any 3' and/or 5' end; 3) one or more peptides, which may be the same or different, selected from SEQ ID NOs: 1-59, wherein the peptides are attached to the linkers; and optionally one or more lipids, solubilizing groups and/or targeting ligands attached to the oligonucleotide.

In another embodiment the instant invention discloses a modular composition comprising 1) an oligonucleotide; 2) one or more linkers, which may be the same or different, selected from Table 1, wherein the linkers are attached to the oligonucleotide at any 3' and/or 5' end; and 3) one or more peptides, which may be the same or different, selected from SEQ ID NOs: 1-59, wherein the peptides are attached to the linkers.

In another embodiment the instant invention discloses a modular composition comprising 1) an siRNA; 2) one or more linkers, which may be the same or different, selected from Table 1, wherein the linkers are attached to the siRNA at any 3' and/or 5' end; and 3) one or more peptides, which may be the same or different, selected from SEQ ID NOs: 1-59, wherein the peptides are attached to the linkers.

In an embodiment the instant invention discloses a modular composition comprising 1) an siRNA; 2) one or more linkers, which may be the same or different, selected from Table 1, wherein the linkers are attached to the guide strand of the siRNA at the 3' and/or 5' end; 3) one or more peptides, which may be the same or different, selected from SEQ ID NOs: 1-59, wherein the peptides are attached to the linkers.

In an embodiment the instant invention discloses a modular composition comprising 1) an siRNA; 2) one or more linkers, which may be the same or different, selected from Table 1, wherein the linkers are attached to the passenger strand of the siRNA at the 3' and/or 5' end; 3) one or more peptides, which may be the same or different, selected from SEQ ID NOs: 1-59, wherein the peptides are attached to the linkers.

In an embodiment the instant invention discloses a modular composition comprising 1) an oligonucleotide; 2) one or more linkers, which may be the same or different, selected from Table 2, wherein the linkers are attached to the oligonucleotide at any 3' and/or 5' end; 3) one or more peptides, which may be the same or different, selected from SEQ ID NOs: 1-59, wherein the peptides are attached to the linkers; and optionally one or more lipids, solubilizing groups and/or targeting ligands attached to the oligonucleotide.

In another embodiment the instant invention discloses a modular composition comprising 1) an oligonucleotide; 2) one or more linkers, which may be the same or different, selected from Table 2, wherein the linkers are attached to the oligonucleotide at any 3' and/or 5' end; and 3) one or more peptides, which may be the same or different, selected from SEQ ID NOs: 1-59, wherein the peptides are attached to the linkers.

In another embodiment the instant invention discloses a modular composition comprising 1) an siRNA; 2) one or more linkers, which may be the same or different, selected from Table 2, wherein the linkers are attached to the siRNA at any 3' and/or 5' end; and 3) one or more peptides, which may be the same or different, selected from SEQ ID NOs: 1-59, wherein the peptides are attached to the linkers.

In an embodiment the instant invention discloses a modular composition comprising 1) an siRNA; 2) one or more linkers, which may be the same or different, selected from Table 2, wherein the linkers are attached to the guide strand of the siRNA at the 3' and/or 5' end; 3) one or more peptides, which may be the same or different, selected from SEQ ID NOs: 1-59, wherein the peptides are attached to the linkers.

In an embodiment the instant invention discloses a modular composition comprising 1) an siRNA; 2) one or more linkers, which may be the same or different, selected from Table 2, wherein the linkers are attached to the passenger strand of the siRNA at the 3' and/or 5' end; 3) one or more peptides, which may be the same or different, selected from SEQ ID NOs: 1-59, wherein the peptides are attached to the linkers.

In an embodiment the instant invention discloses a modular composition comprising 1) an oligonucleotide; 2) one or more linkers, which may be the same or different, selected from Table 1, wherein the linkers are attached to the oligonucleotide at any 3' and/or 5' end; 3) one or more peptides, which may be the same or different, selected from SEQ ID NOs: 28, 29, 33, 36, 40, 50, 51, 52, 53, 54, 55, 56, 57, 58 and 59, wherein the peptides are attached to the linkers; and optionally one or more lipids, solubilizing groups and/or targeting ligands attached to the oligonucleotide.

In another embodiment the instant invention discloses a modular composition comprising 1) an oligonucleotide; 2) one or more linkers, which may be the same or different, selected from Table 1, wherein the linkers are attached to the oligonucleotide at any 3' and/or 5' end; and 3) one or more peptides, which may be the same or different, selected from SEQ ID NOs: 28, 29, 33, 36, 40, 50, 51, 52, 53, 54, 55, 56, 57, 58 and 59, wherein the peptides are attached to the linkers.

In another embodiment the instant invention discloses a modular composition comprising 1) an siRNA; 2) one or more linkers, which may be the same or different, selected from Table 1, wherein the linkers are attached to the siRNA at any 3' and/or 5' end; and 3) one or more peptides, which may be the same or different, selected from SEQ ID NOs: 28, 29, 33, 36, 40, 50, 51, 52, 53, 54, 55, 56, 57, 58 and 59, wherein the peptides are attached to the linkers.

In an embodiment the instant invention discloses a modular composition comprising 1) an siRNA; 2) one or more linkers, which may be the same or different, selected from Table 1, wherein the linkers are attached to the guide strand of the siRNA at the 3' and/or 5' end; 3) one or more peptides selected from SEQ ID NOs: 28, 29, 33, 36, 40, 50, 51, 52, 53, 54, 55, 56, 57, 58 and 59, wherein the peptides are attached to the linkers.

In an embodiment the instant invention discloses a modular composition comprising 1) an siRNA; 2) one or more linkers, which may be the same or different, selected from Table 1, wherein the linkers are attached to the passenger strand of the siRNA at the 3' and/or 5' end; 3) one or more peptides, which may be the same or different, selected from SEQ ID NOs: 28, 29, 33, 36, 40, 50, 51, 52, 53, 54, 55, 56, 57, 58 and 59, wherein the peptides are attached to the linkers.

In an embodiment the instant invention discloses a modular composition comprising 1) an oligonucleotide; 2) one or more linkers, which may be the same or different, selected from Table 2, wherein the linkers are attached to the oligonucleotide at any 3' and/or 5' end; 3) one or more peptides, which may be the same or different, selected from SEQ ID NOs: 28, 29, 33, 36, 40, 50, 51, 52, 53, 54, 55, 56, 57, 58 and 59, wherein the peptides are attached to the linkers; and optionally one or more lipids, solubilizing groups and/or targeting ligands attached to the oligonucleotide.

In another embodiment the instant invention discloses a modular composition comprising 1) an oligonucleotide; 2) one or more linkers, which may be the same or different, selected from Table 2, wherein the linkers are attached to the oligonucleotide at any 3' and/or 5' end; and 3) one or more peptides, which may be the same or different, selected from SEQ ID NOs: 28, 29, 33, 36, 40, 50, 51, 52, 53, 54, 55, 56, 57, 58 and 59, wherein the peptides are attached to the linkers.

In another embodiment the instant invention discloses a modular composition comprising 1) an siRNA; 2) one or more linkers, which may be the same or different, selected from Table 2, wherein the linkers are attached to the siRNA at any 3' and/or 5' end; and 3) one or more peptides, which may be the same or different, selected from SEQ ID NOs: 28, 29, 33, 36, 40, 50, 51, 52, 53, 54, 55, 56, 57, 58 and 59, wherein the peptides are attached to the linkers.

In an embodiment the instant invention discloses a modular composition comprising 1) an siRNA; 2) one or more linkers, which may be the same or different, selected from Table 2, wherein the linkers are attached to the guide strand of the siRNA at the 3' and/or 5' end; 3) one or more peptides, which may be the same or different, selected from SEQ ID NOs: 28, 29, 33, 36, 40, 50, 51, 52, 53, 54, 55, 56, 57, 58 and 59, wherein the peptides are attached to the linkers.

In an embodiment the instant invention discloses a modular composition comprising 1) an siRNA; 2) one or more linkers, which may be the same or different, selected from Table 2, wherein the linkers are attached to the passenger strand of the siRNA at the 3' and/or 5' end; 3) one or more peptides, which may be the same or different, selected from SEQ ID NOs: 28, 29, 33, 36, 40, 50, 51, 52, 53, 54, 55, 56, 57, 58 and 59, wherein the peptides are attached to the linkers.

DETAILED DESCRIPTION OF THE INVENTION

Figure 1:
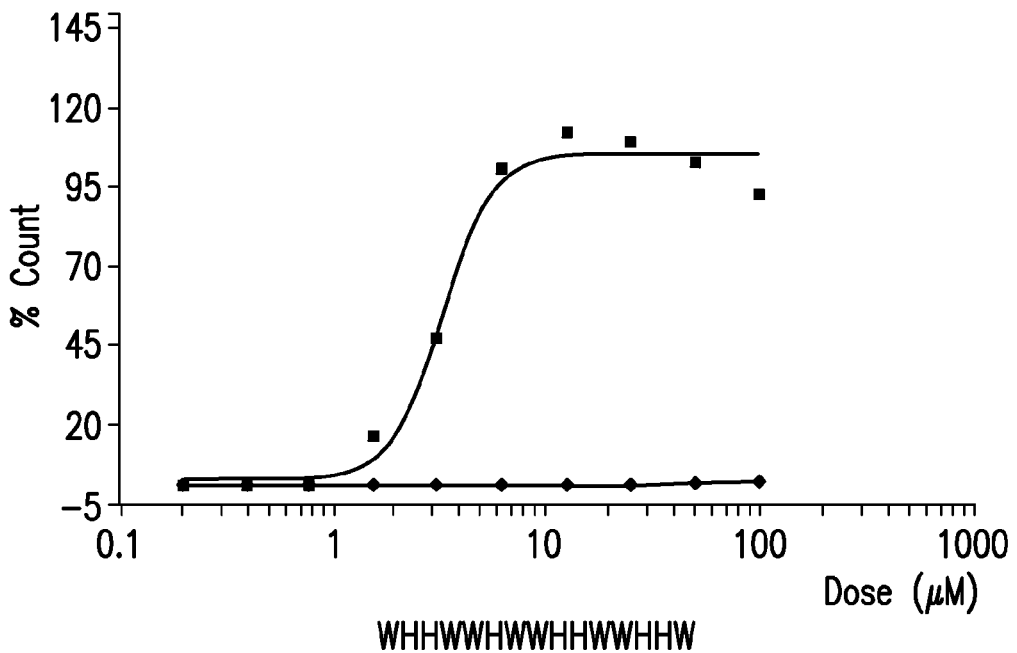
FIG. 1 Percent hemolysis at pH 5.4 and 7.5 for peptide: WHHWWHWWHHWWHHW (SEQ ID NO: 2).

In an embodiment the instant invention discloses a modular composition comprising 1) an oligonucleotide; 2) one or more linkers, which may be the same or different, selected from Table 1, wherein the linkers are attached to the oligonucleotide at any 3' and/or 5' end; 3) one or more peptides, which may be the same or different, selected from SEQ ID NOs: 1-59, wherein the peptides are attached to the linkers; and optionally one or more lipids, solubilizing groups and/or targeting ligands attached to the oligonucleotide.

In another embodiment the instant invention discloses a modular composition comprising 1) an oligonucleotide; 2) one or more linkers, which may be the same or different, selected from Table 1, wherein the linkers are attached to the oligonucleotide at any 3' and/or 5' end; and 3) one or more peptides, which may be the same or different, selected from SEQ ID NOs: 1-59, wherein the peptides are attached to the linkers.

In another embodiment the instant invention discloses a modular composition comprising 1) an siRNA; 2) one or more linkers, which may be the same or different, selected from Table 1, wherein the linkers are attached to the siRNA at any 3' and/or 5' end; and 3) one or more peptides, which may be the same or different, selected from SEQ ID NOs: 1-59, wherein the peptides are attached to the linkers.

In an embodiment the instant invention discloses a modular composition comprising 1) an siRNA; 2) one or more linkers, which may be the same or different, selected from Table 1, wherein the linkers are attached to the guide strand of the siRNA at the 3' and/or 5' end; 3) one or more peptides, which may be the same or different, selected from SEQ ID NOs: 1-59, wherein the peptides are attached to the linkers.

In an embodiment the instant invention discloses a modular composition comprising 1) an siRNA; 2) one or more linkers, which may be the same or different, selected from Table 1, wherein the linkers are attached to the passenger strand of the siRNA at the 3' and/or 5' end; 3) one or more peptides, which may be the same or different, selected from SEQ ID NOs: 1-59, wherein the peptides are attached to the linkers.

In an embodiment the instant invention discloses a modular composition comprising 1) an oligonucleotide; 2) one or more linkers, which may be the same or different, selected from Table 2, wherein the linkers are attached to the oligonucleotide at any 3' and/or 5' end; 3) one or more peptides, which may be the same or different, selected from SEQ ID NOs: 1-59, wherein the peptides are attached to the linkers; and optionally one or more lipids, solubilizing groups and/or targeting ligands attached to the oligonucleotide.

In another embodiment the instant invention discloses a modular composition comprising 1) an oligonucleotide; 2) one or more linkers, which may be the same or different, selected from Table 2, wherein the linkers are attached to the oligonucleotide at any 3' and/or 5' end; and 3) one or more peptides, which may be the same or different, selected from SEQ ID NOs: 1-59, wherein the peptides are attached to the linkers.

In another embodiment the instant invention discloses a modular composition comprising 1) an siRNA; 2) one or more linkers, which may be the same or different, selected from Table 2, wherein the linkers are attached to the siRNA at any 3' and/or 5' end; and 3) one or more peptides, which may be the same or different, selected from SEQ ID NOs: 1-59, wherein the peptides are attached to the linkers.

In an embodiment the instant invention discloses a modular composition comprising 1) an siRNA; 2) one or more linkers, which may be the same or different, selected from Table 2, wherein the linkers are attached to the guide strand of the siRNA at the 3' and/or 5' end; 3) one or more peptides, which may be the same or different, selected from SEQ ID NOs: 1-59, wherein the peptides are attached to the linkers.

In an embodiment the instant invention discloses a modular composition comprising 1) an siRNA; 2) one or more linkers, which may be the same or different, selected from Table 2, wherein the linkers are attached to the passenger strand of the siRNA at the 3' and/or 5' end; 3) one or more peptides, which may be the same or different, selected from SEQ ID NOs: 1-59, wherein the peptides are attached to the linkers.

In an embodiment the instant invention discloses a modular composition comprising 1) an oligonucleotide; 2) one or more linkers, which may be the same or different, selected from Table 1, wherein the linkers are attached to the oligonucleotide at any 3' and/or 5' end; 3) one or more peptides, which may be the same or different, selected from SEQ ID NOs: 28, 29, 33, 36, 40, 50, 51, 52, 53, 54, 55, 56, 57, 58 and 59, wherein the peptides are attached to the linkers; and optionally one or more lipids, solubilizing groups and/or targeting ligands attached to the oligonucleotide.

In another embodiment the instant invention discloses a modular composition comprising 1) an oligonucleotide; 2) one or more linkers, which may be the same or different, selected from Table 1, wherein the linkers are attached to the oligonucleotide at any 3' and/or 5' end; and 3) one or more peptides, which may be the same or different, selected from SEQ ID NOs: 28, 29, 33, 36, 40, 50, 51, 52, 53, 54, 55, 56, 57, 58 and 59, wherein the peptides are attached to the linkers.

In another embodiment the instant invention discloses a modular composition comprising 1) an siRNA; 2) one or more linkers, which may be the same or different, selected from Table 1, wherein the linkers are attached to the siRNA at any 3' and/or 5' end; and 3) one or more peptides, which may be the same or different, selected from SEQ ID NOs: 28, 29, 33, 36, 40, 50, 51, 52, 53, 54, 55, 56, 57, 58 and 59, wherein the peptides are attached to the linkers.

In an embodiment the instant invention discloses a modular composition comprising 1) an siRNA; 2) one or more linkers, which may be the same or different, selected from Table 1, wherein the linkers are attached to the guide strand of the siRNA at the 3' and/or 5' end; 3) one or more peptides selected from SEQ ID NOs: 28, 29, 33, 36, 40, 50, 51, 52, 53, 54, 55, 56, 57, 58 and 59, wherein the peptides are attached to the linkers.

In an embodiment the instant invention discloses a modular composition comprising 1) an siRNA; 2) one or more linkers, which may be the same or different, selected from Table 1, wherein the linkers are attached to the passenger strand of the siRNA at the 3' and/or 5' end; 3) one or more peptides, which may be the same or different, selected from SEQ ID NOs: 28, 29, 33, 36, 40, 50, 51, 52, 53, 54, 55, 56, 57, 58 and 59, wherein the peptides are attached to the linkers.

In an embodiment the instant invention discloses a modular composition comprising 1) an oligonucleotide; 2) one or more linkers, which may be the same or different, selected from Table 2, wherein the linkers are attached to the oligonucleotide at any 3' and/or 5' end; 3) one or more peptides, which may be the same or different, selected from SEQ ID NOs: 28, 29, 33, 36, 40, 50, 51, 52, 53, 54, 55, 56, 57, 58 and 59, wherein the peptides are attached to the linkers; and optionally one or more lipids, solubilizing groups and/or targeting ligands attached to the oligonucleotide.

In another embodiment the instant invention discloses a modular composition comprising 1) an oligonucleotide; 2) one or more linkers, which may be the same or different, selected from Table 2, wherein the linkers are attached to the oligonucleotide at any 3' and/or 5' end; and 3) one or more peptides, which may be the same or different, selected from SEQ ID NOs: 28, 29, 33, 36, 40, 50, 51, 52, 53, 54, 55, 56, 57, 58 and 59, wherein the peptides are attached to the linkers.

In another embodiment the instant invention discloses a modular composition comprising 1) an siRNA; 2) one or more linkers, which may be the same or different, selected from Table 2, wherein the linkers are attached to the siRNA at any 3' and/or 5' end; and 3) one or more peptides, which may be the same or different, selected from SEQ ID NOs: 28, 29, 33, 36, 40, 50, 51, 52, 53, 54, 55, 56, 57, 58 and 59, wherein the peptides are attached to the linkers.

In an embodiment the instant invention discloses a modular composition comprising 1) an siRNA; 2) one or more linkers, which may be the same or different, selected from Table 2, wherein the linkers are attached to the guide strand of the siRNA at the 3' and/or 5' end; 3) one or more peptides, which may be the same or different, selected from SEQ ID NOs: 28, 29, 33, 36, 40, 50, 51, 52, 53, 54, 55, 56, 57, 58 and 59, wherein the peptides are attached to the linkers.

In an embodiment the instant invention discloses a modular composition comprising 1) an siRNA; 2) one or more linkers, which may be the same or different, selected from Table 2, wherein the linkers are attached to the passenger strand of the siRNA at the 3' and/or 5' end; 3) one or more peptides, which may be the same or different, selected from SEQ ID NOs: 28, 29, 33, 36, 40, 50, 51, 52, 53, 54, 55, 56, 57, 58 and 59, wherein the peptides are attached to the linkers.

To illustrate the invention via cartoon, the invention features a modular composition, comprising an oligonucleotide (O), a linker(s) (L), a peptide(s) (P), and an optional lipid(s) (X), targeting ligand(s) (X), and/or solubilizing group(s) (X).

The modular composition may have the formula:

P-L-O-L-P.

The modular composition may have the formula:

P-L-O-X.

The modular composition may have the formula:

P-L-O.

An example of a modular compositions is:

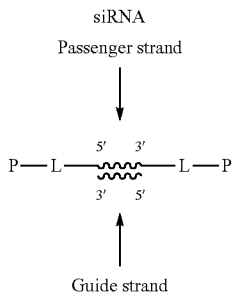

This example is used as guidance. One skilled in the art will recognize that a variety of permutations for placing the desired components on the passenger and guide strand exist.

When the oligonucleotide is a double-stranded oligonucleotide, the "P-L" and the lipid, targeting ligand, and/or solubilizing group may be located on the same strand or on different strands.

In some embodiments, the "P-L" and the lipid, targeting ligand, and/or solubilizing group are on the same strand.

In some embodiments, the "P-L" and the lipid, targeting ligand, and/or solubilizing group are on the passenger strand.

In some embodiments, the "P-L" and the lipid, targeting ligand, and/or solubilizing group are on the guide strand.

In some embodiments, the "P-L" and the lipid, targeting ligand, and/or solubilizing group are located on different strands.

In some embodiments, the "P-L" is on the passenger strand while the lipid, targeting ligand, and/or solubilizing group is on the guide strand.

In some embodiments, the "P-L" and the lipid, targeting ligand, and/or solubilizing group are on different strands but on the same terminal end of the double-stranded oligonucleotide.

In some embodiments, the "P-L" and the lipid, targeting ligand, and/or solubilizing group are on different strands and on the opposite terminal ends of the double-stranded oligonucleotide.

In some embodiments, an additional "P-L" of identical or different nature can be used in place of the lipid, targeting ligand, and/or solubilizing group noted in the above embodiments.

In some embodiments, the "P-L" can be located on multiple terminal ends of either the passenger or guide strand and the lipid, targeting ligand, and/or solubilizing group can be located on the remaining terminal ends of the passenger and guide strands.

In some embodiments, one "P-L" and two or more lipids, targeting ligands, and/or solubilizing groups are present in the oligonucleotide.

In some embodiments, two or more "P-L" and two or more lipids, targeting ligands and/or solubilizing groups are present in the oligonucleotide.

In some embodiments, when the oligonucleotide is a double-stranded oligonucleotide and multiple "P-L" components and/or lipids, targeting ligands, and/or solubilizing groups are present, such multiple "P-L" components and/or lipids, targeting ligands, and/or solubilizing groups may all be present in one strand or both strands of the double stranded oligonucleotide.

When multiple "P-L" components and/or lipids, targeting ligands, and/or solubilizing groups are present, they may all be the same or different.

In another aspect, the invention includes a method of delivering an oligonucleotide to a cell. The method includes (a) providing or obtaining a modular composition of the invention; (b) contacting a cell with the modular composition; and (c) allowing the cell to internalize the modular composition.

The method can be performed in vitro, ex vivo or in vivo, e.g., to treat a subject identified as being in need of an oligonucleotide. A subject in need of said oligonucleotide is a subject, e.g., a human, in need of having the expression of a gene or genes, e.g., a gene related to a disorder, downregulated or silenced.

In one aspect, the invention provides a method for inhibiting the expression of one or more genes. The method comprising contacting one or more cells with an effective amount of an oligonucleotide of the invention, wherein the effective amount is an amount that suppresses the expression of the one or more genes. The method can be performed in vitro, ex vivo or in vivo.

The methods and compositions of the invention, e.g., the modular composition described herein, can be used with any oligonucleotides known in the art. In addition, the methods and compositions of the invention can be used for the treatment of any disease or disorder known in the art, and for the treatment of any subject, e.g., any animal, any mammal, such as any human. One of ordinary skill in the art will also recognize that the methods and compositions of the invention may be used for the treatment of any disease that would benefit from downregulating or silencing a gene or genes.

The methods and compositions of the invention, e.g., the modular composition described herein, may be used with any dosage and/or formulation described herein, or any dosage or formulation known in the art. In addition to the routes of administration described herein, an ordinarily skilled artisan will also appreciate that other routes of administration may be used to administer the modular composition of the invention.

Oligonucleotide

An "oligonucleotide" as used herein, is a double stranded or single stranded, unmodified or modified RNA or DNA. Examples of modified RNAs include those which have greater resistance to nuclease degradation than do unmodified RNAs. Further examples include those which have a 2' sugar modification, a base modification, a modification in a single strand overhang, for example a 3' single strand overhang, or, particularly if single stranded, a 5' modification which includes one or more phosphate groups or one or more analogs of a phosphate group. Examples and a further description of oligonucleotides can be found in WO2009/126933, which is hereby incorporated by reference.

In an embodiment, an oligonucleotide is an antisense, miRNA or siRNA. The preferred oligonucleotide is an siRNA. Another preferred oligonucleotide is the passenger strand of an siRNA. Another preferred oligonucleotide is the guide strand of an siRNA.

siRNA siRNA directs the sequence-specific silencing of mRNA through a process known as RNA interference (RNAi). The process occurs in a wide variety of organisms, including mammals and other vertebrates. Methods for preparing and administering siRNA and their use for specifically inactivating gene function are known. siRNA includes modified and unmodified siRNA. Examples and a further description of siRNA can be found in WO2009/126933, which is hereby incorporated by reference.

A number of exemplary routes of delivery are known that can be used to administer siRNA to a subject. In addition, the siRNA can be formulated according to any exemplary method known in the art. Examples and a further description of siRNA formulation and administration can be found in WO2009/126933, which is hereby incorporated by reference.

Peptides

For macromolecular drugs and hydrophilic drug molecules, which cannot easily cross bilayer membranes, entrapment in endosomal/lysosomal compartments in the cell is thought to be the biggest hurdle for effective delivery to their site of action. Without wishing to be bound by theory, it is believed that the use of peptides will facilitate oligonucleotide escape from these endosomal/lysosomal compartments or oligonucleotide translocation across a cellular membrane and release into the cytosolic compartment. In certain embodiments, the peptides of the present invention may be polycationic or amphiphilic or polyanionic peptides or peptidomimetics which show pH-dependent membrane activity and/or fusogenicity. A peptidomimetic may be a small protein-like chain designed to mimic a peptide.

In some embodiments, the peptide is a cell-permeation agent, preferably a helical cell-permeation agent. These peptides are commonly referred to as Cell Penetrating Peptides. See, for example, "Handbook of Cell Penetrating Peptides" Ed. Langel, U.; 2007, CRC Press, Boca Raton, Fla. Preferably, the component is amphipathic. The helical agent is preferably an alpha-helical agent, which preferably has a lipophilic and a lipophobic phase. A cell-permeation agent can be, for example, a cell permeation peptide, cationic peptide, amphipathic peptide or hydrophobic peptide, e.g. consisting primarily of Tyr, Trp and Phe, dendrimer peptide, constrained peptide or crosslinked peptide. Examples of cell penetrating peptides include Tat, Penetratin, and MPG. For the present invention, it is believed that the cell penetrating peptides can be a "delivery" peptide, which can carry large polar molecules including peptides, oligonucleotides, and proteins across cell membranes. Cell permeation peptides can be linear or cyclic, and include D-amino acids, "retro-inverso" sequences, non-peptide or pseudo-peptide linkages, peptidyl mimics. In addition the peptide and peptide mimics can be modified, e.g. glycosylated, pegylated, or methylated. Examples and a further description of peptides can be found in WO2009/126933, which is hereby incorporated by reference. Synthesis of peptides is will known in the art.

The peptides may be conjugated at either end or both ends by addition of a cysteine or other thiol containing moiety to the C- or N-terminus. When not functionalized on the N-terminus, peptides may be capped by an acetyl group, or may be capped with a lipid, a PEG, or a targeting moiety. When the C-terminus of the peptides is unconjugated or unfunctionalized, it may be capped as an amide, or may be capped with a lipid, a PEG, or a targeting moiety.

The peptides of the instant invention are:

```
HFHHFFHHFFHFFHHFFHHF;            (SEQ ID NO: 1)

WHHWWHWWHHWWHHW;                 (SEQ ID NO: 2)

HWHHLLHHLLHLLHHLLHHL;            (SEQ ID NO: 3)

HLHHWLHHLLHLLHHLLHHL;            (SEQ ID NO: 4)

HLHHLWHHLLHLLHHLLHHL;            (SEQ ID NO: 5)

HLHHLLHHLWHLLHHLLHHL;            (SEQ ID NO: 6)

HLHHLLHHLLHWLHHLLHHL;            (SEQ ID NO: 7)

HLHHLLHHLLHLLHHWLHHL;            (SEQ ID NO: 8)

HLHHLLHHLLHLLHHLWHHL;            (SEQ ID NO: 9)

HPHHLLHHLLHLLHHLLHHL;            (SEQ ID NO: 10)

HLHHPLHHLLHLLHHLLHHL;            (SEQ ID NO: 11)

HLHHLPHHLLHLLHHLLHHL;            (SEQ ID NO: 12)

HLHHLLHHLPHLLHHLLHHL;            (SEQ ID NO: 13)

HLHHLLHHLLHLLHHLPHHL;            (SEQ ID NO: 14)

HLHHLLHHLLHLLHHLLHHP;            (SEQ ID NO: 15)

ELEELLEELLHLLHHLLHHL;            (SEQ ID NO: 16)

ELHHLLHELLHLLHELLHHL;            (SEQ ID NO: 17)

GLWRALWRLLRSLWRLLWRAC;           (SEQ ID NO: 18)

GLFEAIEGFIENGWEGMIDGWYGYGRKKRRQRR;   (SEQ ID NO: 19)

HLHHLLHHLLHLLHHLLHHL;            (SEQ ID NO: 20)

HWHHWWHHWWHWWHHWWHHW;            (SEQ ID NO: 21)

HLHHLLHHWLHLLHHLLHHL;            (SEQ ID NO: 22)

HLHHLLHHLLHLWHHLLHHL;            (SEQ ID NO: 23)

HLHHLLHHLLHLLHHLLHHW;            (SEQ ID NO: 24)

HHHHHHHHHHLLLLLLLLLL;            (SEQ ID NO: 25)

HHHHHHHLLLLLLL;                  (SEQ ID NO: 26)
```

-continued

LTTLLTLLTTLLTTL; (SEQ ID NO: 27)

KLLKLLKLWLKLLKLLLKLL; (SEQ ID NO: 28)

LHLLHHLLHHLHHLLHHLLHLLHHLLHHL; (SEQ ID NO: 29)

FLGGIISFFKRLF; (SEQ ID NO: 30)

FIGGIISFIKKLF; (SEQ ID NO: 31)

FIGGIISLIKKLF; (SEQ ID NO: 32)

HLLHLLLHLWLHLLHLLLHLL; (SEQ ID NO: 33)

GIGGAVLKVLTTGLPALISWIKRKRQQ; (SEQ ID NO: 34)

RQIKIWFQNRRMKWKKGG; (SEQ ID NO: 35)

RKKRRQRRRPPQ; (SEQ ID NO: 36)

GALFLGWLGAAGSTMGAPKKKRKV; (SEQ ID NO: 37)

GGGARKKAAKAARKKAAKAARKKAAKAARKKAAKAAK; (SEQ ID NO: 38)

GWTLNSAGYLLGKINLKALAALAKKIL; (SEQ ID NO: 39)

RRRRRRRRR; (SEQ ID NO: 40)

WEAKLAKALAKALAKHILAKALAKALKACEA; (SEQ ID NO: 41)

WEAALAEALAEALAEHLAEALAEAEALEALAA; (SEQ ID NO: 42)

D(NHC$_{12}$H$_{25}$)NleKNleKNleHNleKNleHNle; (SEQ ID NO: 43)

KLLKLLLKLWLKLLKLLLKLL; (SEQ ID NO: 44)

GLFEAIAGFIENGWEGMIDGWYG; (SEQ ID NO: 45)

GLFHAIAAHFIHGGWHGLIHGWYG; (SEQ ID NO: 46)

GLFEAIAEFIEGGWEGLIEGWYG; (SEQ ID NO: 47)

GLFEAIEGFIENGWEGMIDGWYG; (SEQ ID NO: 48)

GLFKAIAKFIKGGWKGLIKGWYG; (SEQ ID NO: 49)

GLFEAIAGFIENGWEGMIDGWYGYGRKKRRQRR; (SEQ ID NO: 50)

GLFEAIAGFIENGWEGMIDGWYGRQIKIWFQNRRMKWKKGG; (SEQ ID NO: 51)

GLFHAIAAHFIHGGWHGLIHGWYGYGRKKRRQRR; (SEQ ID NO: 52)

GLFEAIAEFIEGGWEGLIEGWYGYGRKKRRQRR; (SEQ ID NO: 53)

GLFEAIEGFIENGWEGMIDGWYGYGRKKRRQRR; (SEQ ID NO: 54)

GLFKAIAKFIKGGWKGLIKGWYGYGRKKRRQRR; (SEQ ID NO: 55)

GFFALIPKIISSPLFKTLLSAVGSALSSSGEQE; (SEQ ID NO: 56)

LHLLHHLLHHLHHLLHHLLHLLHHLLHHLGGGRKKRRQRRRPPQ; (SEQ ID NO: 57)

RKKRRQRRRPPQGGGLHLLHHLLHHLHHLLHHLLHLLHHLLHHL; and (SEQ ID NO: 58)

LIRLWSHIHIWFQWRRLKWKKK; (SEQ ID NO: 59)

wherein the peptides are optionally conjugated at either end by addition of a cysteine or other thiol containing moiety to the C- or N-terminus; or when not functionalized on the N-terminus, the peptides are optionally capped by an acetyl group, lipid, peg or a targeting moiety; or when not functionalized on the C-terminus, the peptides are optionally capped by an amide, lipid, peg or a targeting moiety.

The preferred peptides (P) are:

KLLKLLLKLWLKLLKLLLKLL; (SEQ ID NO: 28)

LHLLHHLLHHLHHLLHHLLHLLHHLLHHL; (SEQ ID NO: 29)

HLLHLLLHLWLHLLHLLLHLL; (SEQ ID NO: 33)

RKKRRQRRRPPQ; (SEQ ID NO: 36)

RQIKIWFQNRRMKWKKGG; (SEQ ID NO: 35)

GLFEAIAGFIENGWEGMIDGWYGYGRKKRRQRR; (SEQ ID NO: 50)

GLFEAIAGFIENGWEGMIDGWYGRQIKIWFQNRRMKWKKGG; (SEQ ID NO: 51)

GLFHAIAAHFIHGGWHGLIHGWYGYGRKKRRQRR; (SEQ ID NO: 52)

GLFEAIAEFIEGGWEGLIEGWYGYGRKKRRQRR; (SEQ ID NO: 53)

GLFEAIEGFIENGWEGMIDGWYGYGRKKRRQRR; (SEQ ID NO: 54)

GLFKAIAKFIKGGWKGLIKGWYGYGRKKRRQRR; (SEQ ID NO: 55)

GFFALIPKIISSPLFKTLLSAVGSALSSSGEQE; (SEQ ID NO: 56)

LHLLHHLLHHLHHLLHHLLHLLHHLLHHLGGGRKKRRQRRRPPQ; (SEQ ID NO: 57)

RKKRRQRRRPPQGGGLHLLHHLLHHLHHLLHHLLHLLHHLLHHL; and (SEQ ID NO: 58)

LIRLWSHIHIWFQWRRLKWKKK; (SEQ ID NO: 59)

wherein the peptides are optionally conjugated at either end by addition of a cysteine or other thiol containing moiety to the C- or N-terminus; or when not functionalized on the N-terminus, the peptides are optionally capped by an acetyl group, lipid, peg or a targeting moiety; or when not functionalized on the C-terminus, the peptides are optionally capped by an amide, lipid, peg or a targeting moiety.

Linkers

The covalent linkages between the peptide and the oligonucleotide of the modular composition of the invention is mediated by a linker. This linker may be cleavable or non-cleavable, depending on the application. In certain embodiments, a cleavable linker may be used to release the oligonucleotide after transport from the endosome to the cytoplasm. The intended nature of the conjugation or coupling interaction, or the desired biological effect, will determine the choice of linker group. Linker groups may be combined or branched to provide more complex architectures. Examples and a further description of linkers can be found in WO2009/126933, which is hereby incorporated by reference.

The linkers of the instant invention are shown in Table 1:

TABLE 1

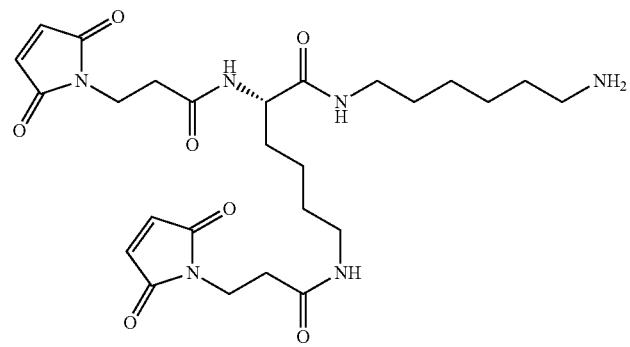 [SMILES: NCCCCCCNC(=O)[C@H](CCCCNC(=O)CCN1C(=O)C=CC1=O)NC(=O)CCN1C(=O)C=CC1=O]

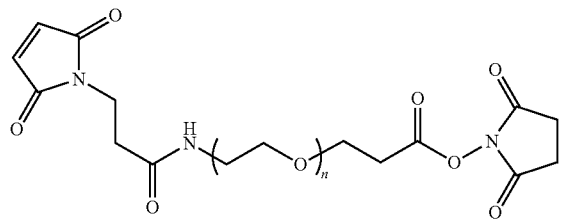

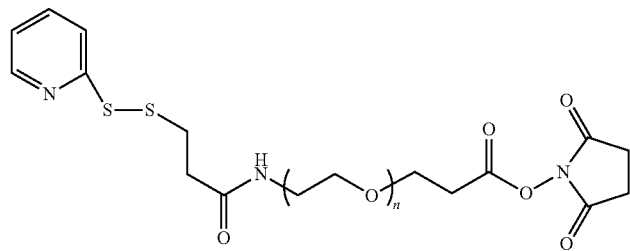

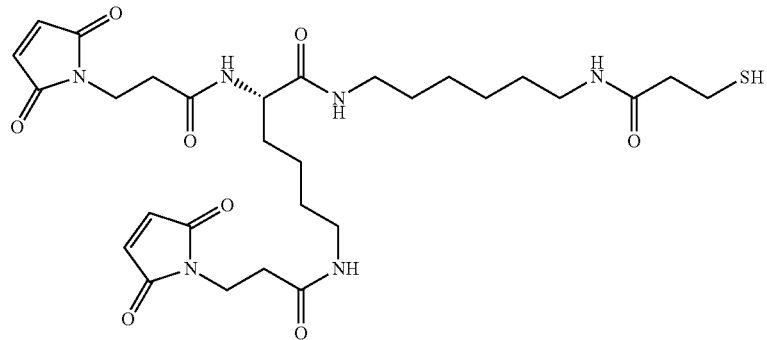 [SMILES: O=C(CCS)NCCCCCCNC(=O)[C@H](CCCCNC(=O)CCN1C(=O)C=CC1=O)NC(=O)CCN1C(=O)C=CC1=O]

TABLE 1-continued
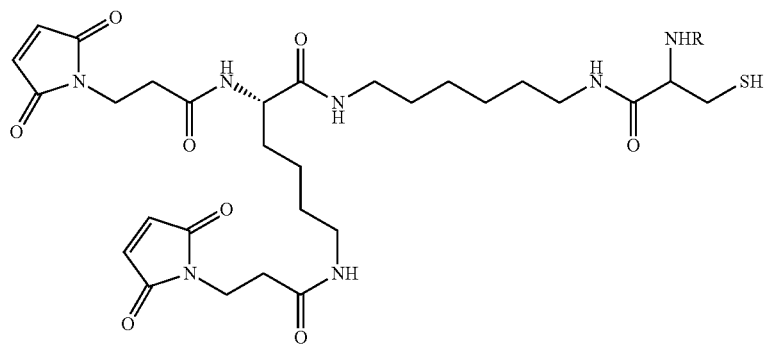
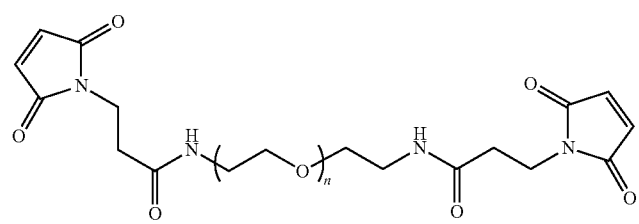
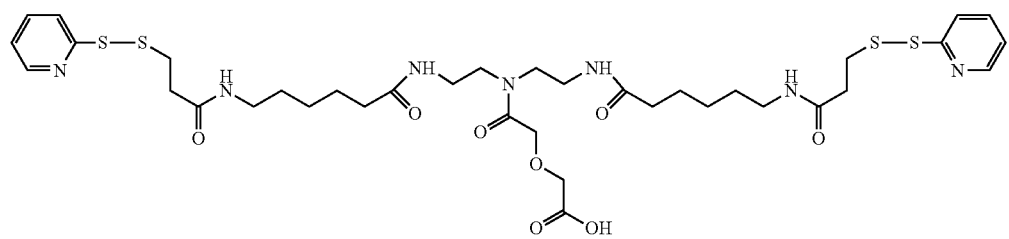 [SMILES: O=C(O)COCC(=O)N(CCNC(=O)CCCCCNC(=O)CCSSc1ccccn1)CCNC(=O)CCCCCNC(=O)CCSSc1ccccn1]
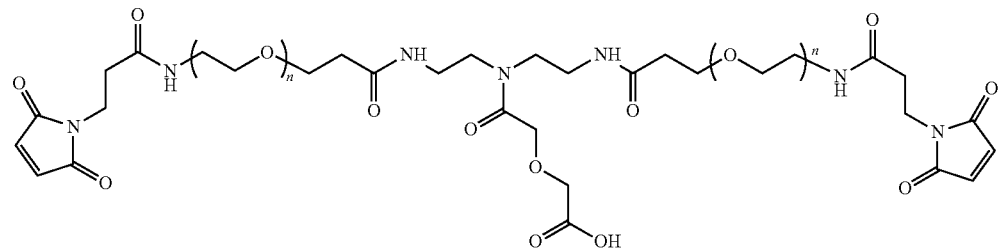
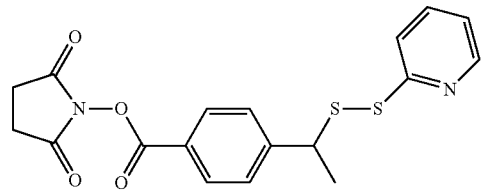
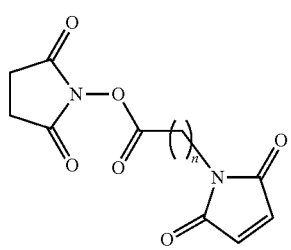
R = H, Boc, Cbz, Ac, PEG, lipid, targeting ligand, linker(s) and/or peptide(s).
n = 0 to 750.

The preferred linkers are shown in Table 2:

TABLE 2

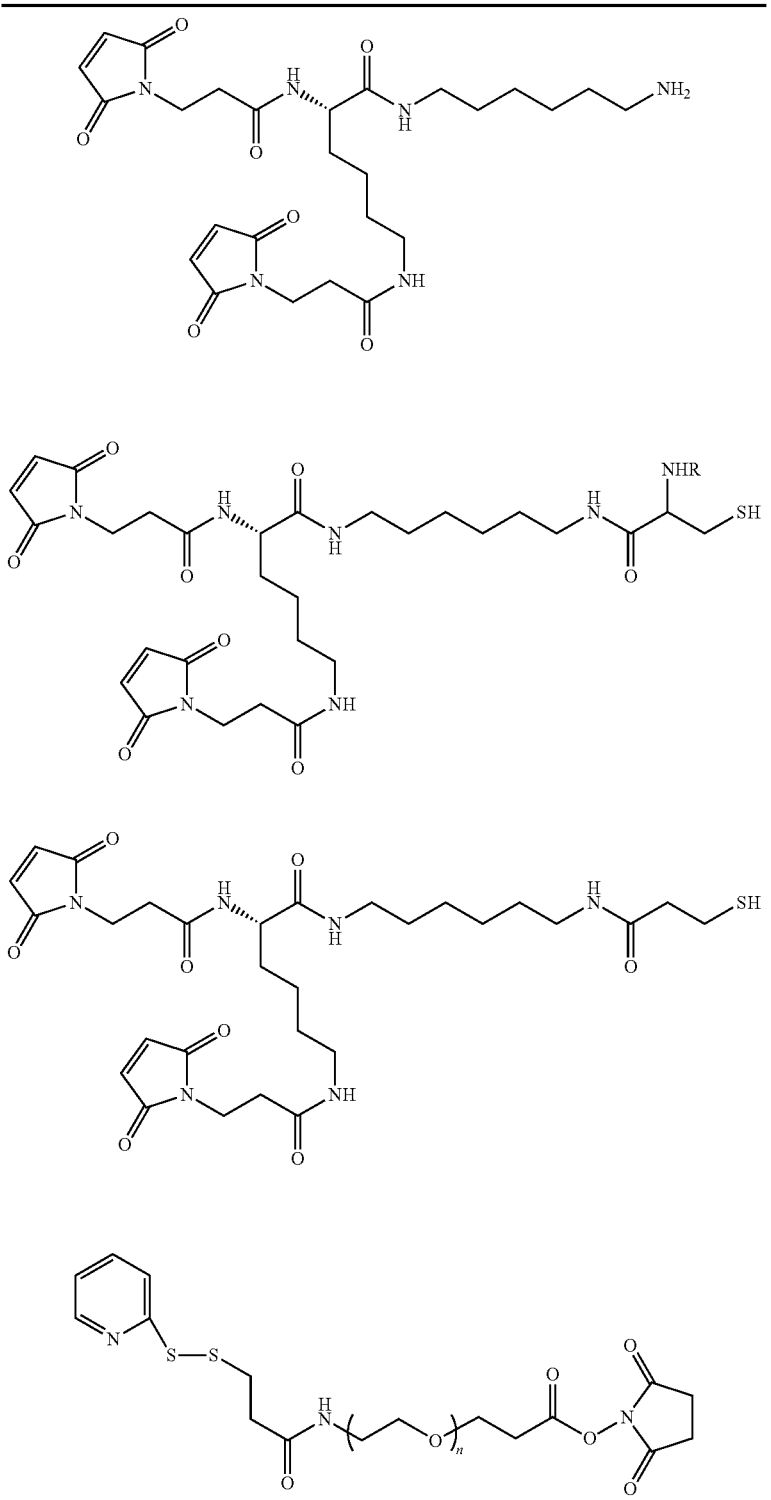

R = H, Boc, Cbz, Ac, PEG, lipid, targeting ligand, linker(s) and/or peptide(s).
n = 0 to 750.

Commercial linkers are available from various suppliers such as Pierce or Quanta Biodesign including combinations of said linkers. The linkers may also be combined to produce more complex branched architectures accommodating from 1 to 8 peptides as illustrated in one such example below:

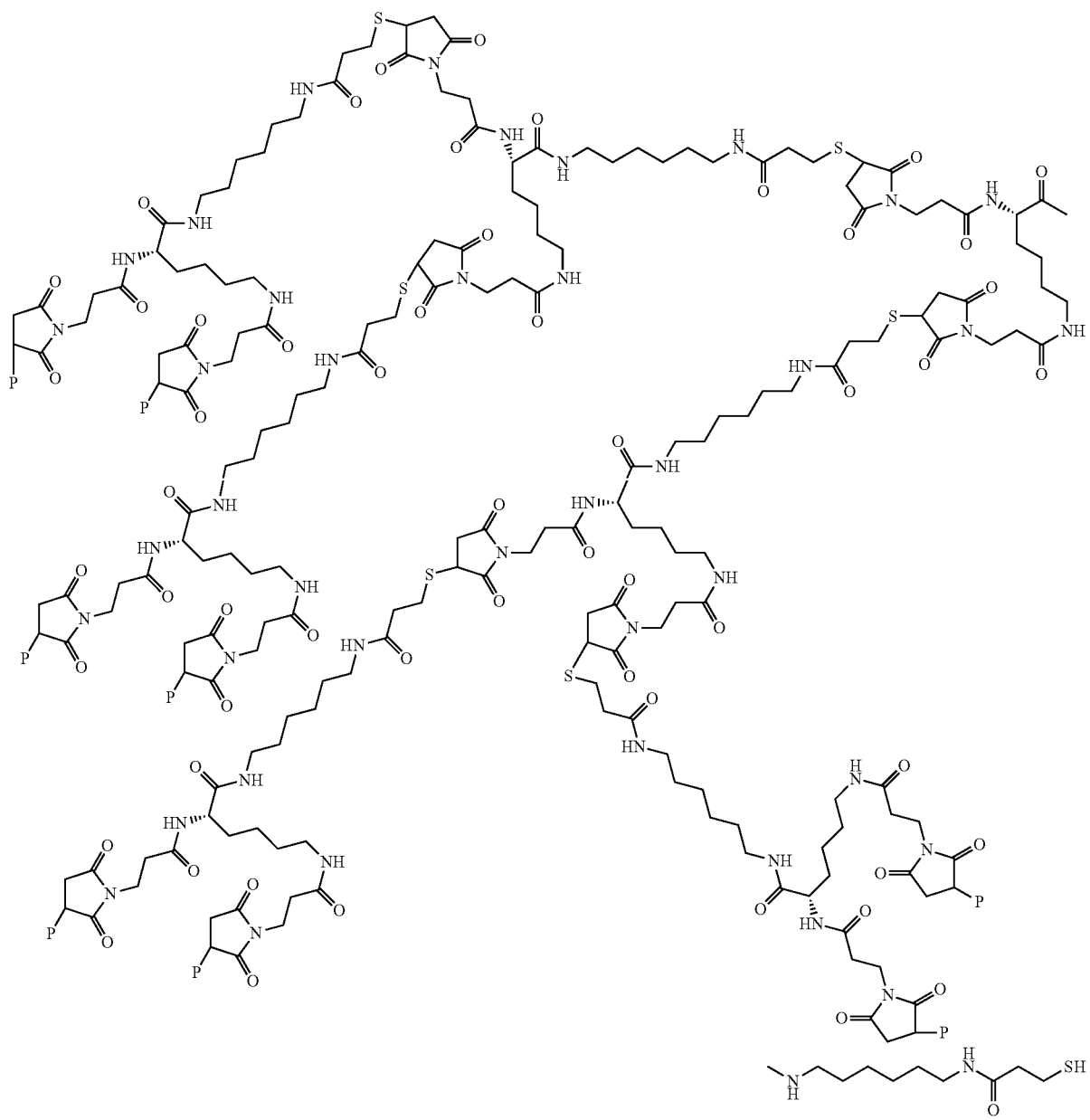

Targeting Ligands

The modular compositions of the present invention may comprise a targeting ligand. In some embodiments, this targeting ligand may direct the modular composition to a particular cell. For example, the targeting ligand may specifically or non-specifically bind with a molecule on the surface of a target cell. The targeting moiety can be a molecule with a specific affinity for a target cell. Targeting moieties can include antibodies directed against a protein found on the surface of a target cell, or the ligand or a receptor-binding portion of a ligand for a molecule found on the surface of a target cell. Examples and a further description of targeting ligands can be found in WO2009/126933, which is hereby incorporated by reference.

The targeting ligands are selected from the group consisting of an antibody, a ligand-binding portion of a receptor, a ligand for a receptor, an aptamer, D-galactose, N-acetyl-D-galactose (GalNAc), multivalent N-acytyl-D-galactose, D-mannose, cholesterol, a fatty acid, a lipoprotein, folate, thyrotropin, melanotropin, surfactant protein A, mucin, carbohydrate, multivalent lactose, multivalent galactose, N-acetyl-galactosamine, N-acetyl-glucosamine, multivalent mannose, multivalent fructose, glycosylated polyaminoacids, transferin, bisphosphonate, polyglutamate, polyaspartate, a lipophilic moiety that enhances plasma protein binding, a steroid, bile acid, vitamin B12, biotin, an RGD peptide, an RGD peptide mimic, ibuprofen, naproxen, aspirin, folate, and analogs and derivatives thereof.

The preferred targeting ligands are selected from the group consisting of D-galactose, N-acetyl-D-galactose (GalNAc), GalNAc2, and GalNAc3, cholesterol, folate, and analogs and derivatives thereof.

Lipids

Lipophilic moieties, such as cholesterol or fatty acids, when attached to highly hydrophilic molecules such as nucleic acids can substantially enhance plasma protein binding and consequently circulation half life. In addition, lipophilic groups can increase cellular uptake. For example, lipids can bind to certain plasma proteins, such as lipoproteins, which have consequently been shown to increase uptake in specific tissues expressing the corresponding lipoprotein receptors (e.g., LDL-receptor or the scavenger receptor SR-B 1). Lipophilic conjugates can also be considered as a targeted delivery approach and their intracellular trafficking could potentially be further improved by the combination with endosomolytic agents.

Exemplary lipophilic moieties that enhance plasma protein binding include, but are not limited to, sterols, cholesterol, fatty acids, cholic acid, lithocholic acid, dialkylglycerides, diacylglyceride, phospholipids, sphingolipids, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, phenoxazine, aspirin, naproxen, ibuprofen, vitamin E and biotin etc. Examples and a further description of lipids can be found in WO2009/126933, which is hereby incorporated by reference.

The preferred lipid is cholesterol.

Solubilizing Agents

The modular composition may comprise one or more other moieties/ligands that may enhance aqueous solubility, circulation half life and/or cellular uptake. These can include naturally occurring substances, such as a protein (e.g., human serum albumin (HSA), low-density lipoprotein (LDL), high-density lipoprotein (HDL), or globulin); or a carbohydrate (e.g., a dextran, pullulan, chitin, chitosan, inulin, cyclodextrin or hyaluronic acid). These moieties may also be a recombinant or synthetic molecule, such as a synthetic polymer or synthetic polyamino acids. Examples include polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG, e.g., PEG-0.5K, PEG-2K, PEG-5K, PEG-10K, PEG-12K, PEG-15K, PEG-20K, PEG-40K), methyl-PEG (mPEG), [mPEG]2, polyvinyl alcohol (PVA), polyurethane, poly(2 ethylacryllic acid), N-isopropylacrylamide polymers, or polyphosphazine. Examples and a further description of solubilizing agents can be found in WO2009/126933, which is hereby incorporated by reference.

The preferred solubilizing group is PEG 0.5K to 30K.

Method of Treatment

In one aspect, the invention features, a method of treating a subject at risk for or afflicted with a disease that may benefit from the administration of the modular composition of the invention. The method comprises administering the modular composition of the invention to a subject in need thereof, thereby treating the subject. The oligonucleotide that is administered will depend on the disease being treated. See WO2009/126933 for additional details regarding methods of treatments for specific indications.

Formulation

There are numerous methods for preparing conjugates of oligonucleotide compounds. The techniques should be familiar to those skilled in the art. A useful reference for such reactions is Bioconjugate Techniques, Hermanson, G. T., Academic Press, San Diego, Calif., 1996. Other references include WO2005/041859; WO2008/036825 and WO2009/126933.

EXAMPLES

The invention is further illustrated by the following examples, which should not be construed as further limiting. The contents of all references, pending patent applications and published patents, cited throughout this application are hereby expressly incorporated by reference. The siRNAs described herein were designed to target the ubiquitously expressesd gene SSB (Sjogren syndrome antigen B; NM_009278.4).

Linker groups may be connected to the oligonucleotide strand(s) at a linkage attachment point (LAP) and may include any carbon-containing moiety, in some embodiments having at least one oxygen atom, at least one phosphorous atom, and/or at least one nitrogen atom. In some embodiments, the phosphorous atom forms part of a terminal phosphate, or phosphorothioate, group on the linker group, which may serve as a connection point for the oligonucleotide strand. In certain embodiments, the nitrogen atom forms part of a terminal ether, ester, amino or amido (NHC(O)—) group on the linker group, which may serve as a connection point for the linkers of interest, endosomolytic unit, cell penetrating peptide, solubilizing group, lipid, targeting group, or additional linkers of interest. These terminal linker groups include, but are not limited to, a $C_6$ hexyl, $C_5$ secondary-hydroxy, $C_3$ thiol or $C_6$ thiol moiety. An example from the RNA sequences described below is C6 hexyl: $[(CH_2)_6 NH_2]$.

siRNA sequences described in the Examples herein are as follows:

R1

R1p Passenger
[omeG][omeC][omeC]AA[omeU]A[omeU][omeC][omeU]G[omeU][omeC]A[omeU][omeC]A AA[$(CH_2)_6NH_2$]

R1g Guide
[p][fluU][fluU][fluU]GA[fluU]GA[fluC]AGA[fluU][fluU][fluU][fluU]GG[fluCs][rUs]U R1cg Cholesterol Guide
[p][fluU][fluU][fluU]GA[fluU]GA[fluC]AGA[fluU][fluU][fluU][fluU]GG[fluCs][rUs]U[5Chol]

R2

R2p Passenger
[$(CH_2)_6NH_2$][iB][dA][fluC][dA][dA][fluC][dA][dG][dA][fluC][fluU][fluU][fluU][dA][dA][fluU][dG][fluU][dA][dA][dTs]dT[iB]

R2g Guide
[fluU][fluU]A[fluC][omeA][fluU][fluU][omeA][omeA][omeA][omeG][fluU][fluC][flu][omeG][fluU][fluU][omeG][fluU][omeUs][omeU]

R3

R3p Passenger
[$(CH_2)_6NH_2$][iB][dA][dA][dA][fluU][fluC][dA][fluU][dG][dG][fluU][dG][dA][dA][dA][flu][dA][dA][dA][dA][dTs]dT[iB]

R3g Guide
UUU[fluU][omeA][fluU][fluU][fluU][fluC][omeA][fluC][fluC][omeA][fluU][omeG][omeA][fluU][fluU][fluU][omeUs][omeU]

R4

R4p Passenger

[omeA][omeC]AA[omeC][omeC]GA[omeC][omeU]
[omeU][omeU]AA[omeU]G[omeU]AA[(CH$_2$)$_6$NH$_2$]

R4g Guide

[p][fluU][fluU]A[fluC]A[fluU][fluU]AAAG[fluU][fluC]
[fluU]G[fluU][fluU]G[fluUs][rUs]U R4cg Cholesterol Guide

[p][fluU][fluU]A[fluC]A[fluU][fluU]AAAG[fluU][fluU]
[fluU]G[fluU][fluU]G[fluUs][rUs]U[5Chol]

R5

R5cp Cholesterol Passenger

[(CH$_2$)$_6$NH$_2$][omeA][omeC]AA[omeC][omeU]GA[omeC]
[omeU][omeU][omeU]AA[omeU]G[ome]AA[5Chol]

R6

R6p Passenger

[(CH$_2$)$_6$NH$_2$][omeA][omeC]AA[omeC][omeU]GA[omeU]
[omeU][omeU][omeU]AA[omeU]G[ome]AA[C3SH]

R7

R7p Passenger

[omeA][omeC]AA[omeC][omeU]GA[omeC][omeU]
[omeU][omeU]AA [omeU]G[omeU]AA[C3SH]

R8

R8p Passenger

[(CH$_2$)$_6$NH$_2$][omeA][omeC]AA[omeC][omeU]GA[omeC]
[omeU][omeU][omeU]AA[omeU]G[oMeU]AA[(CH$_2$)$_6$NH$_2$]

R9

R9cp Passenger

[(CH$_2$)$_6$NH$_2$][iB][fluA][omeC][fluA][fluA][omeC][fluA]
[fluG][fluA][omeC][omeC][omeU][omeU][fluA][fluA]
[omeU][fluG][omeU][fluA][fluA][dTs]dT[iB][5Chol]

R9g Guide

[p]dT[fluU][omeA][omeC][fluA][omeU][omeU][fluA]
[fluA][fluA][fluG][omeU][omeC][fluU][fluG][omeU]
[omeU][fluG][omeU][omeUs][omeU]

The peptides described in the Examples herein are as follows:

```
                                     (SEQ ID NO: 35)
P1 CRQIKIWFQNRRMKWKKGGNH2;

(SEQ ID NO: 43)
P2 D(NHC12H25)NleKNleKNleHNleKNleHNleCNH2;

(SEQ ID NO: 43)
P3 CD(NHC12H25)NleKNleKNleHNleKNleHNleNH2;

(SEQ ID NO: 28)
P4 [HS(CH2)2CO] KLLKLLLKLWLKLLKLLLKLLNH2;

(SEQ ID NO: 29)
P5 m(Peg)44 LHLLHHLLHHLHHLLHHLLHLLHHLLHHLCNH2;

(SEQ ID NO: 36)
P6 CRKKRRQRRRPPQNH2;

(SEQ ID NO: 29)
P7 CLHLLHHLLHHLHHLLHHLLHLLHHLLHHLNH2;

(SEQ ID NO: 29)
P8 HS(CH2)2CONH(Peg)27LHLLHHLLHHLHHLLHHLLHLLHHLLH
   HLNH2;
   and (SEQ ID NO: 54)
P9 CGLFEAIEGFIENGWEGMIDGWYGYGRKKRRQRRNH2.
```

Example 1

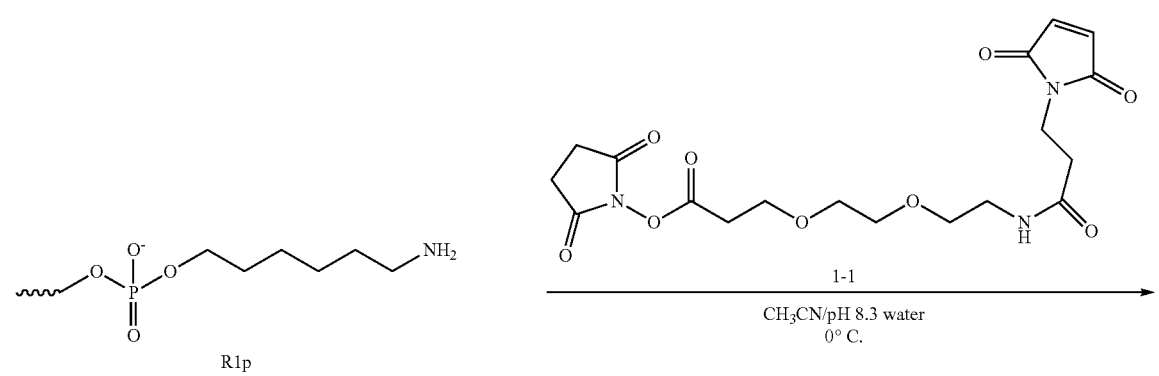

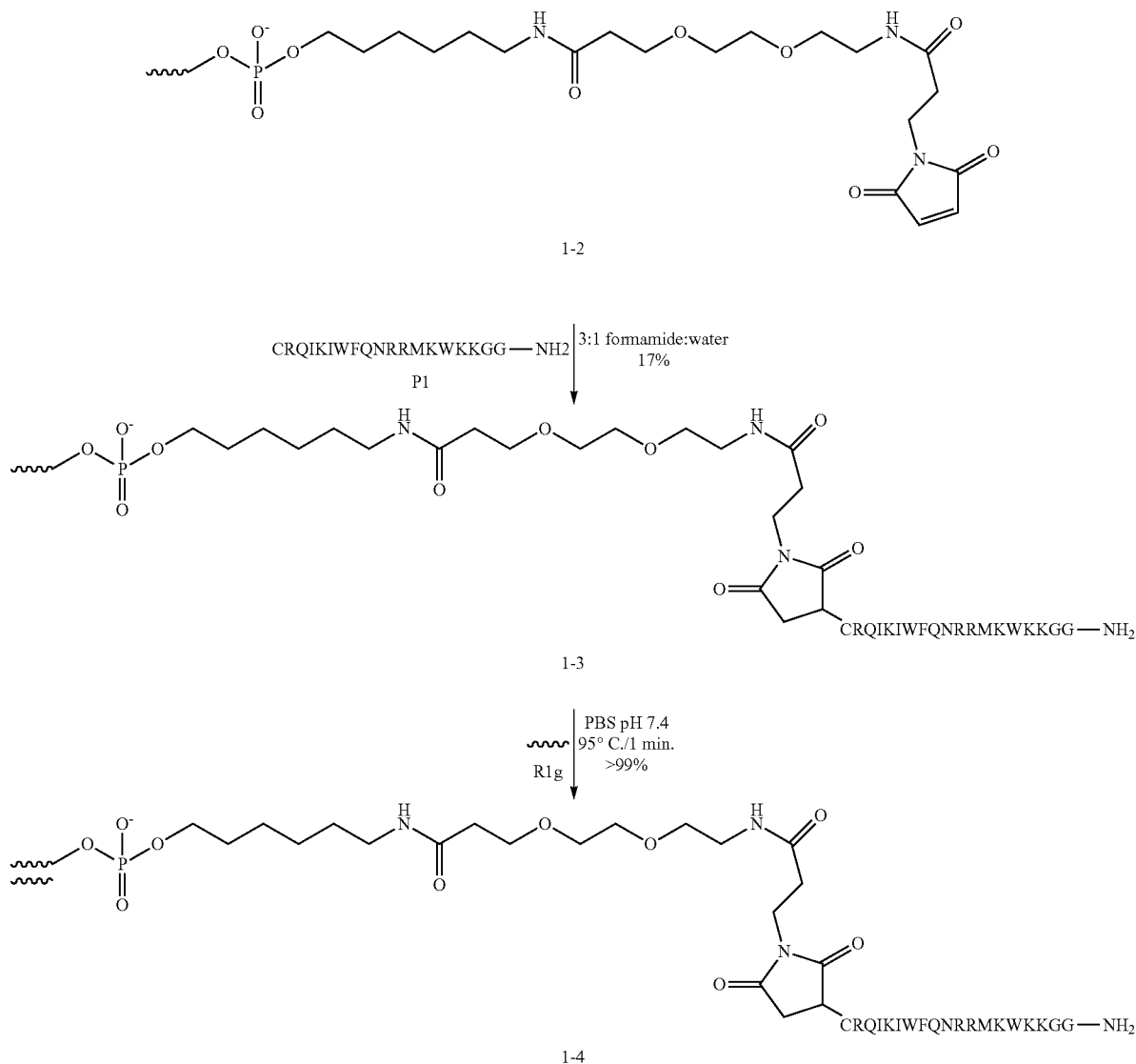

Step 1

A solution of 15.2 mg (2.40 mmol) R1p in 1.5 mL pH 8.3 water was cooled to 0° C. and treated with a solution of 7.7 mg (0.018 mmol) 1-1 in 1.0 mL acetonitrile added dropwise. The resulting solution was stirred at room temperature for 0.5 h. The crude reaction was diluted with 18 mL water and the pH adjusted to 6.0 with acetic acid. The resulting solution was centrifugally dialyzed four times against water using a MW 3000 dialysis membrane. The dialyte was lyophilized to provide 13.5 mg of the desired product 1-2 as a fluffy white amorphous powder, measured mass=6635.

Step 2

A solution of 3 mg (0.452 µmol) 1-2 in 570 uL 3:1 formamide:water and 30 µl 2M TEAA was treated with a solution of 2.23 mg (0.904 mol) P1 in 600 µL 3:1 formamide:water and the resulting solution stirred at RT for 1.5 h. The crude reaction was purified by preparatory anion exchange chromatography on a Gilson apparatus using a 6 mL ResourceQ column and a 70:30-0:80% A:B linear gradient (A=20 mM Tris.HCl, 50% formamide, pH 6.8; B=20 mM Tris.HCl, 400 mM NaClO4, 50% formamide, pH 6.8). Product peak was diluted with water, and was centrifugally dialyzed four times against water using a MW 3000 dialysis membrane. The dialyte was lyophilized to provide 0.7 mg of the desired conjugate 1-3 as a fluffy white amorphous powder. Product yield was assessed by UV assay (260 nm) of the reconstituted lyophilized material in pH 7.4 PBS buffer.

Step 3

A solution of 0.7 mg (0.077 µmol) reconstituted 1-3 was treated with a solution of 0.63 mg (0.092 µmol) of R1g in 65 µl of pH 7.4 PBS buffer. The resulting solution was heated to 95° C. for one minute, was cooled and was centrifugally dialyzed three times against water using a MW 3000 dialysis membrane. The dialyte was lyophilized to provide 1.5 mg of the desired duplex product 1-4 as a fluffy white amorphous powder. Duplex was confirmed by MS, measured mass=passenger strand: 9098, guide strand: 6786.

In a manner similar to that described above for the synthesis of 1-4 were prepared the following compounds:

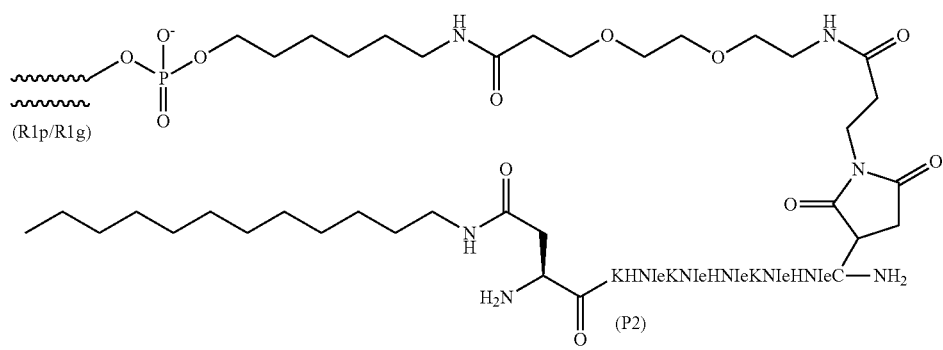
1-5
Measured mass = duplex 15317
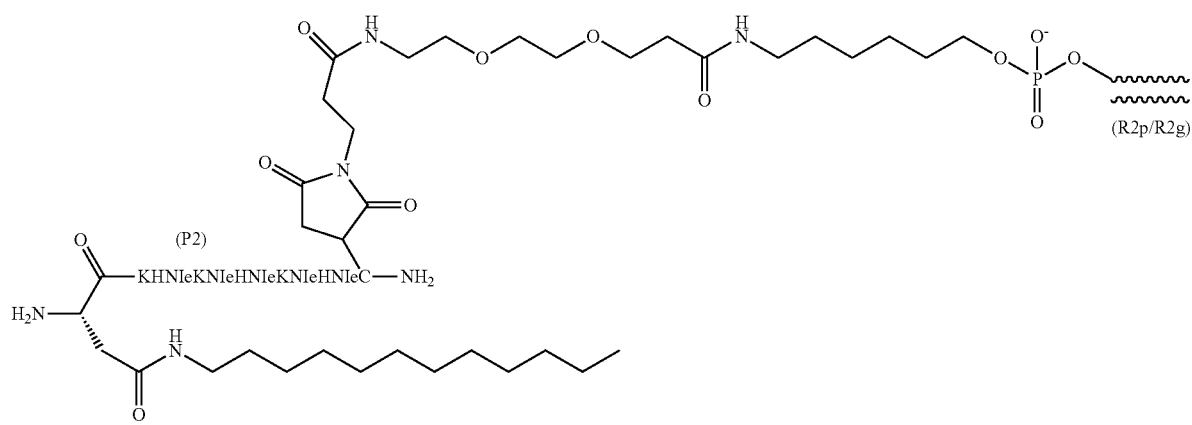
1-6
Measured mass = duplex 15881
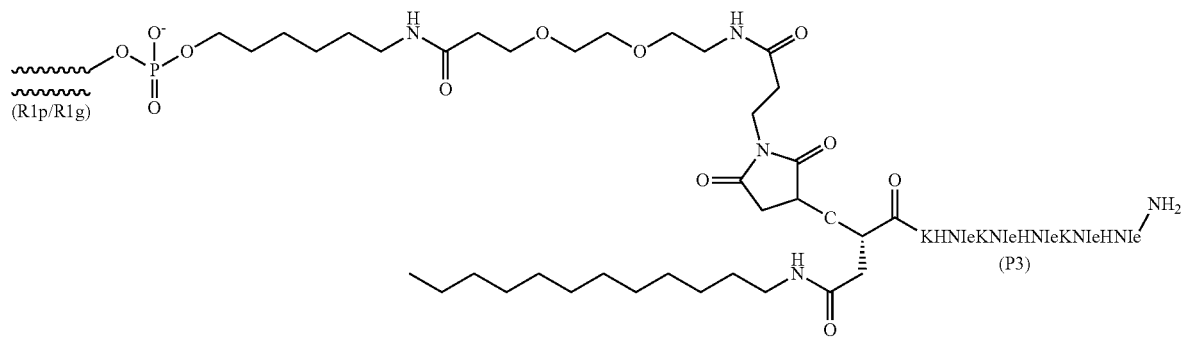
1-7
Measured mass = duplex 15467
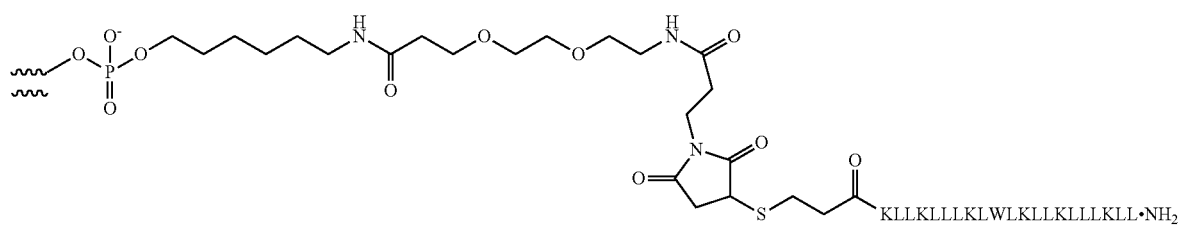
1-8
Measured mass = passenger 9280, guide 6785

1-9
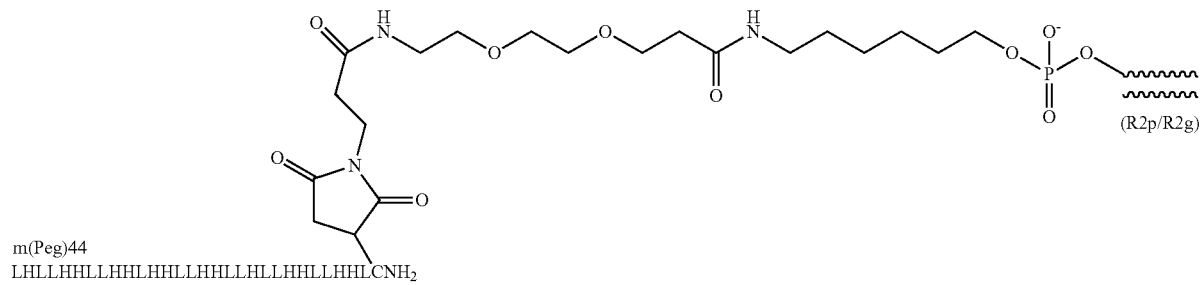
m(Peg)44
LHLLHHLLHHLHHLLHHLLHLLHHLLHHLCNH₂
(P5)
Measured mass = duplex 19500
1-10
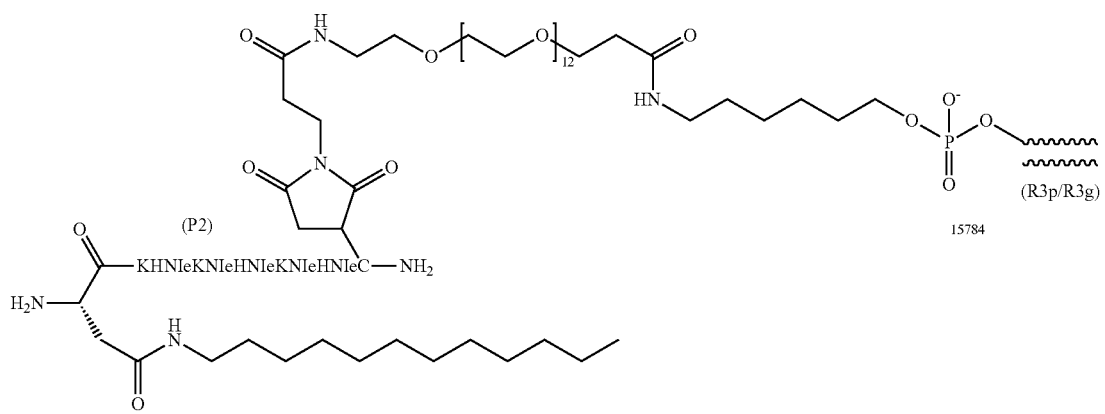
Measured mass = passenger 7825, guide 6632
Example 2
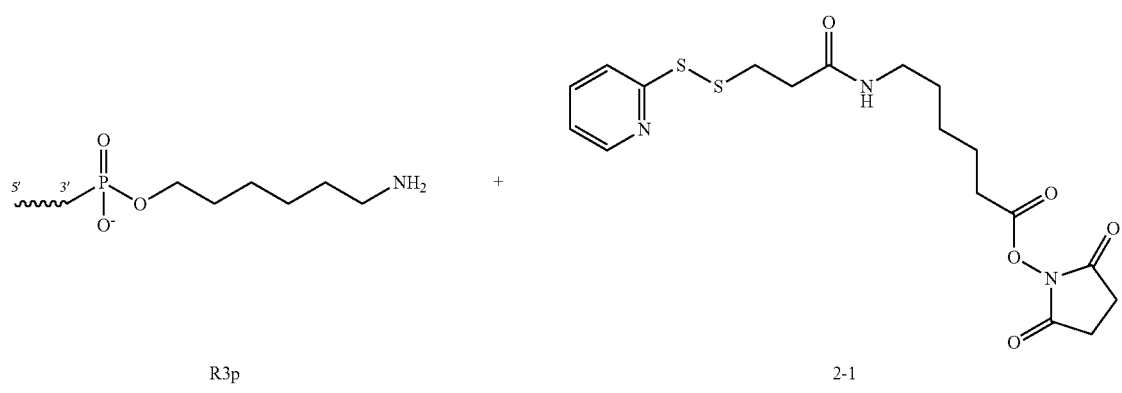
pH 8.3 water/ACN

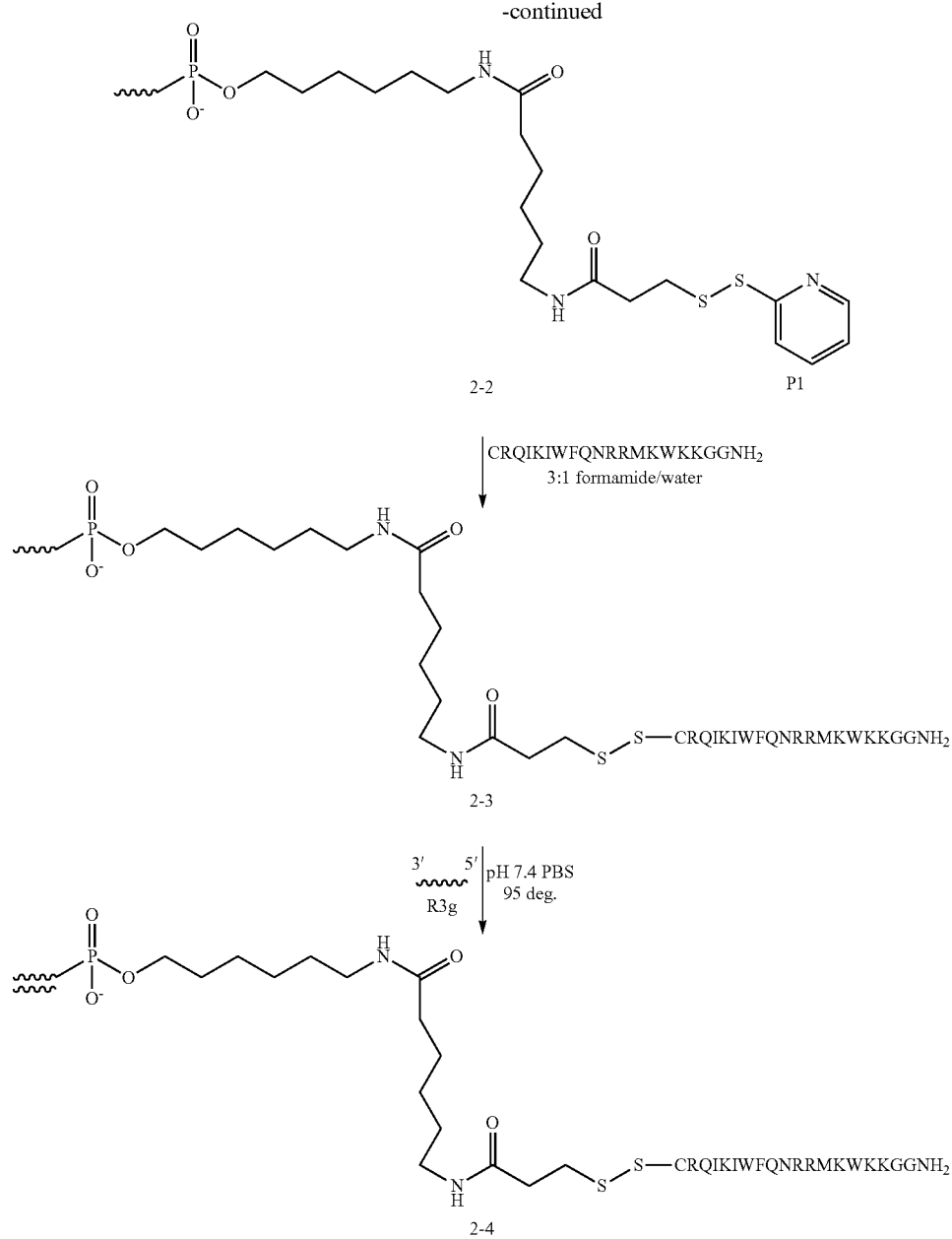

Step 1

A solution of 15.00 mg (2.14 μmol) of R3p in 1 ml of pH 8.3 water was treated with a solution of 6.38 mg (15.00 μmol) of 2-1 in 1 ml of acetonitrile. The resulting solution was stirred at room temperature for 1 h, and the crude reaction purified by anion exchange prep LC (6 ml Resource Q Anion exchange column; A=50% 0.02 mmol Tris/50% formamide; B=50% 0.02 mmol Tris-400 mmol NaOCl4/50% formamide 30-100% A:B gradient over 30 min., 10 ml/min flow). Pure Fractions were combined, diluted with water, and centrifugally dialyzed 3× versus water using a MW 300 dialysis membrane. The combined aqueous material was frozen and lyophilized overnight to give 7.31 mg of the desired product 2-2 as an amorphous white powder. LC/MS: measured mass=7387; purity=>99%.

Step 2

A solution of 5.00 mg (0.673 μmol) of 2-2 in 950 μl of 3:1 formamide:water was treated with 50 μl of TEAA, and the solution treated with a solution of 3.32 mg (1.347 μmol) of P1 in 1000 μl of 3:1 formamide:water. The resulting solution was stirred for 18 h, and the crude reaction purified by anion exchange prep LC (6 ml Resource Q Anion exchange column; A=50% 0.02 mmol Tris/50% formamide; B=50% 0.02 mmol Tris-400 mmol NaOCl4/50% formamide 30-100% A:B gradient over 30 min., 10 ml/min flow). The purified fractions were combined, diluted with water, and centrifugally dialyzed 3× versus water. The combined aqueous material was frozen and lyophilized overnight to give 5.18 mg of the desired product 2-3 as a white amorphous powder. LC/MS: measured mass=9737; purity=>99%, no excess peptide present as determined by HPLC and MS.

Step 3

A solution of 5.00 mg (0.511 μmol) of 2-3 in 200 μl of pH 7.4 PBS was treated with a solution of 3.39 mg (0.511 μmol) of R3g in 100 μl of pH 7.4 PBS. The resulting solution was heated at 95 deg. C. for one minute, and was cooled to RT. The solution was diluted with water, and was dialyzed 3× versus water. The aqueous material was frozen and lyophilized overnight to give 3.22 mg of the desired product 2-4 as a white amorphous powder. LC/MS: measured mass passenger=9737, guide=6631.

In a manner similar to that described above for the synthesis of 2-4 were prepared the following compounds:

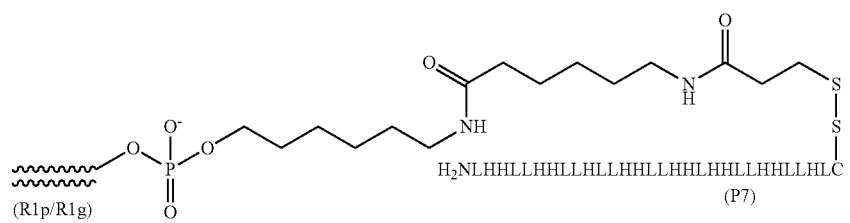

Measured mass = duplex 17500

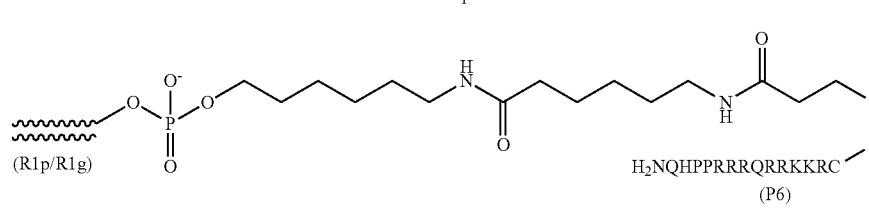

Measured mass = duplex 15340

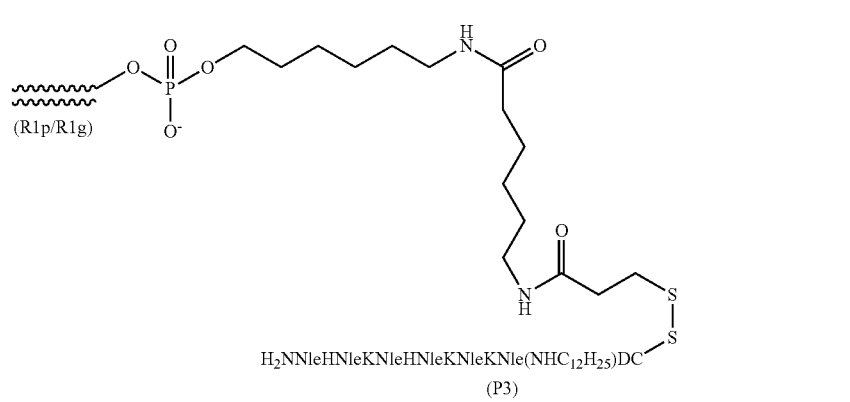

Measured mass = 8286 passenger, 6785 guide

Example 3

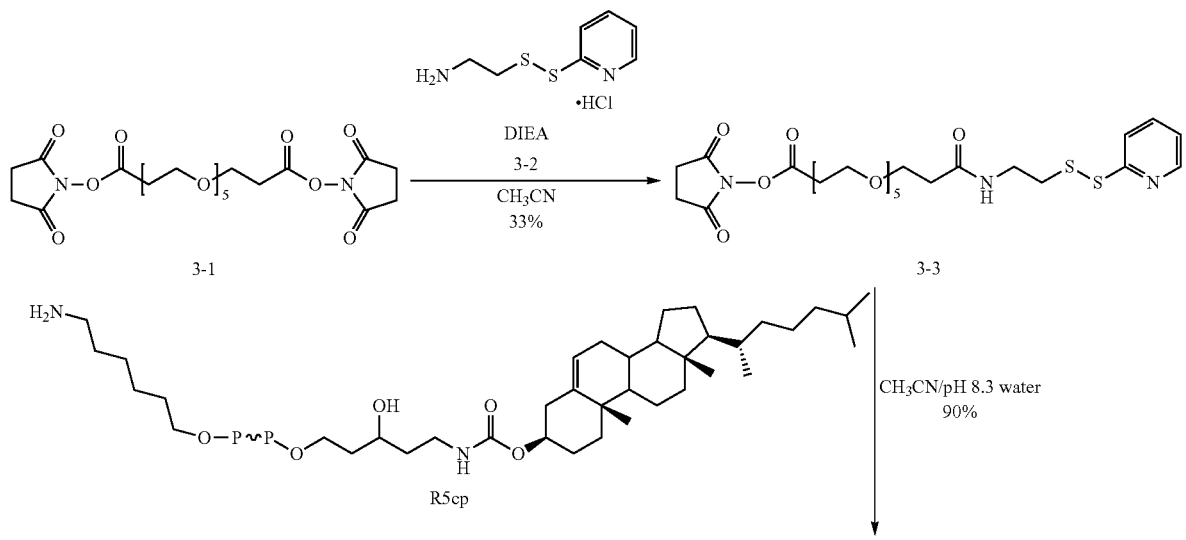

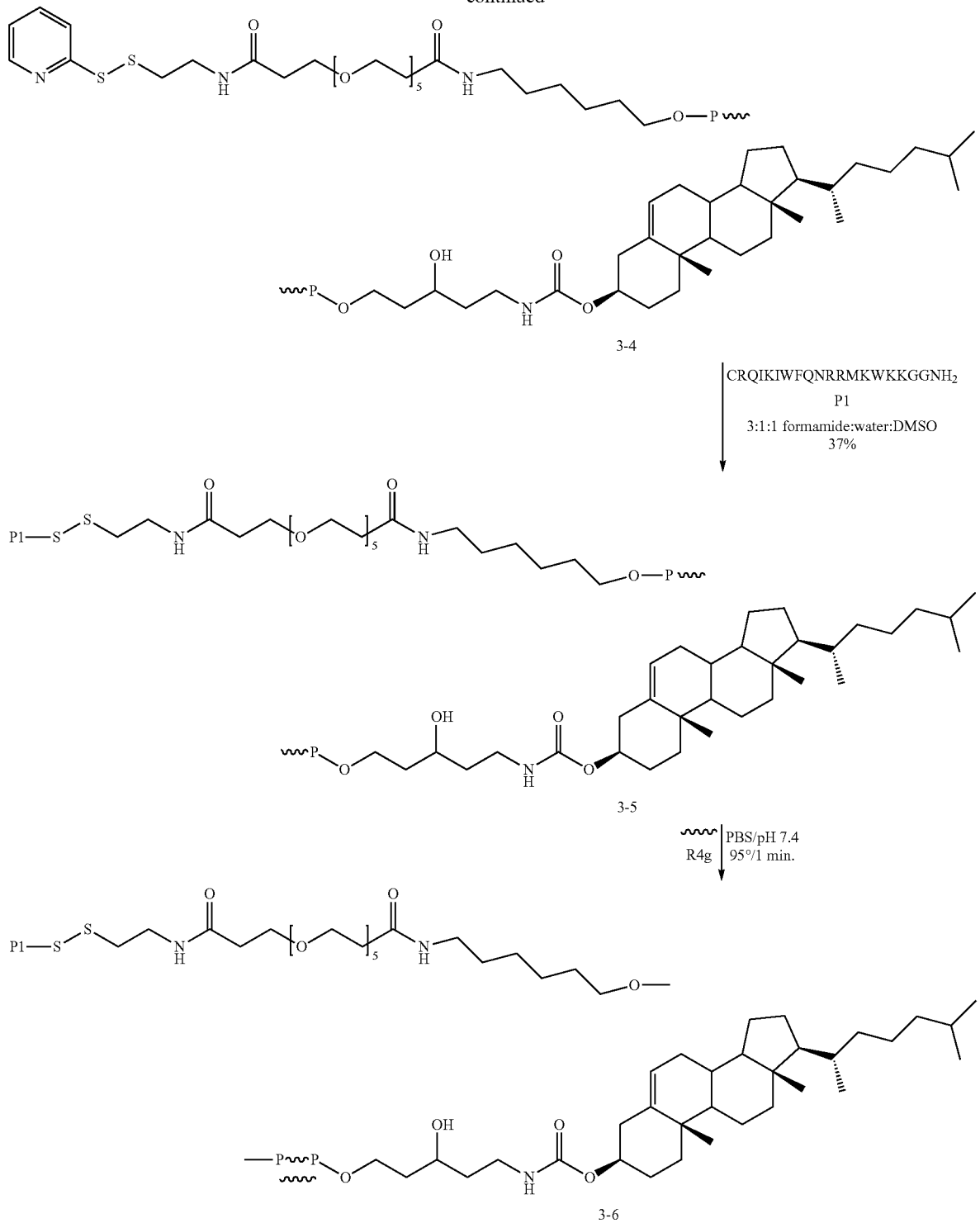

Step 1

A solution of 63 mg (0.283 mmol) of 3-2 in 1.5 ml of acetonitrile was treated with 43.9 mg (0.339 mmol) of diisopropylethylamine. The resulting solution was added slowly dropwise to a solution of 300 mg (0.566 mmol) of 3-1 in 1.5 ml of acetonitrile. The resulting solution was stirred at room temperature for 18 h, and was concentrated in vacuo. The resulting oil was separated reverse phase prep LC on a Gilson apparatus using a Phenomenex Gemini C18 column to give 60 mg (35%) of the desired product 3-3 as a clear oil. $^1$H NMR (CDCl$_3$): 2.54 (t, 2H), 2.83 (m, 4H), 2.90 (t, 2H), 2.96 (t, 2H), 3.58 (m, 2H), 3.66 (m, 10H), 3.72 (br m, 6H), (t, 2H), 3.84 (t, 2H), 7.21 (m, 1H), 7.72 (m, 2H), 8.54 (d, 1H).

Step 2

A solution of 54.9 mg (0.091 mmol) of 3-3 in 10 ml of acetonitrile was added to a solution of 90 mg (0.013 mmol) of R5 cp in 10 ml pH 8.3 water. The resulting solution was stirred at room temperature for 18 h. The reaction was concentrated in vacuo to remove acetonitrile, and was diluted with 50 ml of water. The resulting solution was centrifugally dialyzed three times against water using a MW 3000 dialysis membrane. The dialyte was lyophilized to provide 90 mg (94%) of the desired product 3-4 as a fluffy white amorphous powder. LC/MS Measured mass=7417; purity=90%.

Step 3

A solution of 4.00 mg (0.539 mop of 3-4 in 1 ml of 3:1:1 formamide:water:DMSO was treated with a solution of 4.00 mg (1.635 μmol) of P1 in 1 ml of 3:1:1 formamide:water: DMSO and the resulting solution stirred at room temperature for 5 h. The crude reaction was purified by preparatory anion exchange chromatography on a Gilson apparatus using a DNA Pac 100 column and a 70:30-A:B linear gradient (A=50% formamide/50% 20 mM Tris-Cl/pH7.4; B=50% formamide/50% 20 mM Tris-C1/400 mM NaOCl$_4$/pH7.4). Suspected product peak was diluted with water, and was centrifugally dialyzed four times against water using a MW 3000 dialysis membrane. The dialyte was lyophilized to provide 2 mg of the desired conjugate 3-5 as a fluffy white amorphous powder. LC/MS: measured mass=9769, purity=95%, no residual peptide present.

Step 4

A solution of 2.00 mg (0.205 mop of 3-5 in 1 ml of pH 7.4 PBS buffer was treated with a solution of 1.38 mg (0.205 μmol) of R4g in 0.25 ml of pH 7.4 PBS buffer. The resulting solution was heated to 95° C. for one minute, was cooled and was centrifugally dialyzed three times against water using a MW 3000 dialysis membrane. The dialyte was lyophilized to provide 1.2 mg of the desired duplex 3-6 as a fluffy white amorphous powder. Duplex confirmed by MS, measured mass=passenger strand 9770, guide strand 6733.

In a manner similar to that described above for the synthesis of 3-5 was prepared the following compound:

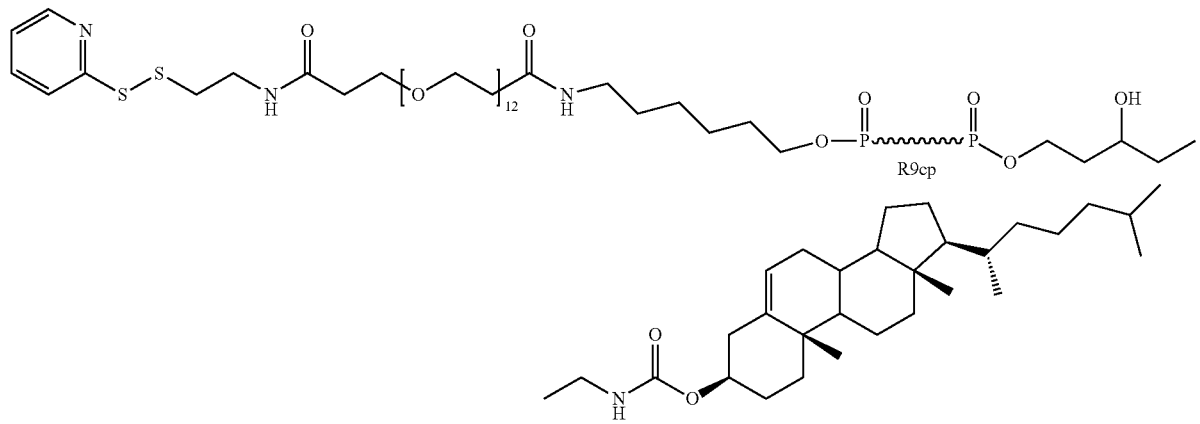

3-5a

Measured mass = 7770

In a manner similar to that described above for the synthesis of 3-6 were prepared the following compounds:

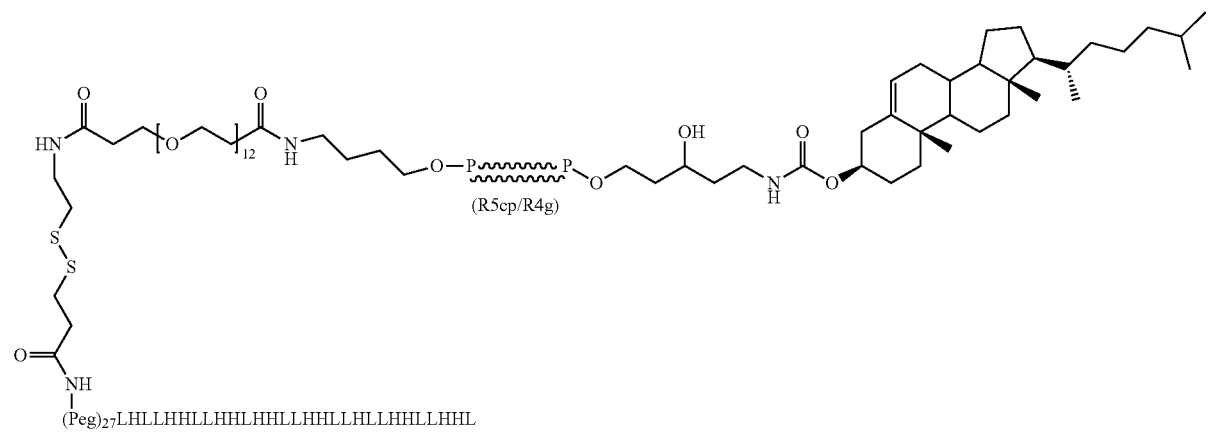

3-7

Measured mass = 12021 passenger, 6733 guide

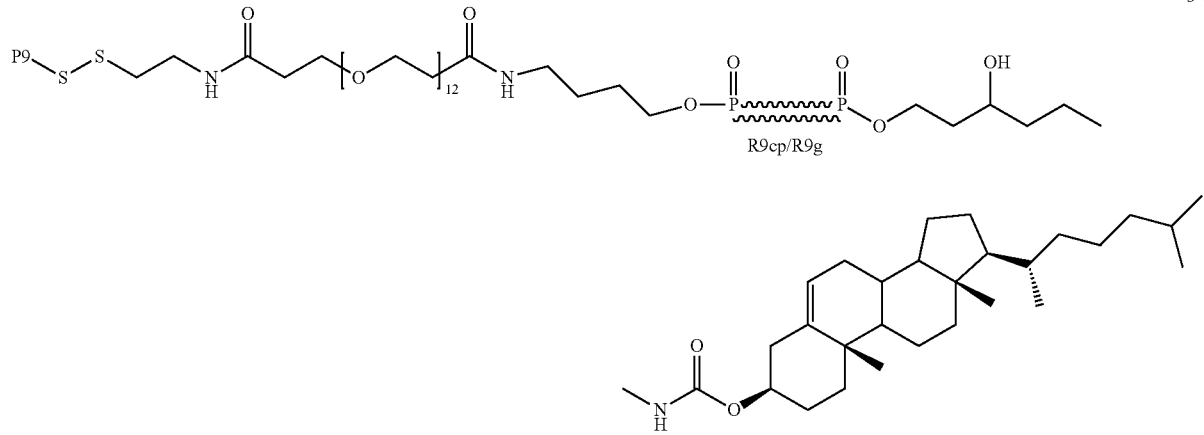
Measured mass = 11692 passenger, 6783 guide
Example 4
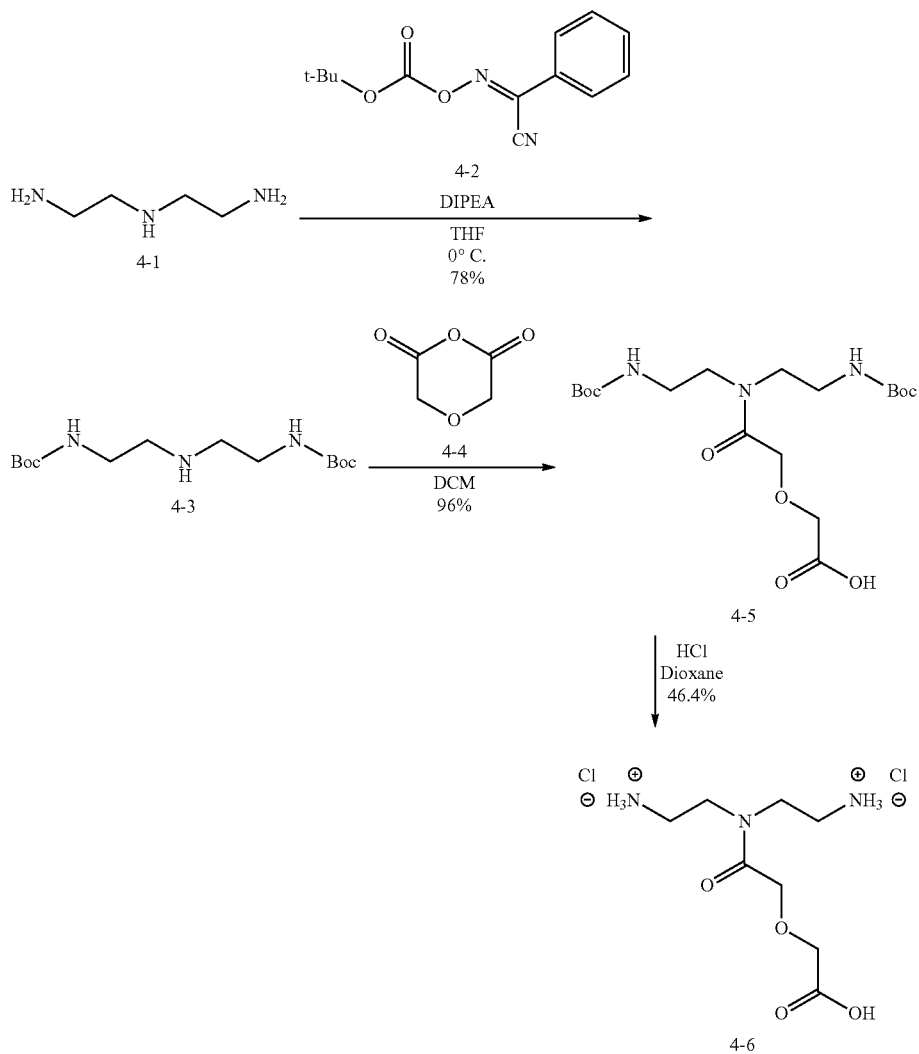

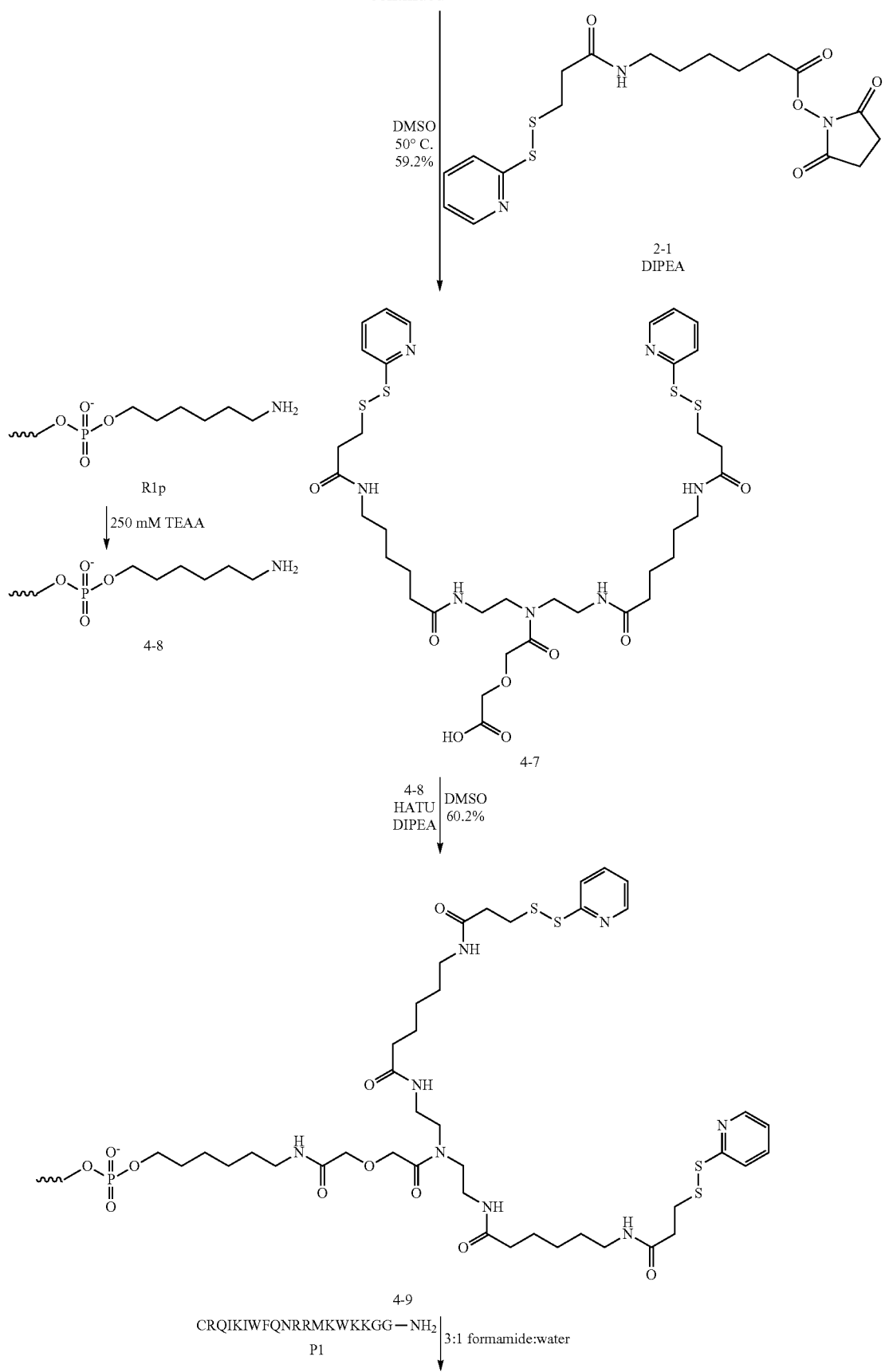

-continued

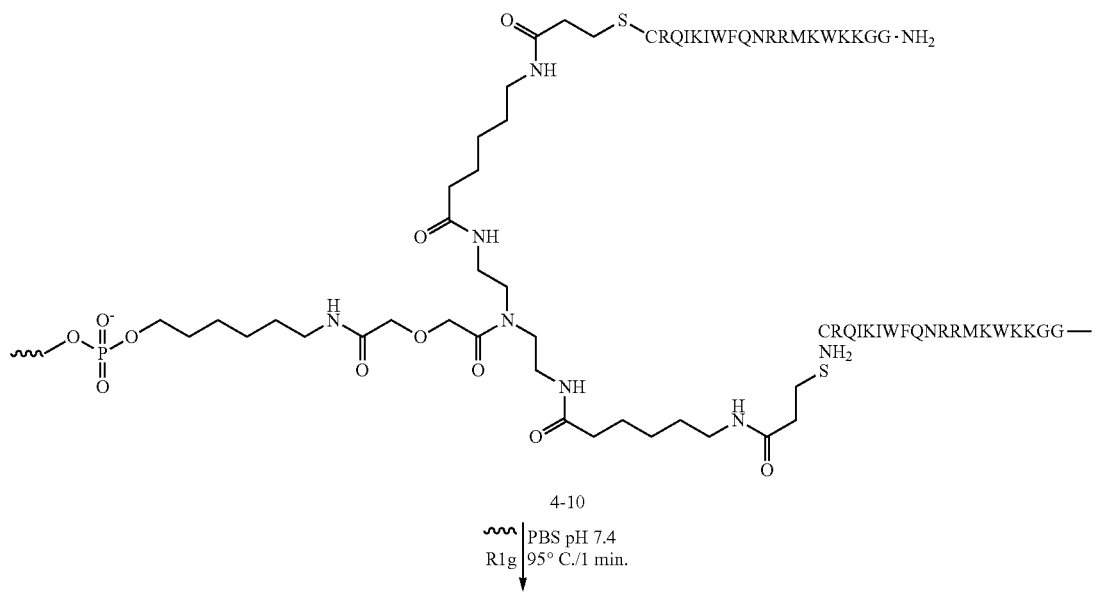

4-10

↓ PBS pH 7.4
R1g 95° C./1 min.

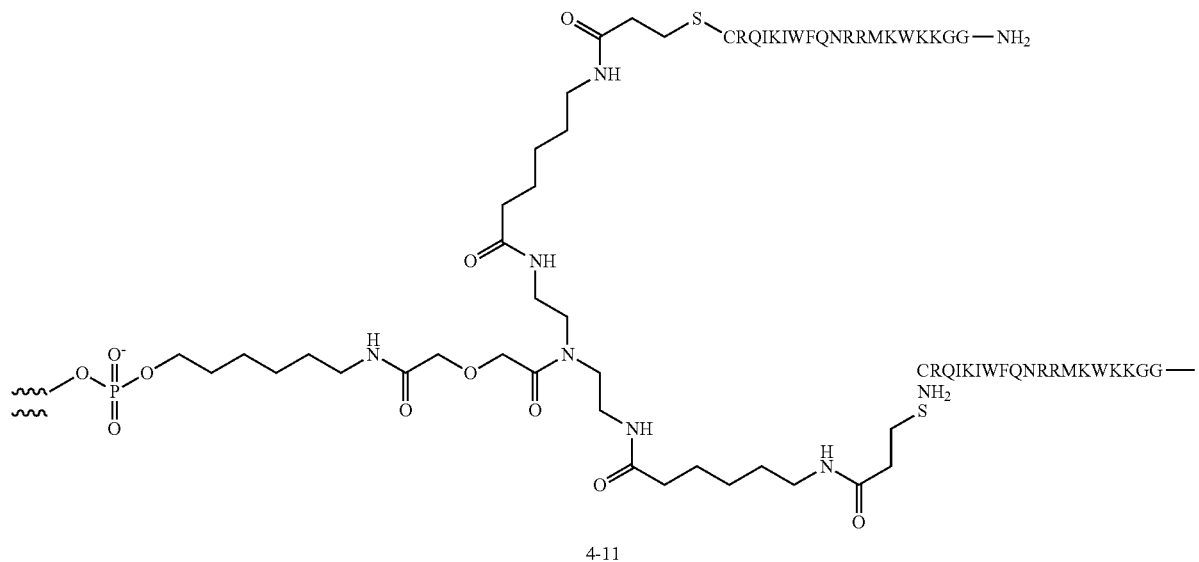

4-11

Step 1

A solution of 3.13 mL (29.1 mmol) of 44 and 15.24 mL (87 mmol) DIPEA in 150 mL THF in a nitrogen purged round bottom flask was cooled to 0° C. and was treated with a solution of 14.3 g (58.2 mmol) of 4-2 in 60 mL THF added dropwise. The resulting solution was stirred at 0° C. for one hour, then allowed to warm to room temperature. The crude reaction was diluted with 300 mL DCM and washed with 150 mL 1 N NaOH. The organic layer was separated and concentrated in vacuo, then purified by flash chromatography (9:1 DCM: MeOH, 1% NH$_4$OH) to give 6.84 g 4-3. $^1$H NMR (CDCl$_3$): 1.45 (s, 18H), 2.73 (bt, 4H), 3.21 (m, 4H), 4.89 (bs, 2H).

Step 2

A solution of 5.44 g (17.93 mmol) 4-3 in 55 mL DCM was treated 2.77 g (17.93 mmol) 4-4 added in one portion. The resulting solution was stirred for 0.5 hr, after which the crude reaction mixture was concentrated in vacuo and purified by flash chromatography (100:0-0:100% A:B linear gradient [A=hexanes, B=ethyl acetate]) to give 7.2 g 4-5 as a white solid. $^1$H NMR (CDCl$_3$): 1.44 (sd, 18H), 3.25-3.40 (m, 6H), 3.52 (bt, 2H), 4.19 (s, 2H), 4.42 (s, 2H), 4.88 (bt, 1H), 5.33 (bs, 1H). Measured mass=420.5 (M+1)

Step 3

1.0 g (2.38 mmol) 4-5 was treated with 32.5 ml anhydrous HCl 4 M in dioxane, resulting in gas evolution and a white precipitate after 15 minutes. The resulting slurry was filtered and the amorphous solid was dissolved in water, then lyophilized to give 380 mg 4-6. $^1$H NMR (DMSO): 2.9-3.1 (m, 4H), 3.53 (bq, 4H), 4.15 (s, 2H), 4.33 (s, 2H), 8.14 (ds, 6H). Measured mass=220.3 (M+1)

Step 4

A slurry of 30 mg (0.087 mmol) 4-6 and 76 uL (0.436 mmol) DIPEA in 300 μL DMSO was treated with a solution of 76.75 mg (0.18 mmol) 2-1 in 300 μL DMSO. The resulting slurry was heated at 50° C. for 40 minutes with intermittent sonication to achieve homogeneity. The crude reaction was diluted with 1.5 mL DMSO and acidified with 1.6 mL 0.1% aqueous TFA. The solution was purified reverse phase prep LC on a Gilson apparatus using a Phenomenex Gemini C18 column (95:5-5:95% A:B linear gradient [A=water with 0.1% TFA, B=acetonitrile with 0.1% TFA]) to give 43.40 mg 4-7. $^1$H NMR (DMSO): 1.20 (m, 2H), 1.3-1.5 (m, 8H), 2.03 (bq, 4H), 3.01 (m, 8H), 3.1-3.3 (m, 8H), 4.09 (s, 2H), 4.24 (s, 2H), 7.25 (m, 2H), 7.7-7.95 (m, 8H), 8.45 (m, 2H). Measured mass=421.0 (M+2)

Step 5

50 mg (7.91 μmol) R1p centrifugally dialyzed three times against 250 mM TEAA, then twice against water using a MW 3000 dialysis membrane. The dialate was lyophilized to give triethylammonium adduct 4-8 as a fluffy white amorphous powder.

Step 6

A solution of 39.9 mg (0.047 mmol) 4-7 and 18.04 mg (0.047 mmol) HATU in 650 μL DMSO was treated with 12.2 μL (0.071 mmol) DIPEA. After 20 minutes, the resulting solution was added to a solution of 50 mg (7.91 μmol) 4-8 and 12.2 μL (0.071 mmol) DIPEA in 2.65 mL DMSO. The resulting solution was stirred at room temperature for 0.5 hr. The crude reaction was purified reverse phase prep LC on a Gilson apparatus using a Waters phenyl Xbridge column (95:5-5: 95% A:B linear gradient [A=water with 250 mM TEAA, B=acetonitrile with 250 mM TEAA]). Suspected product peak was diluted with water, and was centrifugally dialyzed four times against water using a MW 3000 dialysis membrane. The dialyte was lyophilized to provide 34 mg of the desired conjugate 4-9 as a fluffy white amorphous powder, measured mass=7147.

Step 7

A solution of 5 mg (0.700 μmol) 4-9 in 950 μL 3:1 formamide:water and 50 μL 2M TEAA was treated with a solution of 3.45 mg (1.40 μmol) P1 in 1.0 mL 3:1 formamide:water and the resulting solution stirred at RT for 0.5 h. An additional 1.72 mg (0.7 μmol) P1 added to the reaction. The crude reaction was purified by preparatory anion exchange chromatography on a Gilson apparatus using a 6 mL ResourceQ column and a 100:0-0:100% A:B linear gradient (A=20 mM Tris.HCl, 50% formamide, pH 6.8; B=20 mM Tris.HCl, 400 mM NaClO4, 50% formamide, pH 6.8). Suspected product peak was diluted with water, and was centrifugally dialyzed four times against water using a MW 3000 dialysis membrane. The dialyte was lyophilized to provide the desired conjugate 4-10 as an amorphous solid that was taken directly onto the next step.

Step 8

A slurry of 4-10 in 2.0 mL pH 7.4 PBS was treated with a solution of 2.37 mg (0.350 μmol) of R1g added in one portion. The resulting slurry was heated to 95° C. and allowed to cool to room temperature. Some heterogeneity was observed, prompting the addition of 2.37 mg (0.35 μmol) R1g and repeating the heating process with intermittent sonication. The resulting solution was cooled and was centrifugally dialyzed three times against water using a MW 3000 dialysis membrane. The dialyte was lyophilized to provide the desired duplex product as a fluffy white amorphous powder. Duplex was confirmed by MS, measured mass=18636.

In a manner similar to that described above for the synthesis of 4-11 was prepared the following compound:

4-12

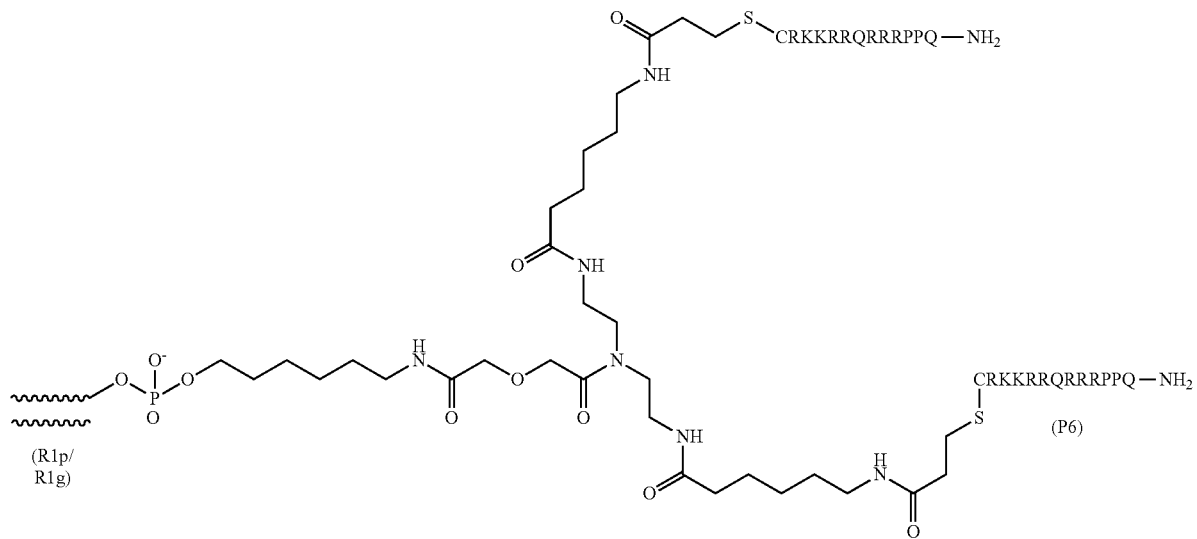

Measured mass = duplex 17239

Example 5
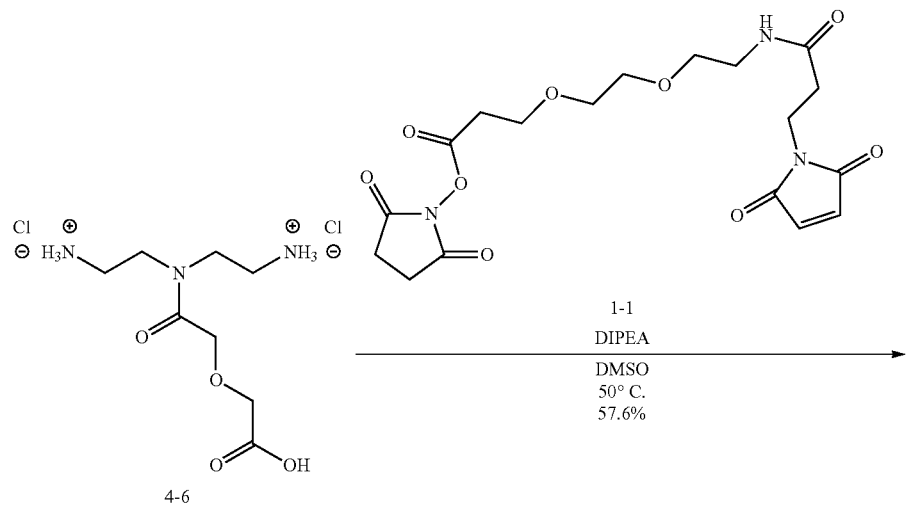
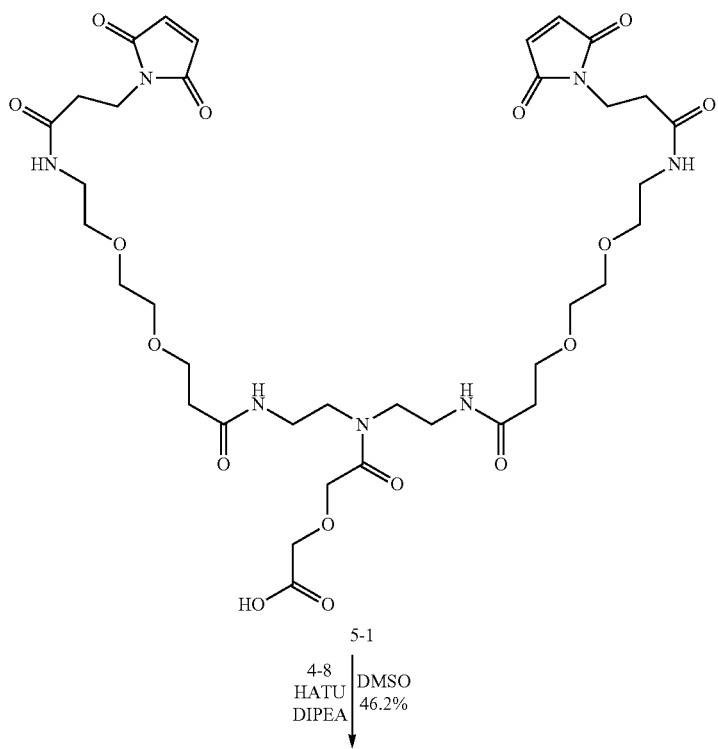

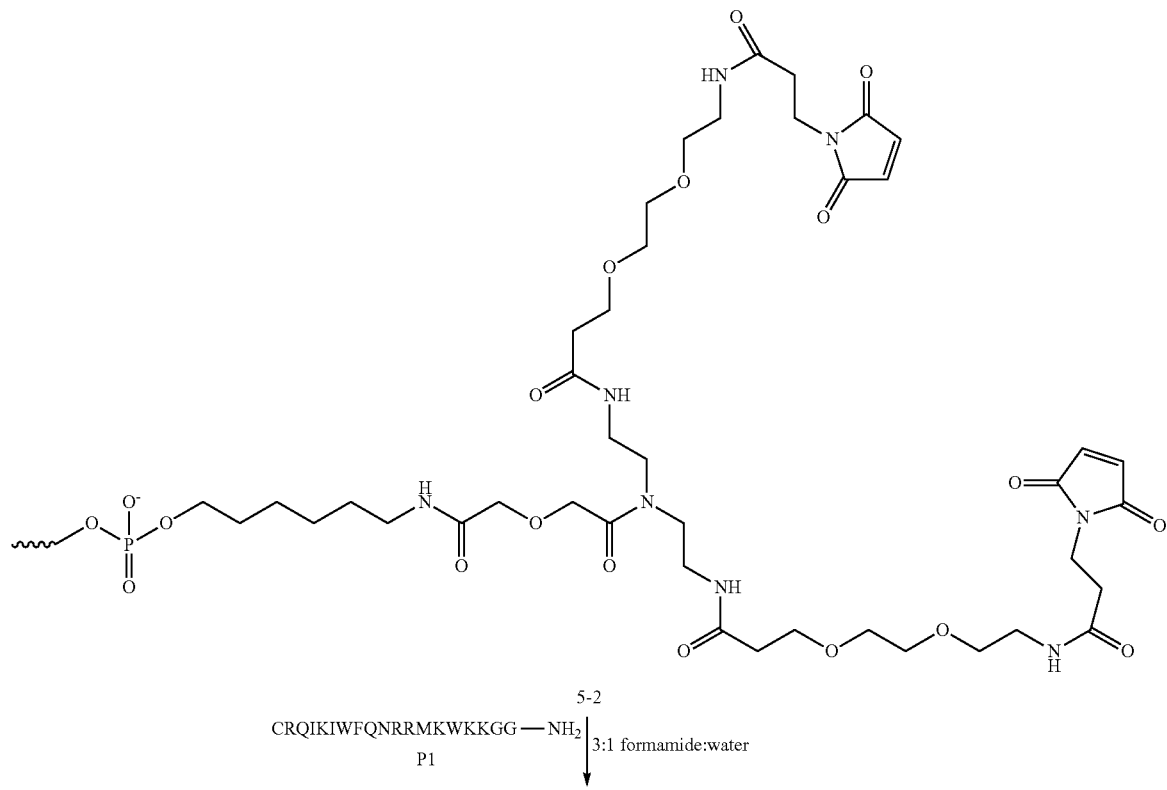
5-2
CRQIKIWFQNRRMKWKKGG—NH₂
P1
3:1 formamide:water
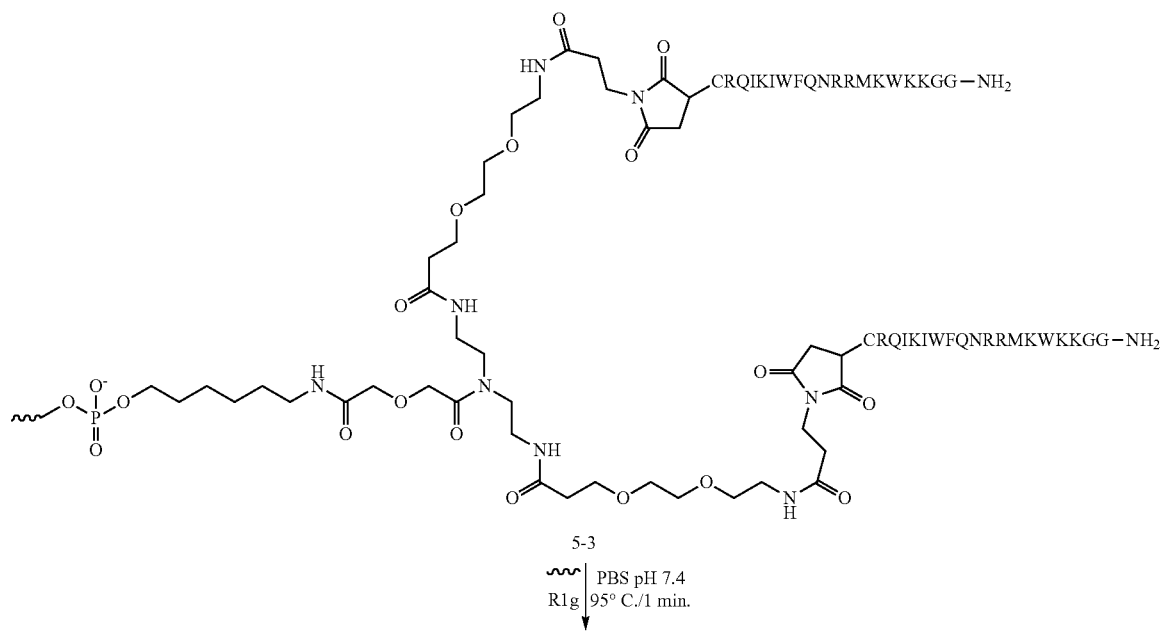
5-3
R1g ⁓ PBS pH 7.4
95° C./1 min.

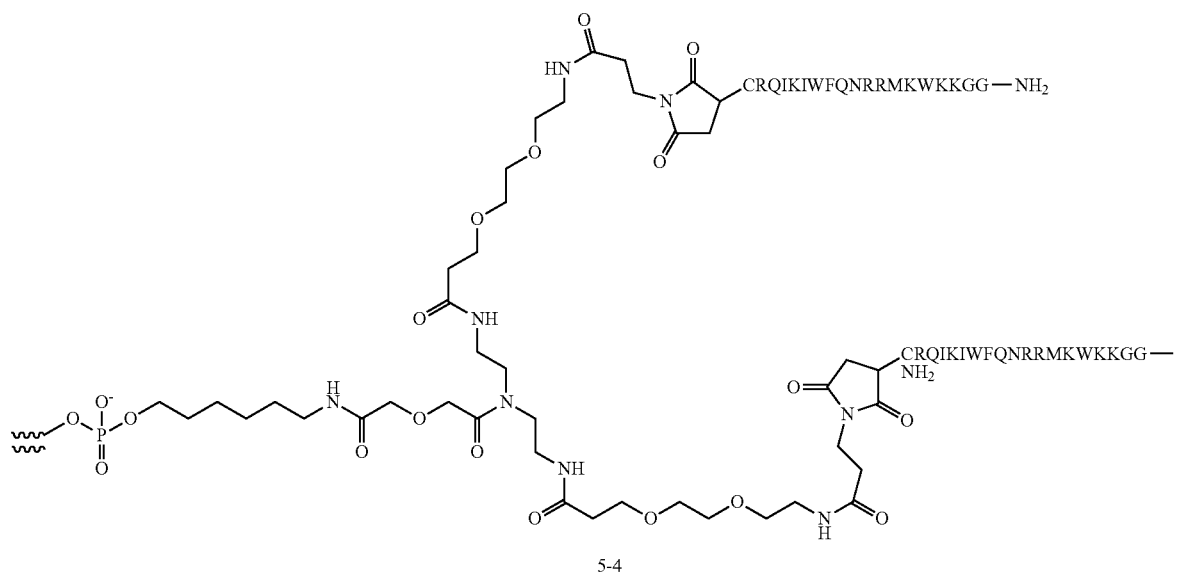

5-4

Step 1

A slurry of 60 mg (0.174 mmol) 4-6 and 152.4 µL (0.872 mmol) DIPEA in 600 µL DMSO was treated with a solution of 156 mg (0.366 mmol) 1-1 in 600 µL DMSO. The resulting slurry was heated at 50° C. for 1.5 h with agitation. The crude reaction was diluted with 1.5 mL DMSO and acidified with 1.6 mL 0.1% aqueous TFA. The solution was purified reverse phase prep LC on a Gilson apparatus using a Phenomenex Gemini C18 column (95:5-5:95% A:B linear gradient [A=water with 0.1% TFA, B=acetonitrile with 0.1% TFA]) to give 110.15 mg 5-1. $^1$H NMR (DMSO): 2.25-2.35 (m, 8H), 3.1-3.4 (m, 16H), 3.46 (s, 8H), 3.55-3.65 (m, 8H), 4.09 (s, 2H), 4.24 (s, 2H), 7.003 (s, 4H), 7.91 (bt, 1H), 8.01 (s, 2H). Measured mass=421.0 (M+2)

Step 2

A solution of 55.8 mg (0.050 mmol) 5-1 and 18.94 mg (0.050 mmol) HATU in 585 µL DMSO was treated with 11.19 µL (0.064 mmol) DIPEA. After 10 minutes, the resulting solution was added to a solution of 45 mg (7.12 µmol) 4-8 and 11.19 µl (0.064 mmol) DIPEA in 2.65 mL DMSO. The resulting solution was stirred at room temperature for 15 minutes. The crude reaction was purified reverse phase prep LC on a Gilson apparatus using a Waters phenyl Xbridge column (95:5-5:95% A:B linear gradient [A=water with 250 mM TEAA, B=acetonitrile with 250 mM TEAA]). Suspected product peak was diluted with water, and was centrifugally dialyzed four times against water using a MW 3000 dialysis membrane. The dialyte was lyophilized to provide 23.5 mg of the desired conjugate 5-2 as a fluffy white amorphous powder, measured mass=7146.

Step 3

A solution of 5 mg (0.700 µmol) 5-2 in 950 µL 3:1 formamide:water and 50 µL 2M TEAA was treated with a solution of 3.45 mg (1.40 mmol) P1 in 1.0 mL 3:1 formamide:water and the resulting solution stirred at RT for 0.5 h. An additional 1.72 mg (0.7 mmol) P1 was added to the reaction. The crude reaction was purified by preparatory anion exchange chromatography on a Gilson apparatus using a 6 mL ResourceQ column and a 100:0-0:100% A:B linear gradient (A=20 mM Tris.HCl, 50% formamide, pH 6.8; B=20 mM Tris.HCl, 400 mM NaClO4, 50% formamide, pH 6.8) Product peak was diluted with water, and was centrifugally dialyzed four times against water using a MW 3000 dialysis membrane. The dialyte was lyophilized to provide the desired conjugate 5-3 as an amorphous solid whose form precluded yield assessment. Measured Mass=12090

Step 4

A slurry of 5-3 in 300 µL pH 7.4 PBS was treated with a solution of 2.02 mg (0.298 µmol) of R1g in 200 µL pH 7.4 PBS added in one portion. The resulting slurry was heated to 95° C. and allowed to cool to room temperature. A solution of 1.15 mg (0.169 mmol) R1g in 115 µL pH 7.4 PBS and was added the heating process was repeated. The resulting solution was cooled and was centrifugally dialyzed three times against water using a MW 3000 dialysis membrane. The dialyte was lyophilized to provide the desired duplex product 5-4 as a fluffy white amorphous powder. Duplex was confirmed by MS, measured mass=18859.

In a manner similar to that described above for the synthesis of 5-4 was prepared the following compound:

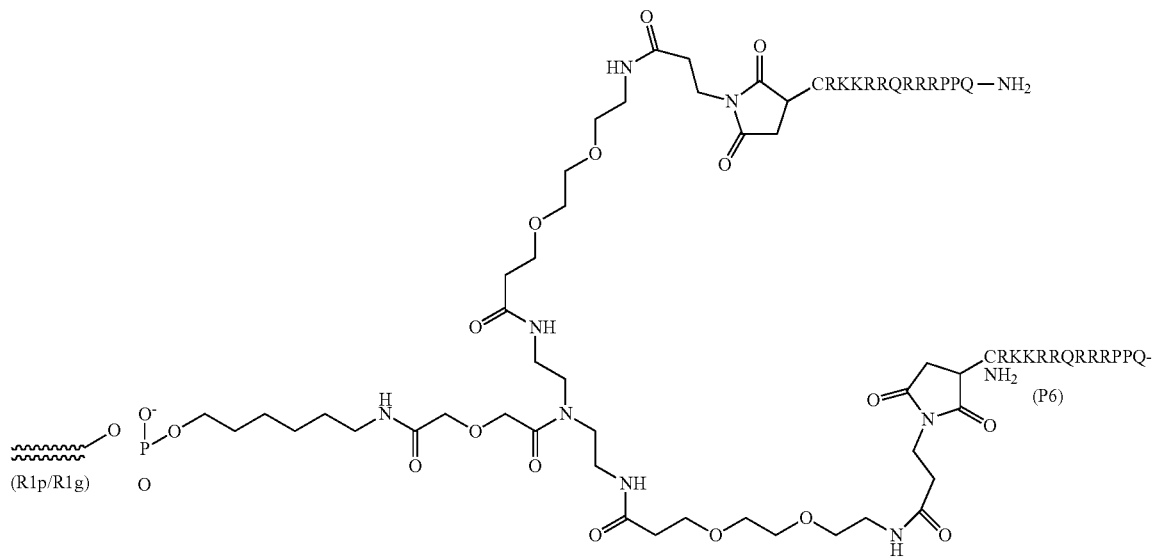
Measured mass = duplex 17461
Example 6
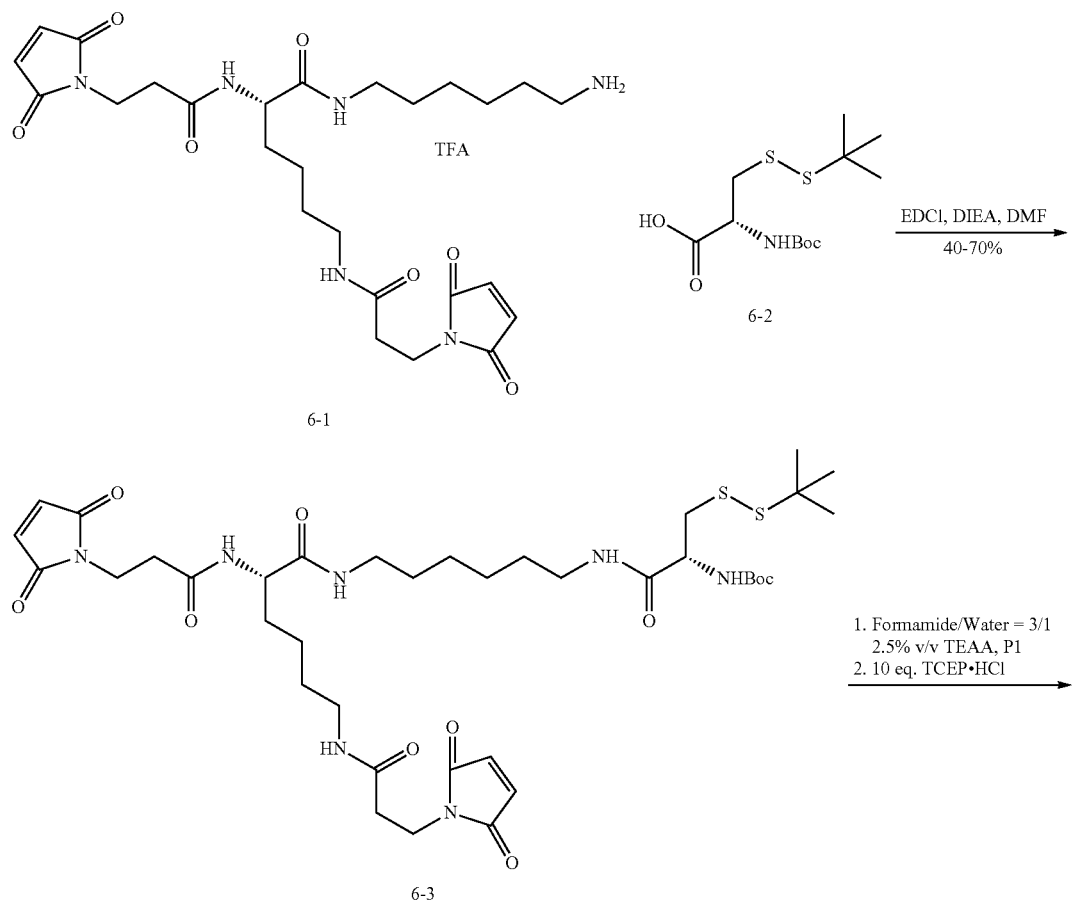

-continued
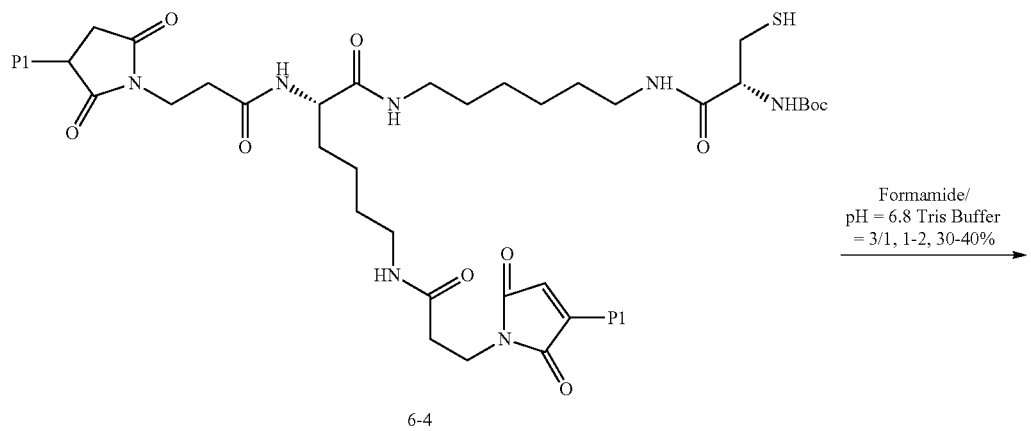
6-4
Formamide/
pH = 6.8 Tris Buffer
= 3/1, 1-2, 30-40%
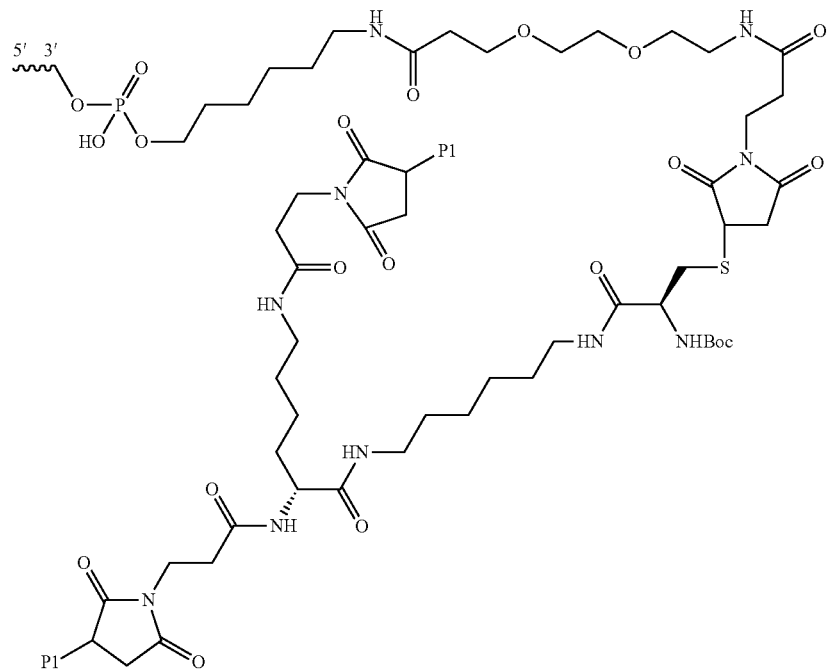
6-5
R1g
PBS, 1X Buffer
90° C., 1 min.

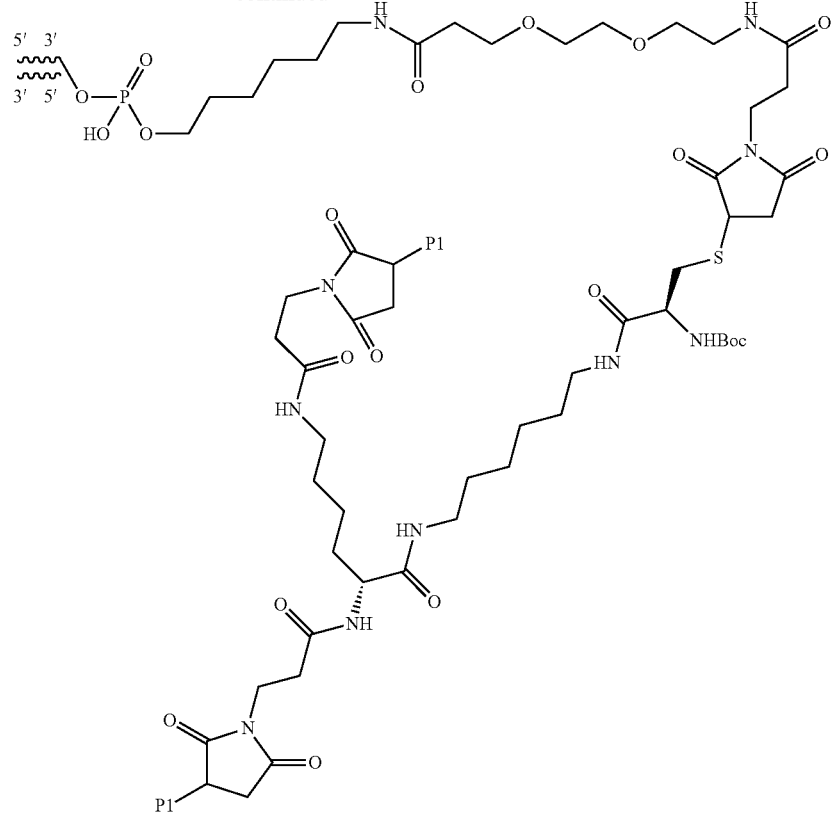

6-6

Step 1

To a solution of 6-2 (58.6 mg, 0.189 mmol) and diisopropylamine (52.8 µL, 0.303 mmol) in 1.5 mL DMF at at 0° C. was EDCI (39.2 mg, 0.303 mmol) and the resulting reaction mixture was stirred 10 min. After 10 min, solid 6-1 (100 mg, 0.152 mmol) was added to the reaction vessel in one portion followed by addition of diisopropylamine (26.5 µL, 0.152 mmol) and the reaction mixture was slowly warmed to room temperature over 30 min. Upon LC-MS analysis indicated complete consumption of the starting material, reaction mixture was diluted to 2.5 mL with MeCN/H$_2$O=1/1 and purified by C18 reverse phase HPLC (10-55% MeCN in H$_2$O over 15 min). The collected fractions were combined and lyophilized to give 6-3 as a white powder (40-70% yields), MS: 837.

The following compound was prepared as described above:

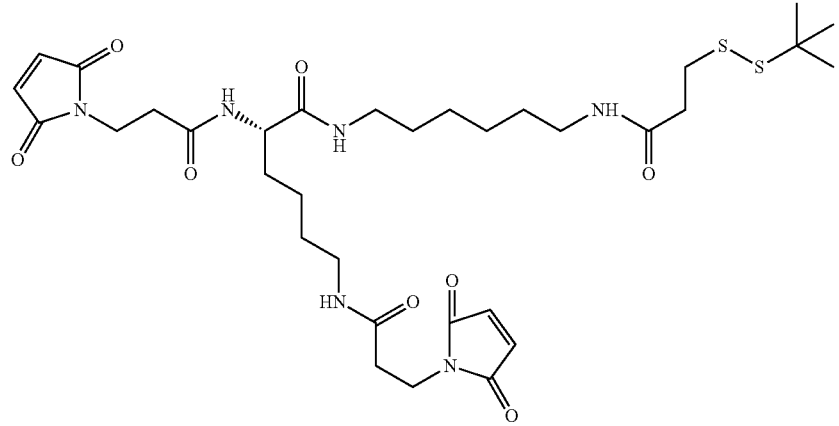

6-3a

Step 2

A solution of 6-3 (1.50 mg, 1.79 µmol) in 400 µL of formamide/H$_2$O/2 M TEAA=3/1/0.1 was treated with a solution of peptide P1 (11.0 mg, 4.47 μmol) in 200 μl of formamide/H₂O/2 M TEAA=3/1/0.1. The resulting solution was stirred at room temperature for 2 h. Upon complete consumption of 6-3, TCEP.HCl (5.12 mg, 17.9 μmol) was added and the reaction mixture was heated to 37° C. After 30 min, LC-MS analysis indicated the complete reduction of disulfide bond and the reaction mixture was diluted to 2.5 mL with MeCN/H₂O=1/1. Purification by C18 reverse phase HPLC (10-60% MeCN in H₂O over 15 min) and lyophilization afforded 6-4 as a white solid, MS: 5672.

Step 3

A solution of 1-2 (3.00 mg, 0.452 μmol) in 400 μL of formamide/pH=6.8 Tris.HCl buffer=3/1 was treated with a solution of 6-6 (3.08 mg, 0.543 μmol) in 400 μl formamide/pH=6.8 Tris.HCl buffer=3/1. The resulting solution was stirred at room temperature for 2 h. Upon complete consumption of 1-2, the reaction mixture was purified by anion exchange Resource Q column (50-100% B in A, A: formamide/H₂O=1/1, 20 mmol Tris.HCl, pH=7.4, B: formamide/H₂O=1/1, 20 mmol Tris.HCl, 400 mmol NaClO₄, pH=7.4). Combined product fractions were diluted with water, and centrifugally dialyzed 4 times against water with MW 3000 cutoff membrane. The dialyte was lyophilized to provide 6-5 as a white solid, mass=12313.

Step 4

To a solution of 6-5 (0.90 mg, 0.073 μmol) in 400 μL PBS 1× buffer was added a solution of R1g (0.51 mg, 0.075 μmol) in 400 μl PBS 1× buffer. The resulting solution was heated at 90° C. for 1 min and cooled down to room temperature. The annealing reaction mixture was diluted with water, and centrifugally dialyzed 4 times against water with MW 3000 cutoff membrane. The dialyte was lyophilized to provide 6-6 as a white solid, passenger strand mass=12313, guide strand=6865.

The following compound was prepared as described above:

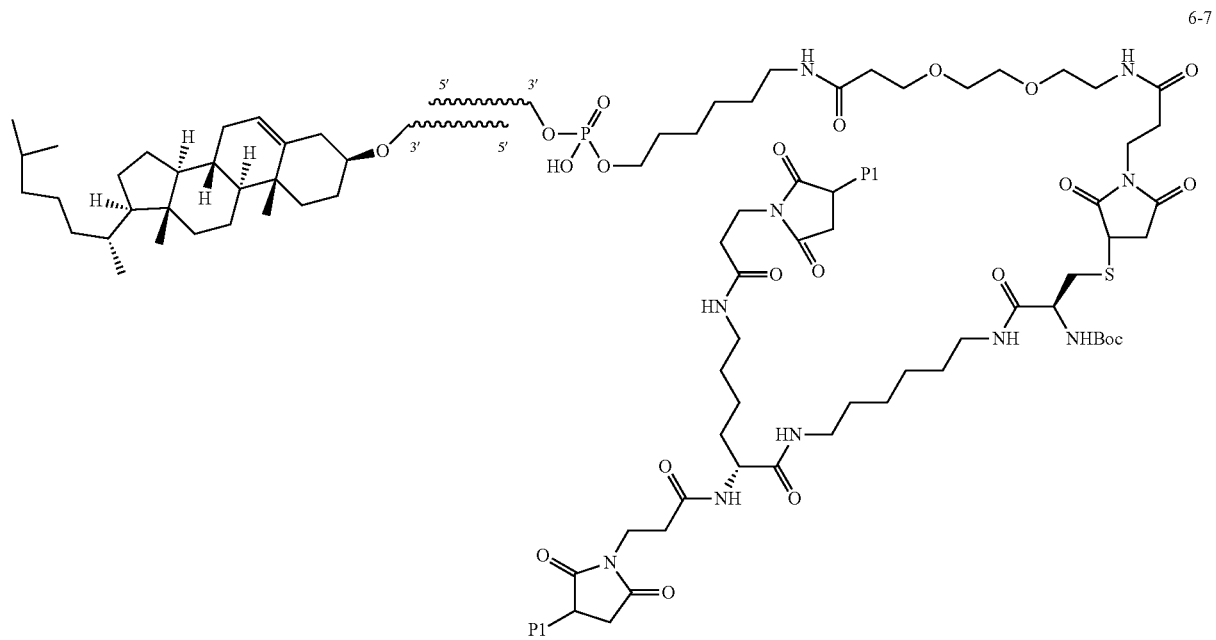

passenger strand mass=12313, guide strand=7380.

Example 7

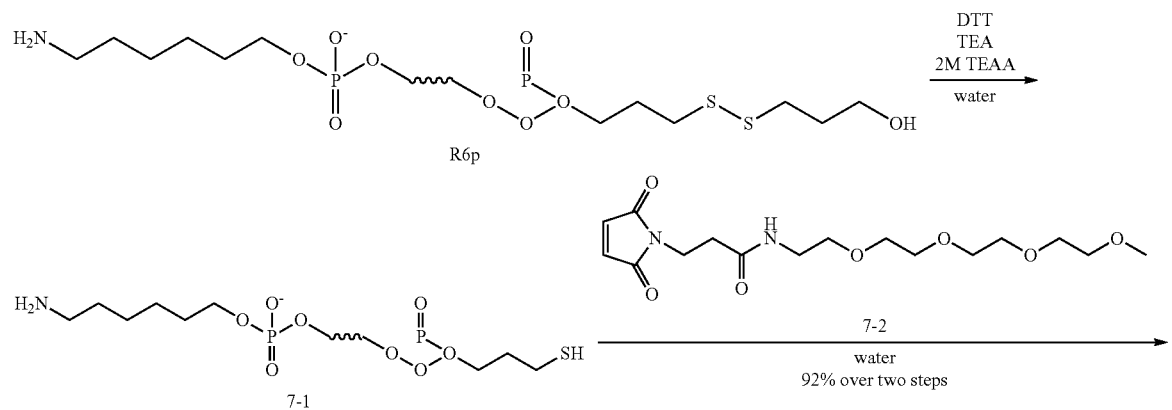

-continued
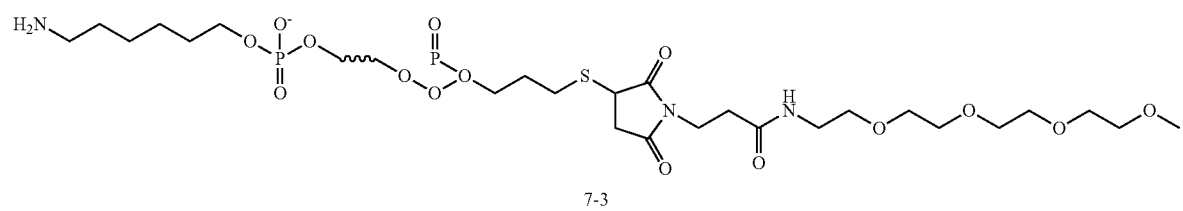
7-3
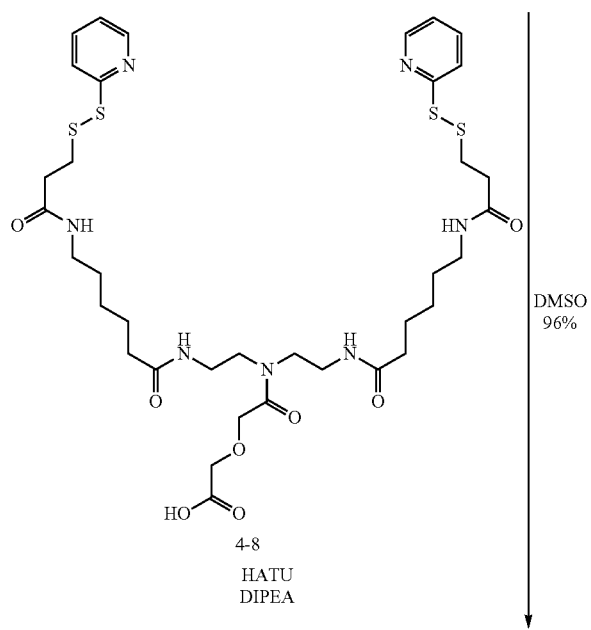
4-8
HATU
DIPEA
DMSO
96%
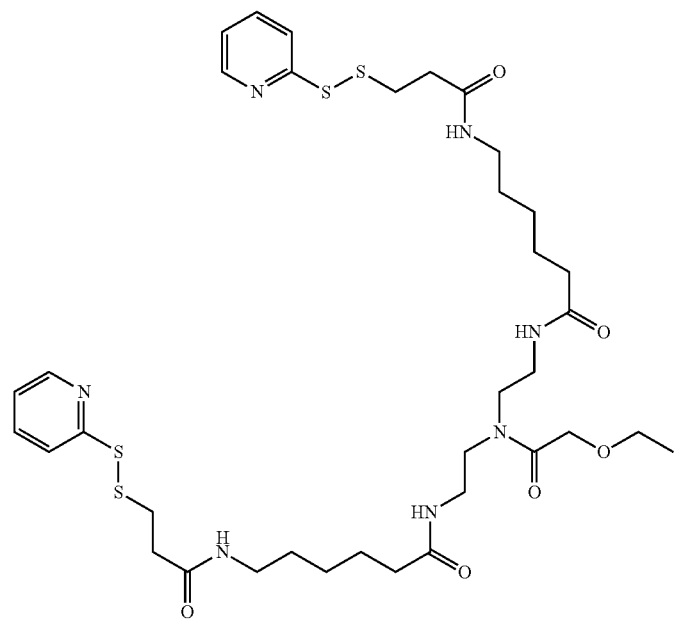

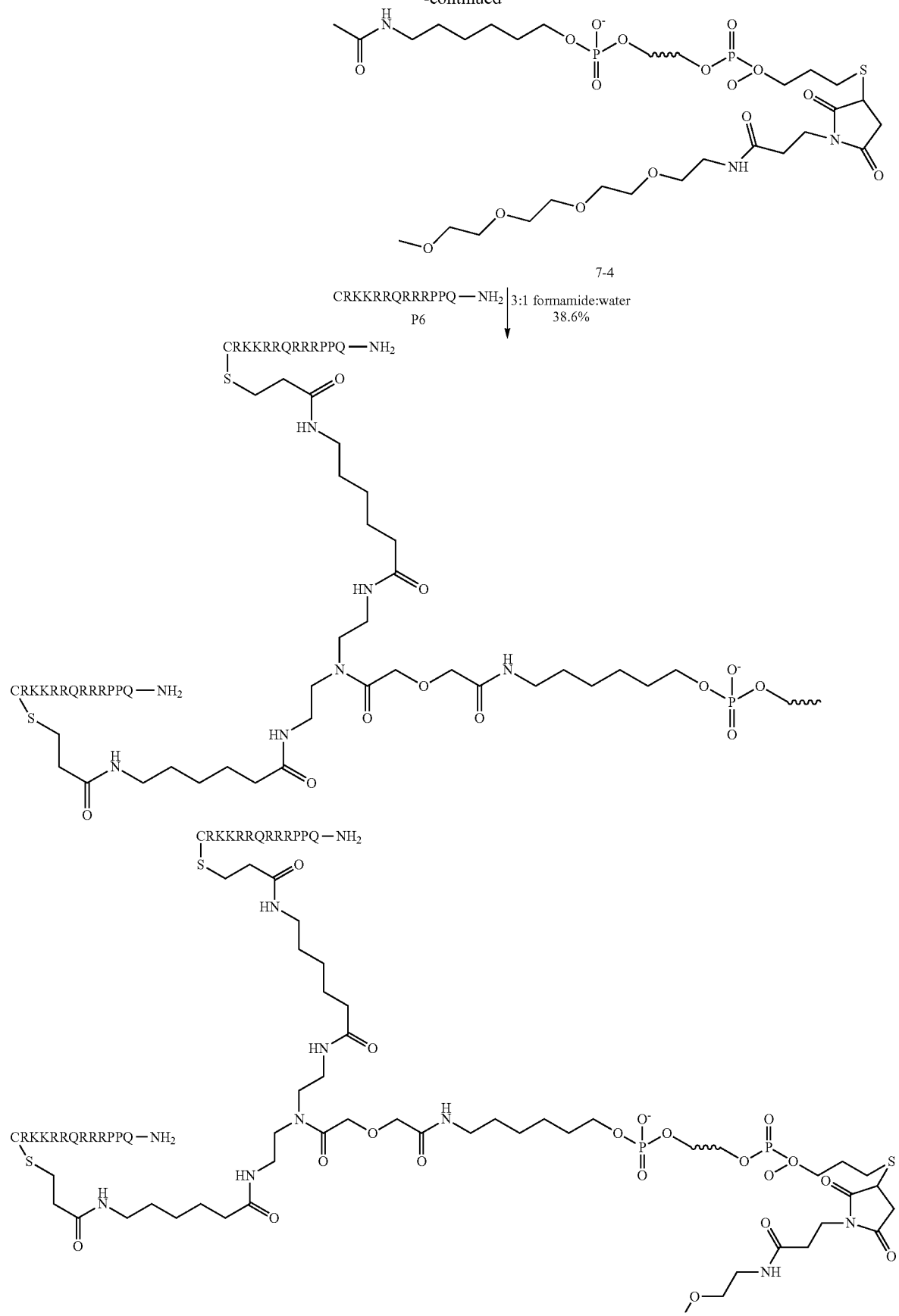

-continued

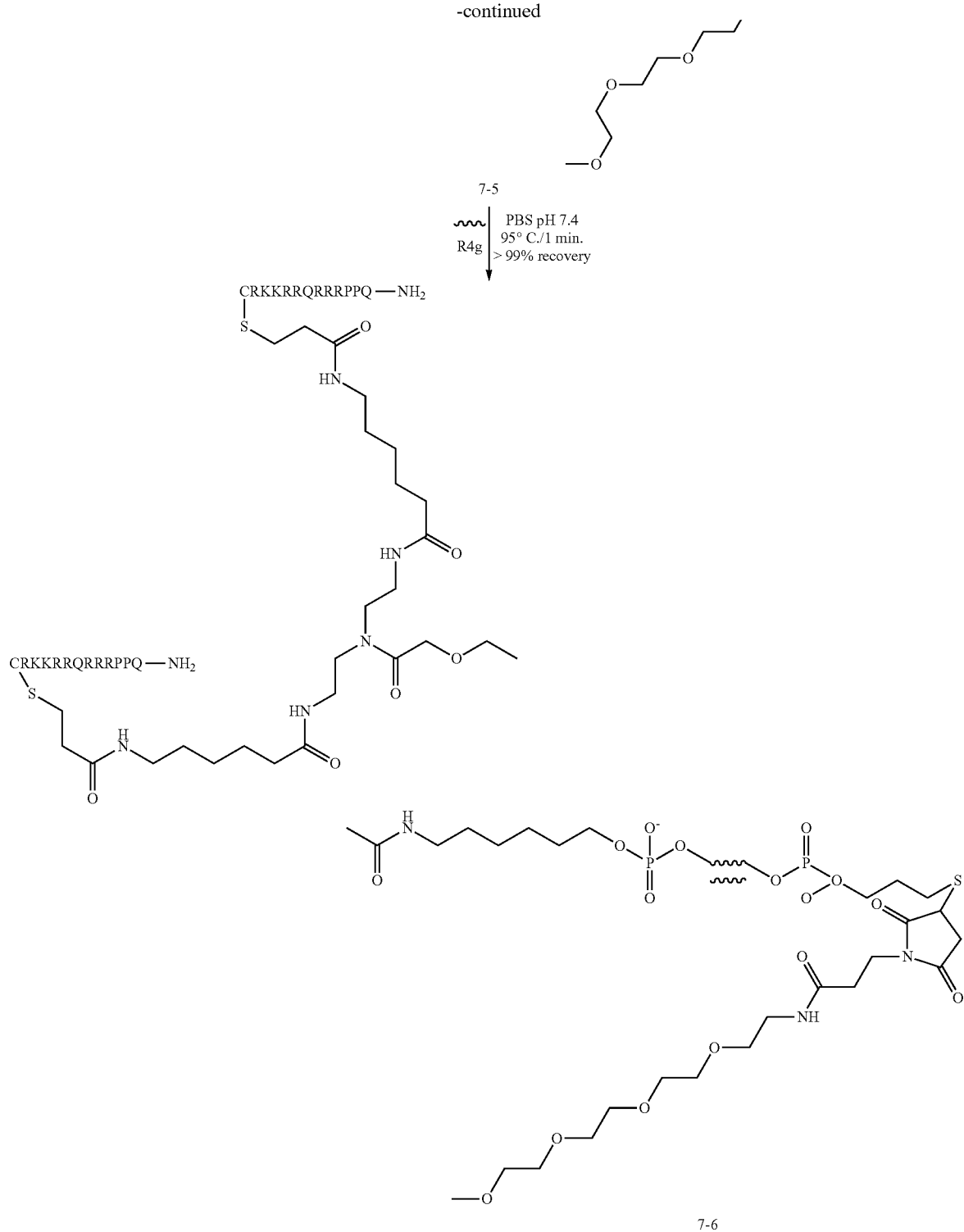

Step 1

A solution of 10 mg (1.54 μmol) R6p in 1.46 mL water was treated with 37.5 μL 2M TEAA, 15 μL (0.015 mmol) 1M DTT in water, and 15 μL (0.108 mmol) TEA. The resulting solution was agitated for 0.5 hr and then desalted using a NAP-25 column eluted with 2.5 mL DI water to give 7-1. Product was taken directly onto next step Step 2

A solution of 7-1 in 2.5 mL DI water from the previous step was treated with 1.8 mg (5.02 μmol) 7-2 added in one portion. The resulting solution was stirred for 10 minutes and then centrifugally dialyzed three times against water using a MW 3000 dialysis membrane. The dialyte was lyophilized to provide 9.55 mg 7-3 as a fluffy white amorphous powder that was taken forward without further purification.

Step 3

A solution of 2.37 mg (2.82 mmol) 4-8 and 1.07 mg (2.82 mmol) HATU in 130 μL DMSO was treated with 0.50 uL (2.82 μmol) DTPEA. After 10 minutes, the resulting solution was added to a solution of 9.55 mg (1.41 mmol) 7-3 and 2.46 μL (0.014 mmol) DIPEA in 530 μL DMSO. The resulting solution was stirred at room temperature for 10 minutes. The crude reaction was centrifugally dialyzed four times against water using a MW 3000 dialysis membrane. The dialyte was lyophilized to provide 10.25 mg oft 7-4 as a fluffy white amorphous powder that was taken forward without further purification.

Step 4

A solution of 5 mg (0.652 μmol) 7-4 in 950 uL 3:1 formamide:water and 50 μL 2M TEAA was treated with a solution of 2.32 mg (1.32 μmol) P6 in 1.0 mL 3:1 formamide:water and the resulting solution stirred at RT for 0.5 h. An additional 1.16 mg (0.652 μmol) 1-4 added to the reaction. The crude reaction was purified by preparatory anion exchange chromatography on a Gilson apparatus using a 6 mL ResourceQ column and a 100:0-0:100% A:B linear gradient (A=20 mM Tris.HCl, 50% formamide, pH 7.4; B=20 mM Tris.HCl, 400 mM NaClO4, 50% formamide, pH 7.4). Suspected product peak was diluted with water, and was centrifugally dialyzed four times against water using a MW 3000 dialysis membrane. The dialyte was lyophilized to provide 2.77 mg of the desired conjugate 7-5. Measured mass=10976

Step 5

A slurry of 1 mg (0.092 μmol) 7-5 in 100 μL pH 7.4 PBS was treated with a solution of 0.5 mg (0.074 mmol) of R4g in 100 μL pH 7.4 PBS added in one portion. The resulting slurry was heated to 95° C. and allowed to cool to room temperature. The resulting solution was cooled and was centrifugally dialyzed three times against water using a MW 3000 dialysis membrane. The dialyte was lyophilized to provide 1.5 mg of the desired duplex product 7-6 as a fluffy white amorphous powder. Duplex was confirmed by MS, measured mass=17711.

In a manner similar to that described above for the synthesis of 7-6 were prepared the following compounds:

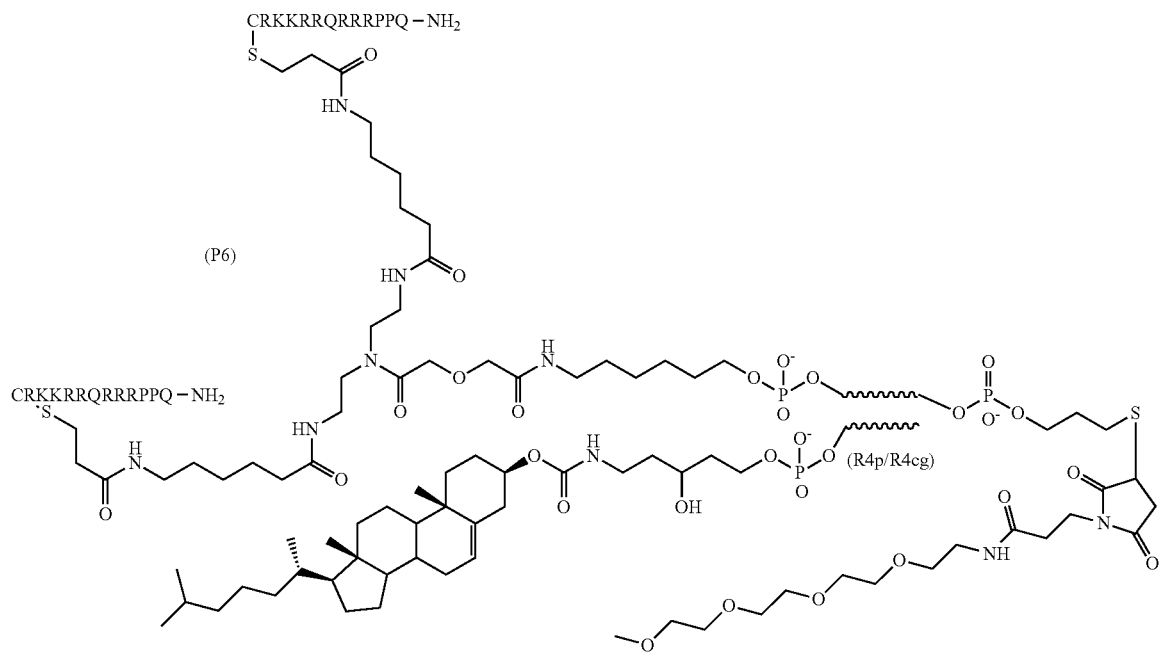

7-7

Measured mass = duplex 18305

7-8
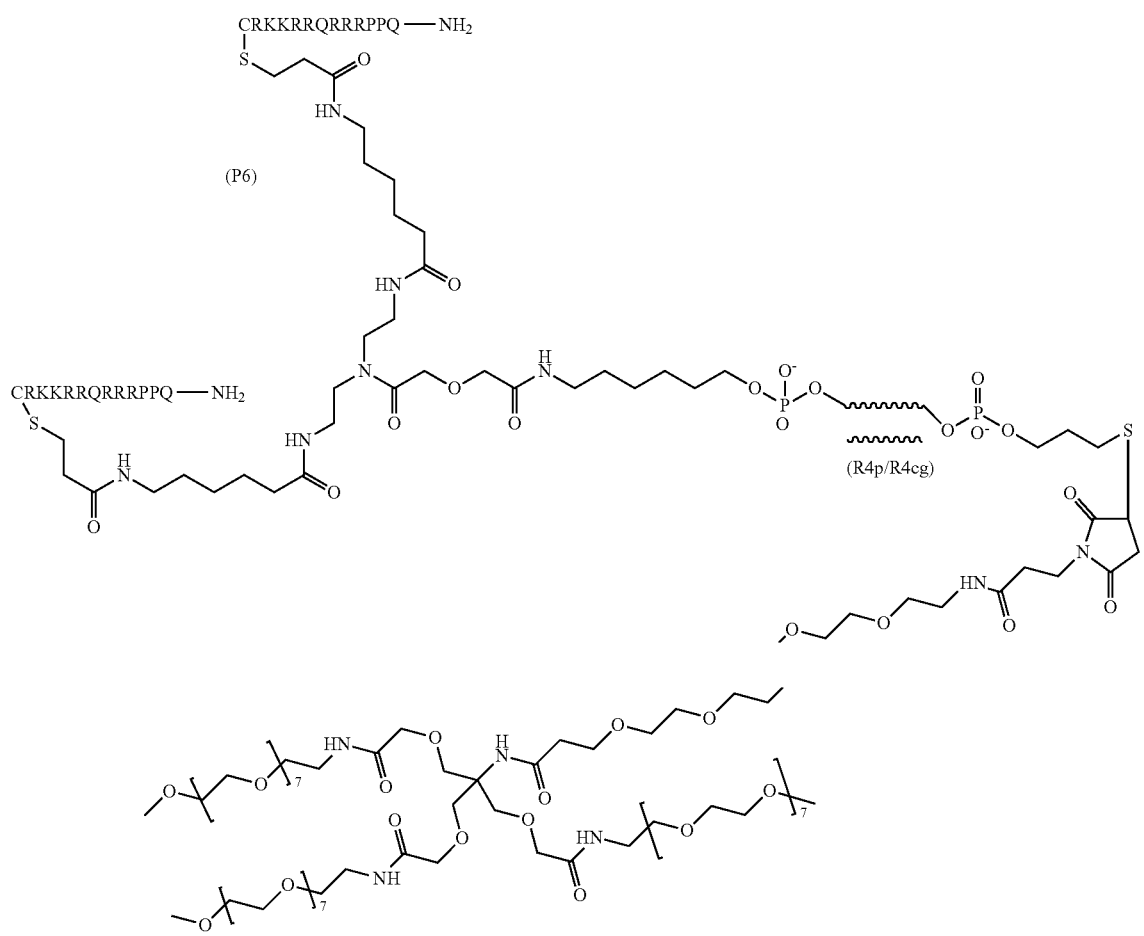
Measured mass = duplex 19183
7-9
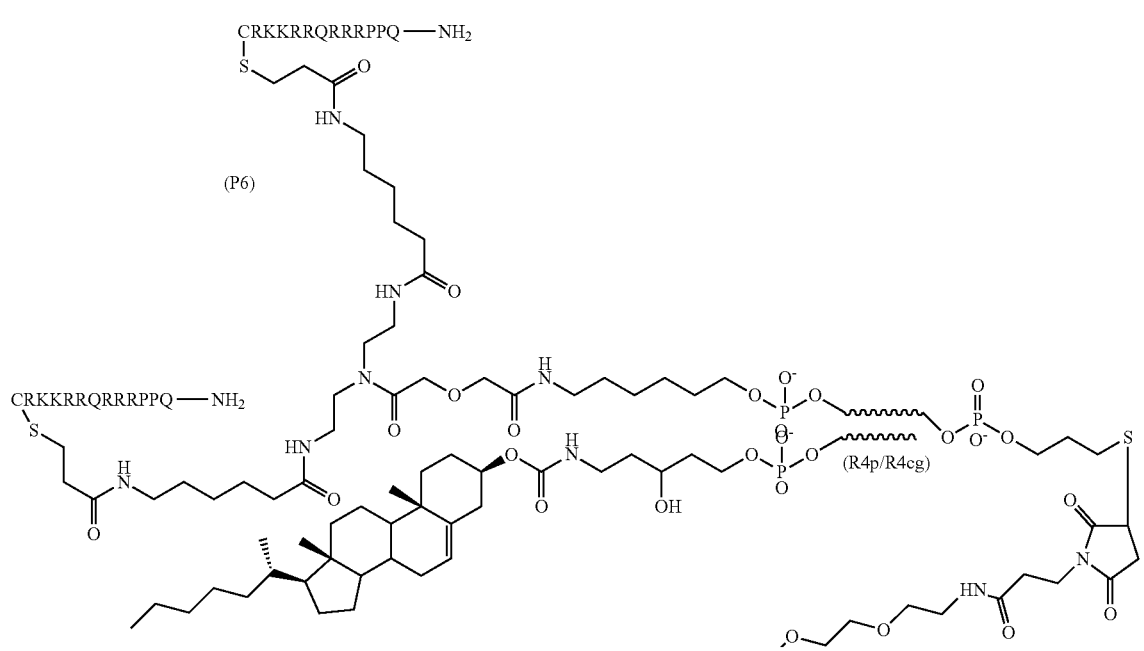

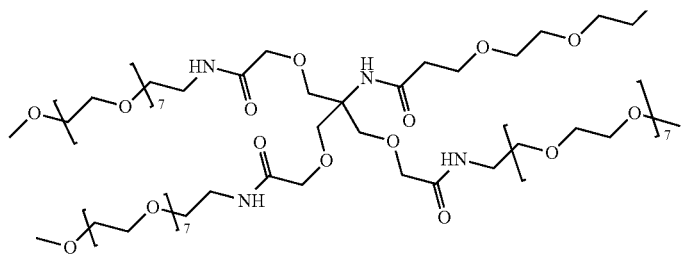
Measured mass = duplex 19777
7-10
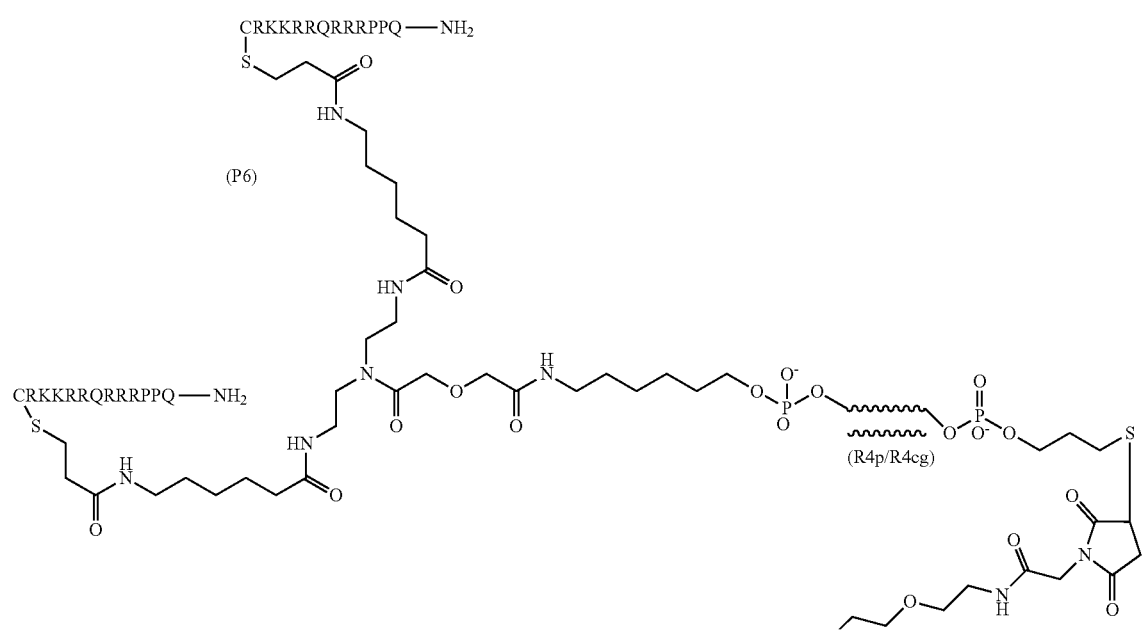
Measured mass = duplex 17886

7-11
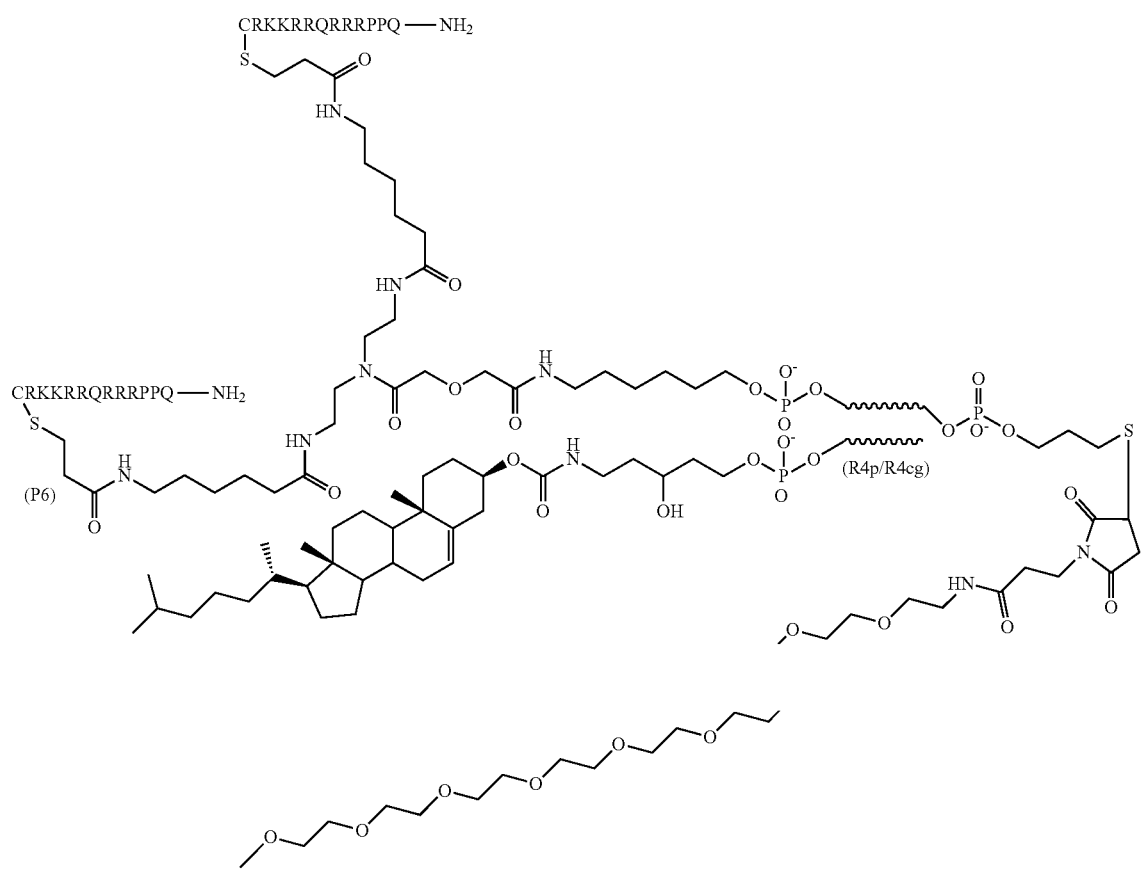
Measured mass = duplex 18480
Example 8
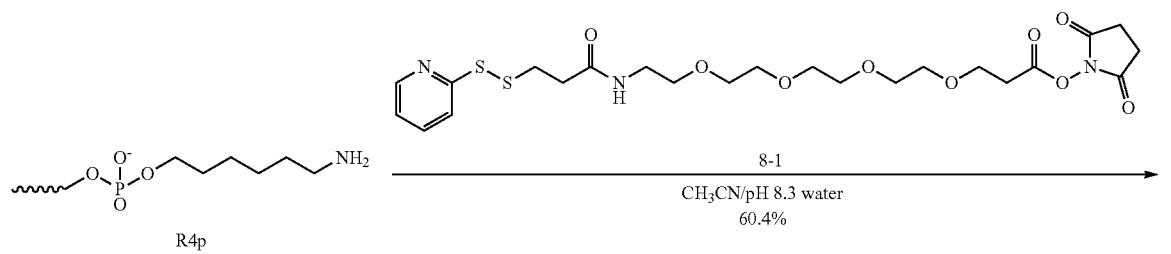
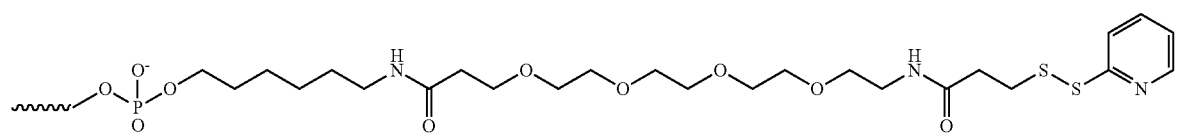

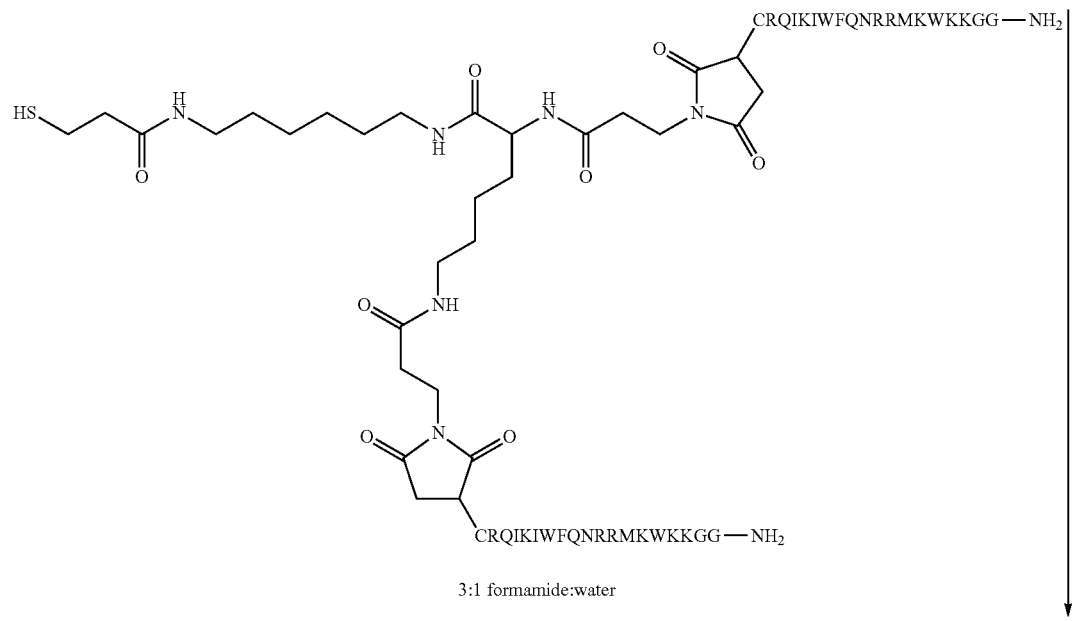
3:1 formamide:water
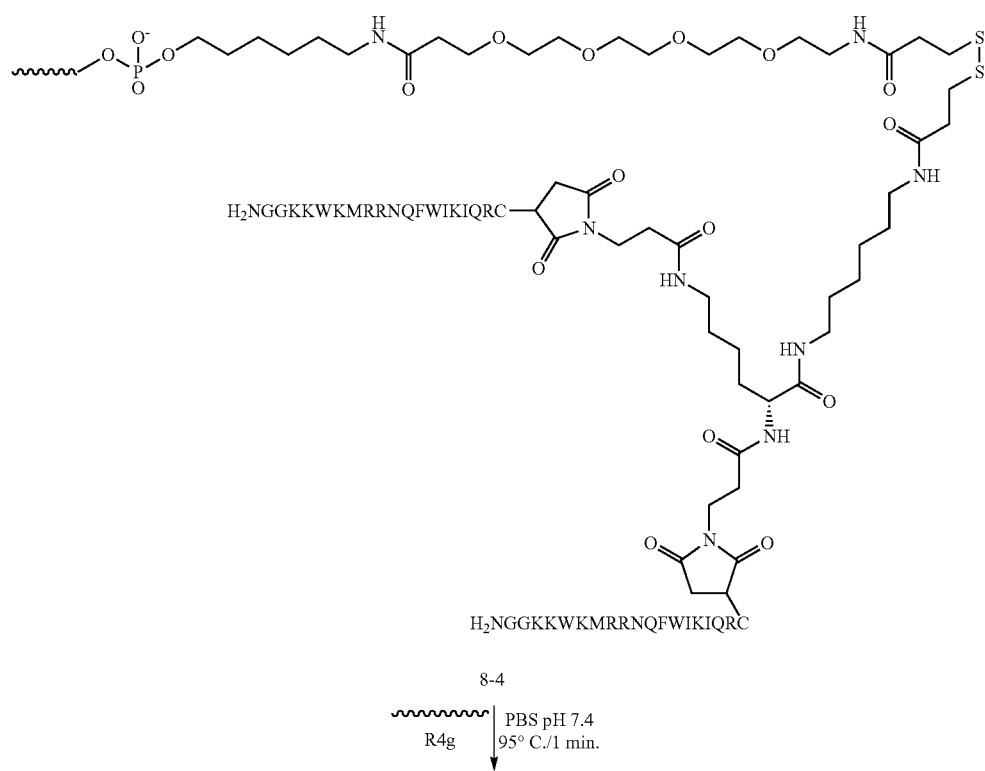
8-4
R4g | PBS pH 7.4
95° C./1 min.

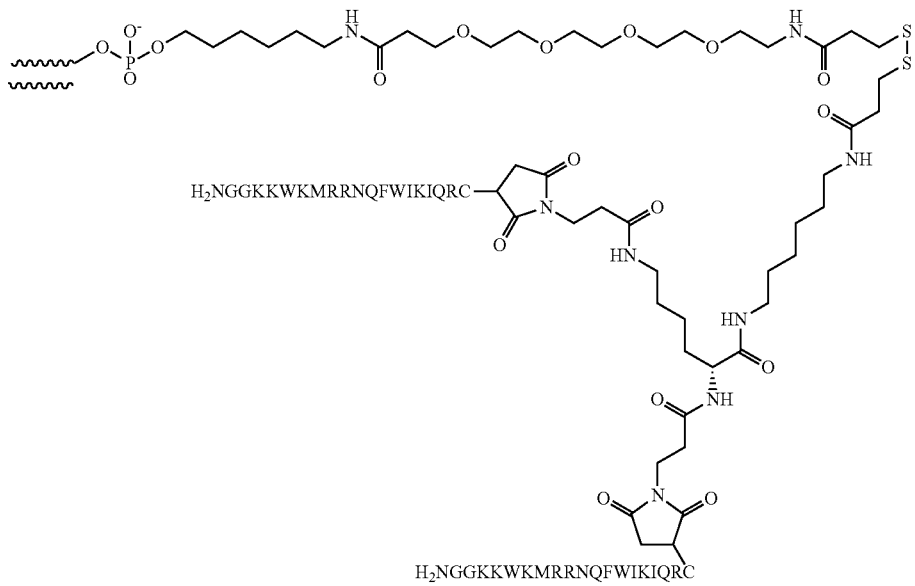

8-5

Step 1

A solution of 50 mg (7.89 µmol) R4p in 3.6 mL pH 8.3 water was treated with a solution of 30.9 mg (0.055 mmol) 8-1 in 400 uL acetonitrile. The resulting solution was stirred for 10 minutes. The crude reaction was purified reverse phase prep LC on a Gilson apparatus using a Waters phenyl Xbridge column (95:5-5:95% A:B linear gradient [A=water with 250 mM TEAA, B=acetonitrile with 250 mM TEAA]). Suspected product peak was diluted with water, and was centrifugally dialyzed four times against water using a MW 3000 dialysis membrane. The dialyte was lyophilized to provide 32.3 mg of the desired conjugate 8-2 as a fluffy white amorphous powder, measured mass=6778.

Step 2

A solution of 5 mg (0.709 µmol) 8-2 in 950 µL 3:1 formamide:water and 150 µL 2M TEAA was treated with a solution of 8.201 mg (1.475 µmol) 8-3 (synthesized in a manner identical to that described in Example 6, Steps 1 and 2) in 1.0 mL 3:1 formamide:water and the resulting solution stirred at RT for 0.5 h. The crude reaction was purified by preparatory anion exchange chromatography on a Gilson apparatus using a 6 mL ResourceQ column and a 100:0-0:100% A:B linear gradient (A=20 mM Tris.HCl, 50% formamide, pH 7.4; B=20 mM Tris.HCl, 400 mM NaClO4, 50% formamide, pH 7.4) Suspected product peak was diluted with water, and was centrifugally dialyzed four times against water using a MW 3000 dialysis membrane. The dialyte was lyophilized to provide the desired conjugate 8-4 as an amorphous solid that was taken directly onto the next step.

Step 3

A slurry of 8-4 in pH 7.4 PBS was treated with a solution of 1.25 mg (0.186 µmol) of R4g added in one portion. The resulting slurry was heated to 95° C. and allowed to cool to room temperature. The resulting solution was cooled and was centrifugally dialyzed three times against water using a MW 3000 dialysis membrane. The dialyte was lyophilized to provide 3.68 mg of the desired duplex product 8-5 as a fluffy white amorphous powder. Duplex was confirmed by MS, measured mass=passenger strand 12230, guide strand 6733.

In a manner similar to that described above for the synthesis of 8-5 were prepared the following compounds:

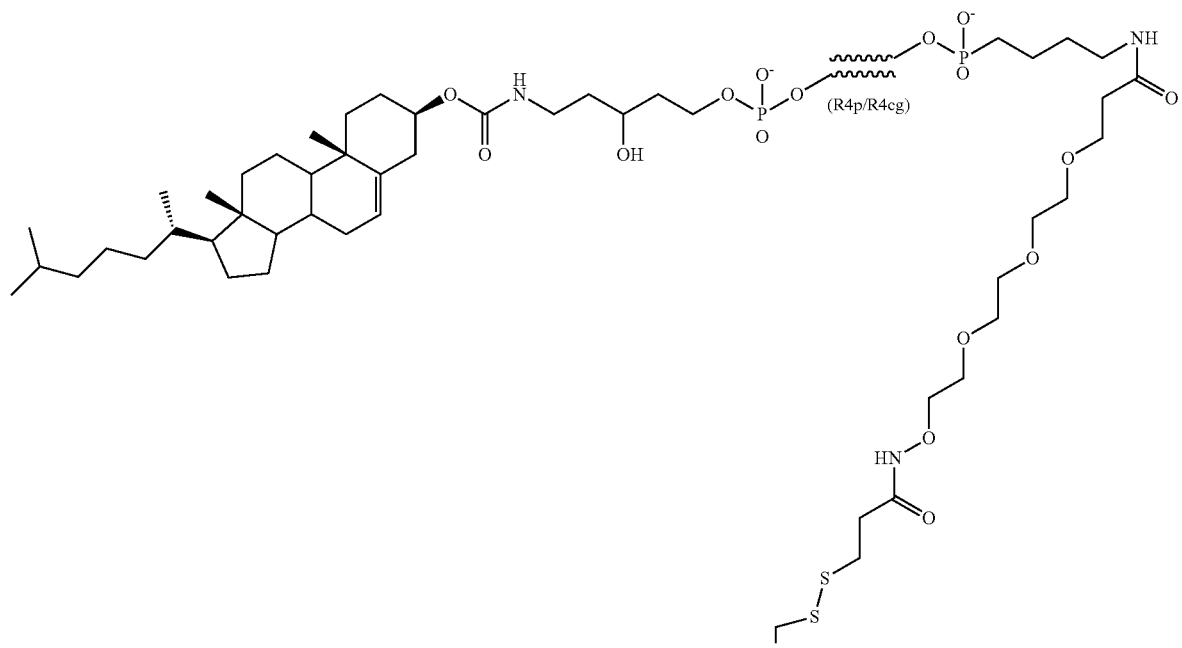
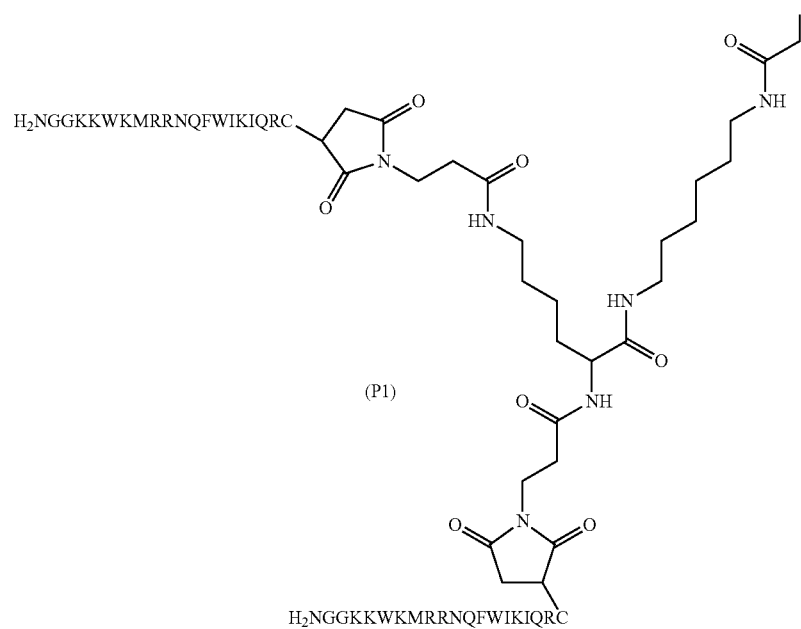
Measured mass = 19558 duplex

-continued
8-7
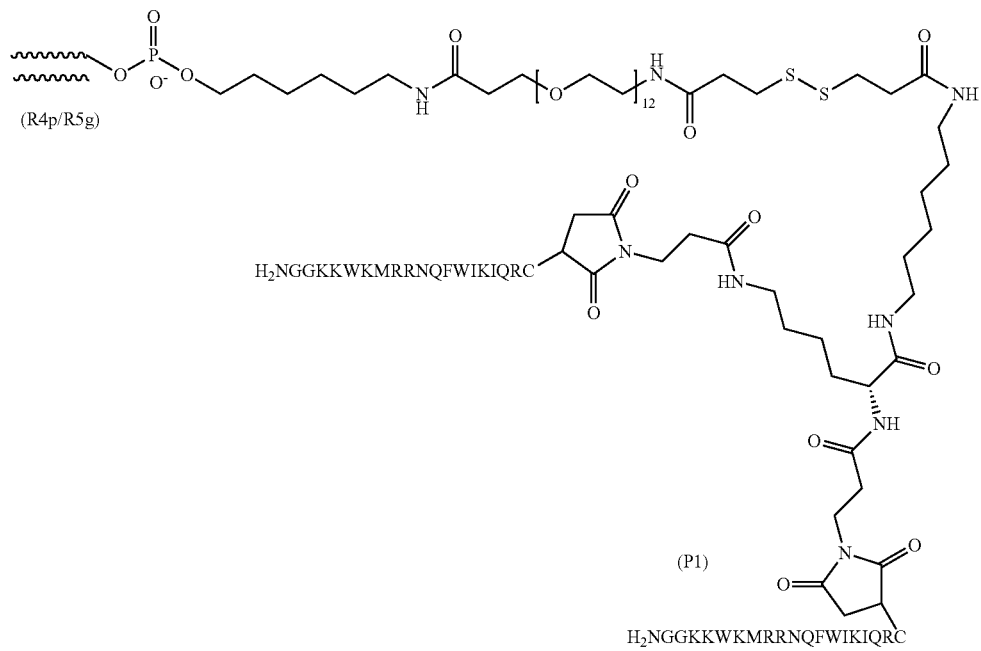
(P1)
Measured mass = 19312 duplex
8-8
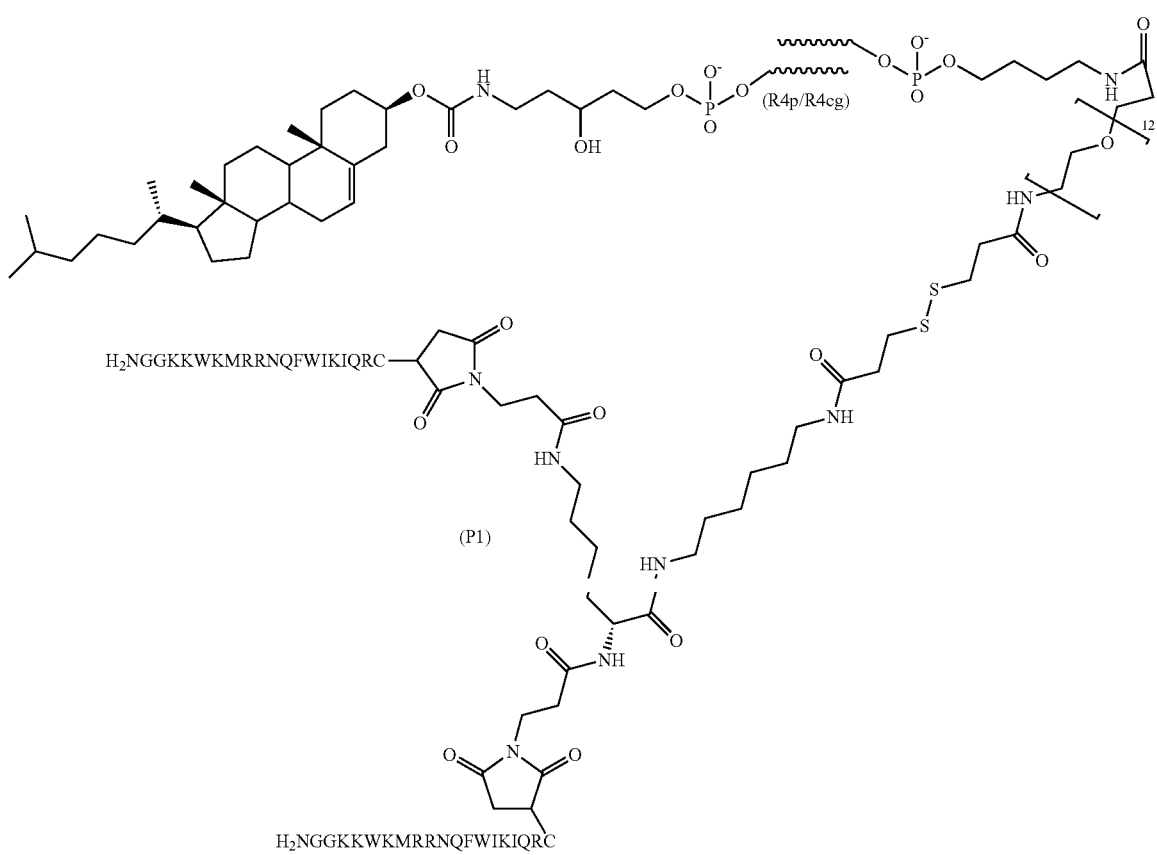
(P1)
Measured mass = 19911 duplex

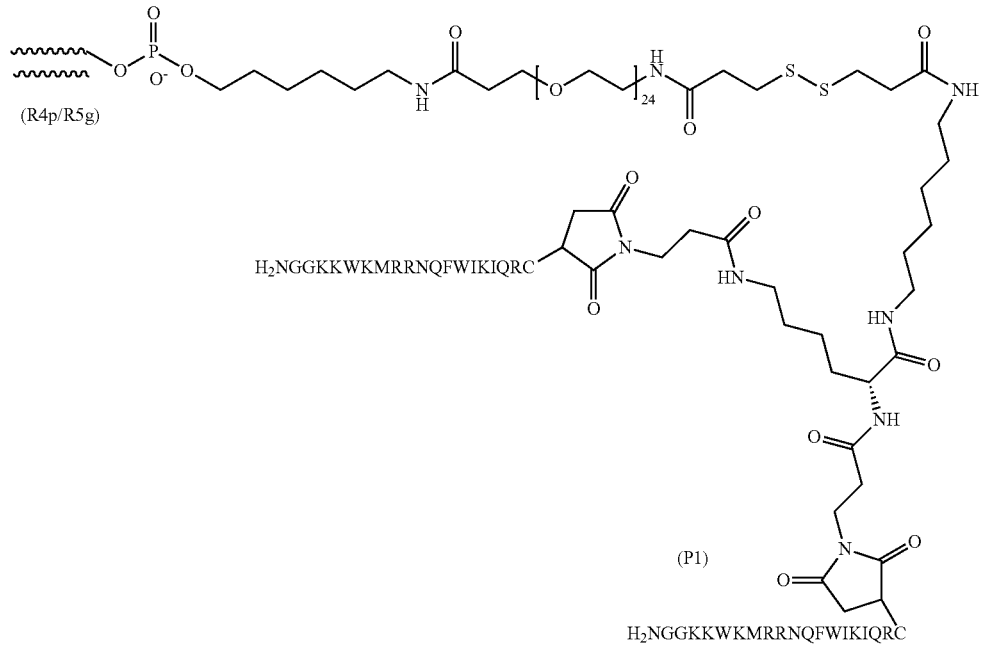
Measured mass = 19845 duplex
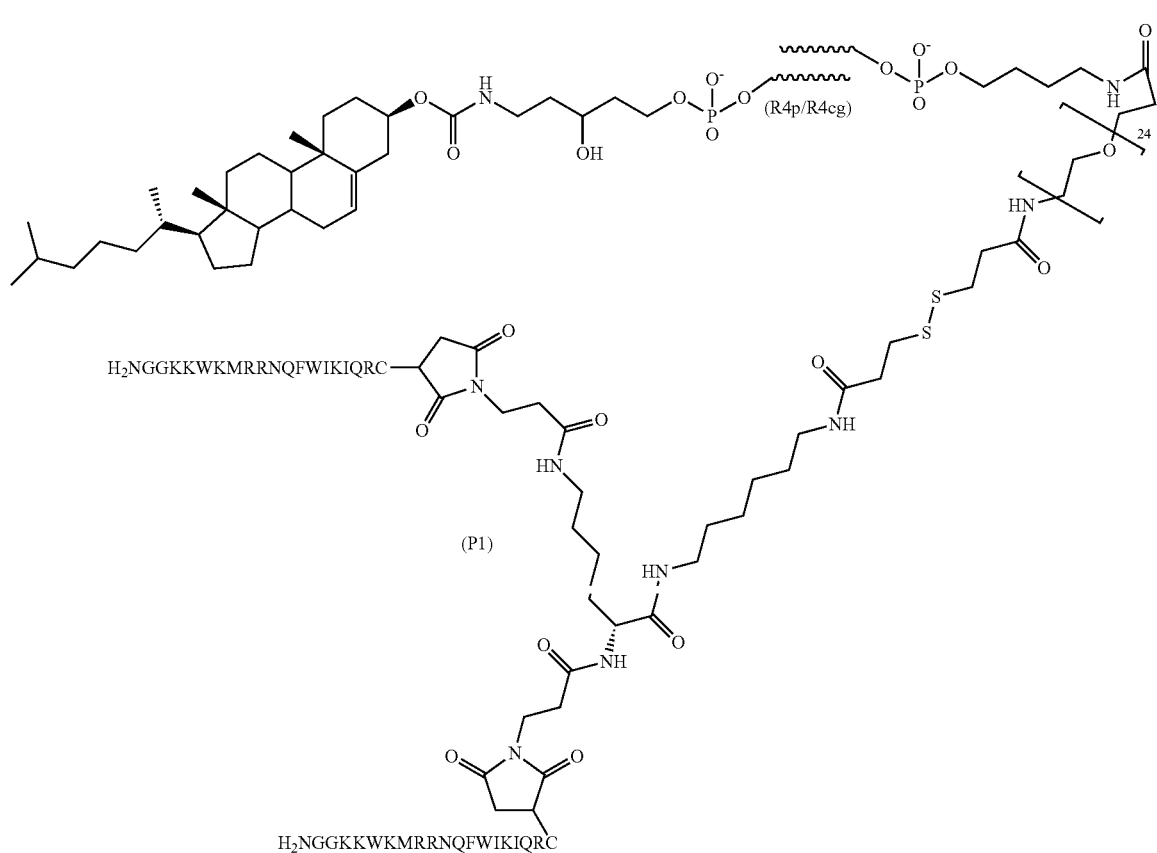
Measured mass = 20439 duplex

Example 9
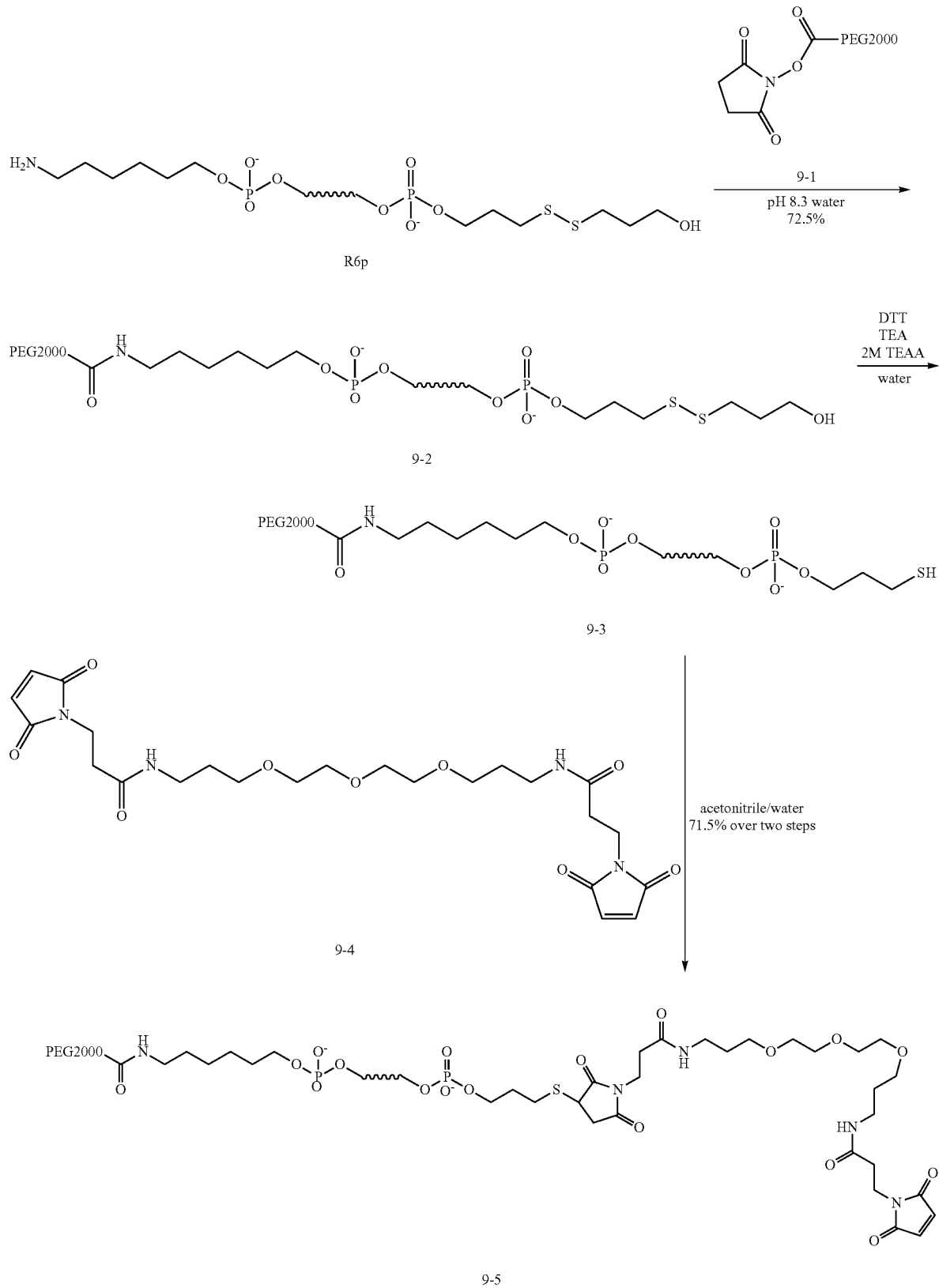

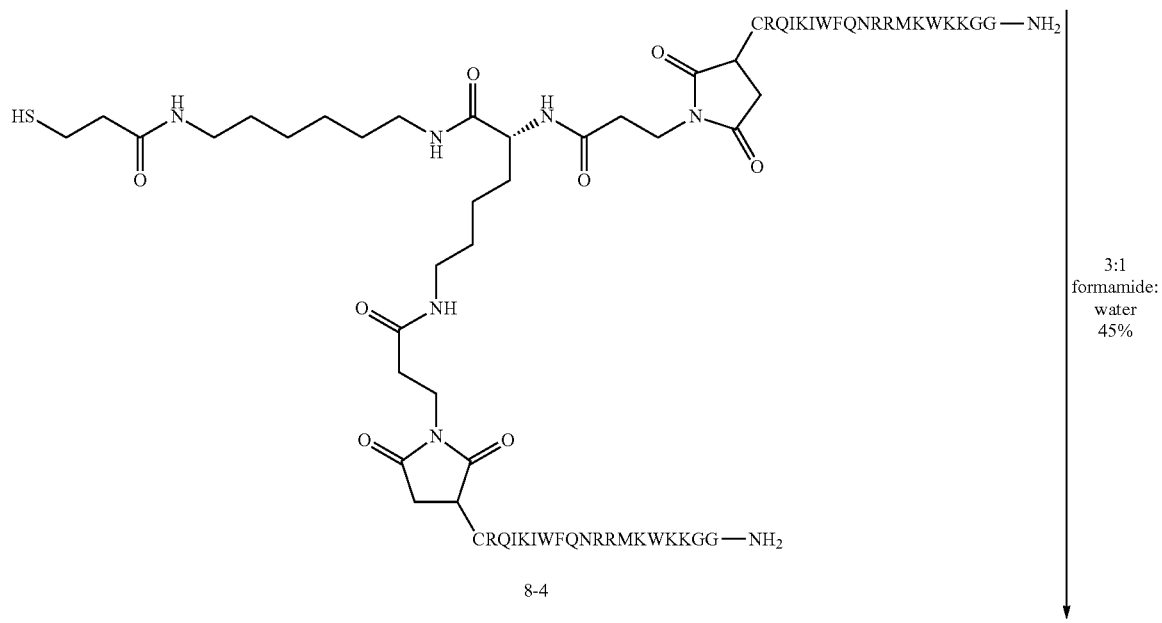
8-4
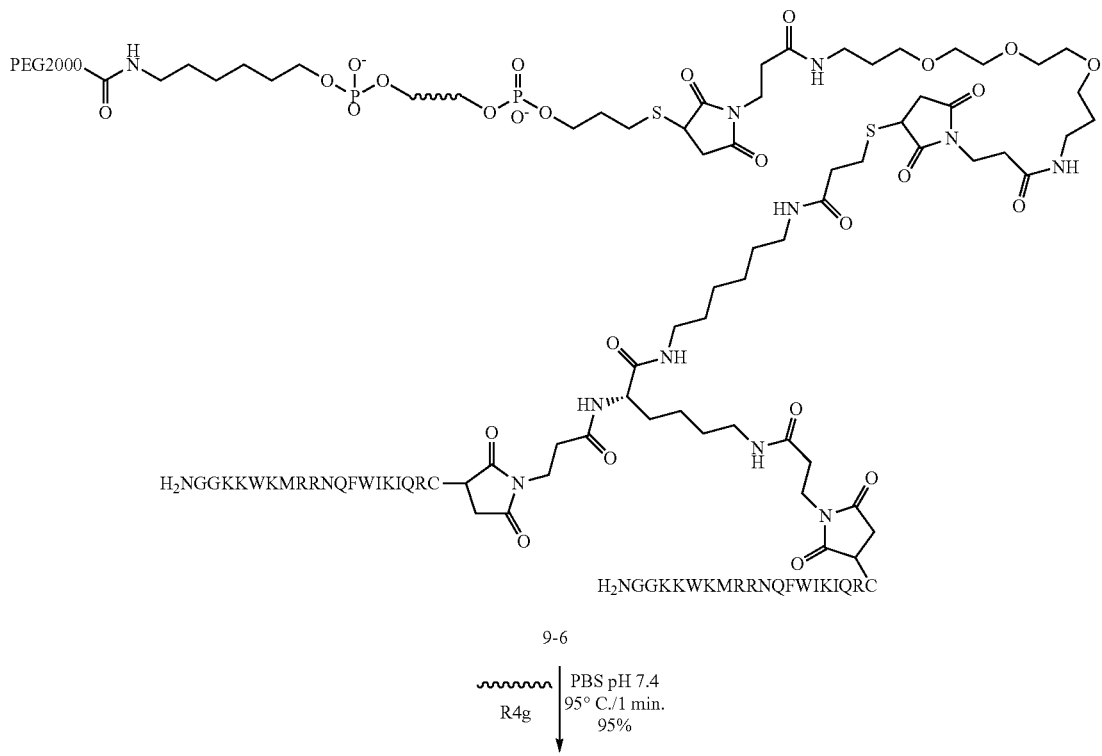
9-6

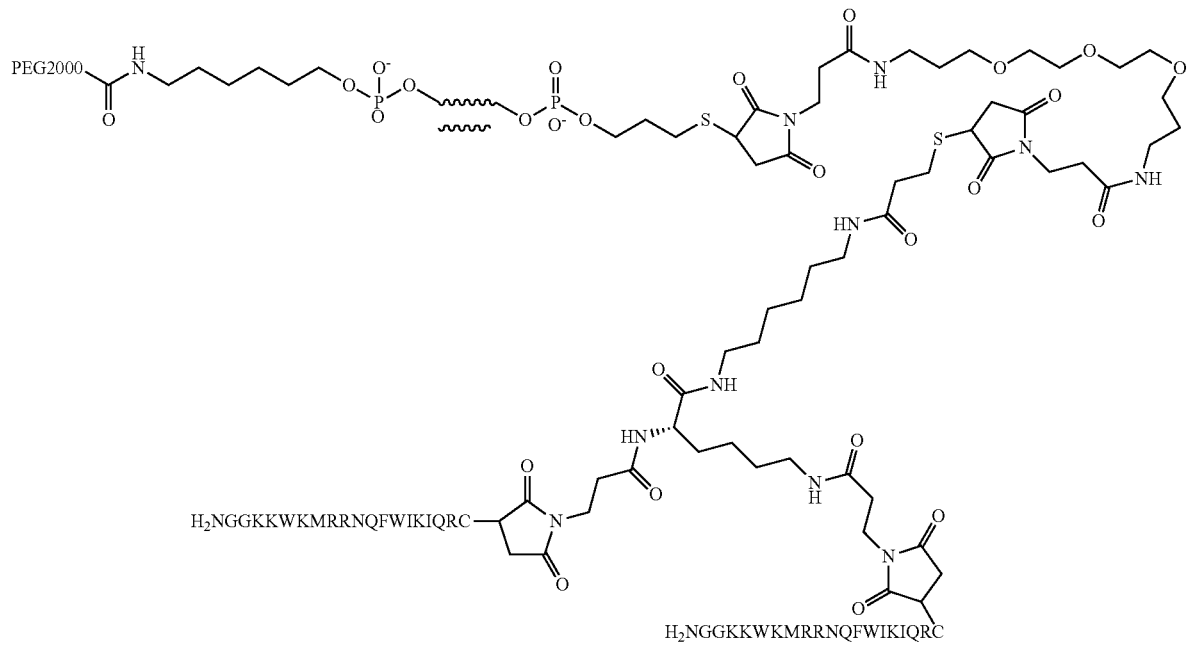

9-7

Step 1

A solution of 50 mg (7.69 μmol) R6p in 4 mL pH 8.3 water was treated with 108 mg (0.054 mmol) 9-1 added in one portion. The resulting solution was stirred for 10 minutes. The crude reaction was purified reverse phase prep LC on a Gilson apparatus using a Waters phenyl Xbridge column (95:5-5:95% A:B linear gradient [A=water with 250 mM TEAA, B=acetonitrile with 250 mM TEAA]). Suspected product peak was diluted with water, and was centrifugally dialyzed four times against water using a MW 3000 dialysis membrane. The dialyte was lyophilized to provide 47.39 mg of the desired conjugate 9-2 as a fluffy white amorphous powder, measured mass distribution around 8400.

Step 2

A solution of 51 mg (6 μmol) 9-2 in 5.85 mL water was treated with 150 μL 2M TEAA, 60 μL (0.060 mmol) 1M DTT in water, and 60 μL (0.430 mmol) TEA. The resulting solution was agitated for 0.5 hr and then desalted using three NAP-25 column eluted with 3.0 mL DI water each to give 9-3. Product was taken directly onto next step.

Step 3

A solution of 8.89 mg (0.017 mmol) 9-4 in 9 mL acetonitrile was treated with a solution of 9-3 in 4.5 mL DI water from the previous step added dropwise. The resulting solution was stirred for 15 minutes and then centrifugally dialyzed three times against water using a MW 3000 dialysis membrane. The dialyte was lyophilized to provide 19.07 mg 9-5 as a fluffy white amorphous powder that was taken forward without further purification.

Step 4

A solution of 5 mg (0.562 pawl) 9-5 in 950 μL 3:1 formamide:water and 150 μL 2M TEAA was treated with a solution of 6.25 mg (1.123 μmol) 8-3 in 1.0 mL 3:1 formamide:water and the resulting solution stirred at RT for 0.5 h. The crude reaction was purified by preparatory anion exchange chromatography on a Gilson apparatus using a 6 mL ResourceQ column and a 100:0-0:100% A:B linear gradient (A=20 mM Tris.HCl, 50% formamide, pH 7.4; B=20 mM Tris.HCl, 400 mM NaClO4, 50% formamide, pH 7.4) Suspected product peak was diluted with water, and was centrifugally dialyzed four times against water using a MW 3000 dialysis membrane. The dialyte was lyophilized to provide 3.6 mg of the desired conjugate 9-6 as an amorphous solid.

Step 5

A solution of 1.58 mg (0.109 μmol) 9-6 in pH 7.4 PBS was treated with a solution of 0.882 mg (0.131 μmol) of R4g added in one portion. The resulting solution was heated to 95° C. and allowed to cool to room temperature. The resulting solution was cooled and was centrifugally dialyzed three times against water using a MW 3000 dialysis membrane. The dialyte was lyophilized to provide 2.35 mg of the desired duplex product 9-7 as a fluffy white amorphous powder. Duplex was confirmed by MS, measured mass=passenger strand distribution around 14.5 kD, guide strand 6732.

In a manner similar to that described above for the synthesis of 9-7 were prepared the following compounds:

9-8
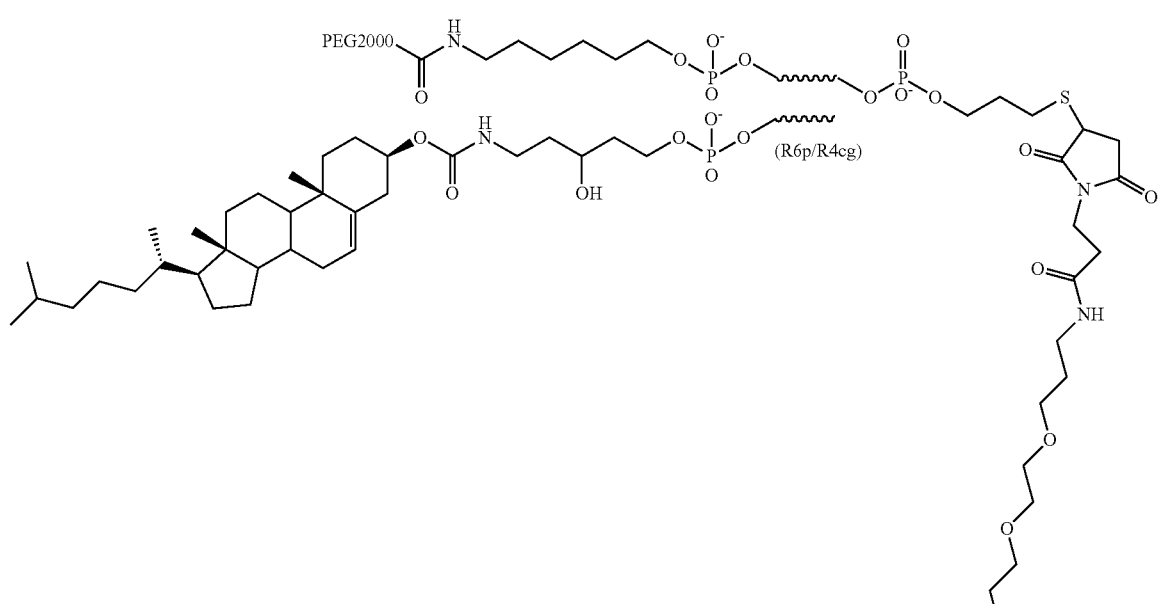
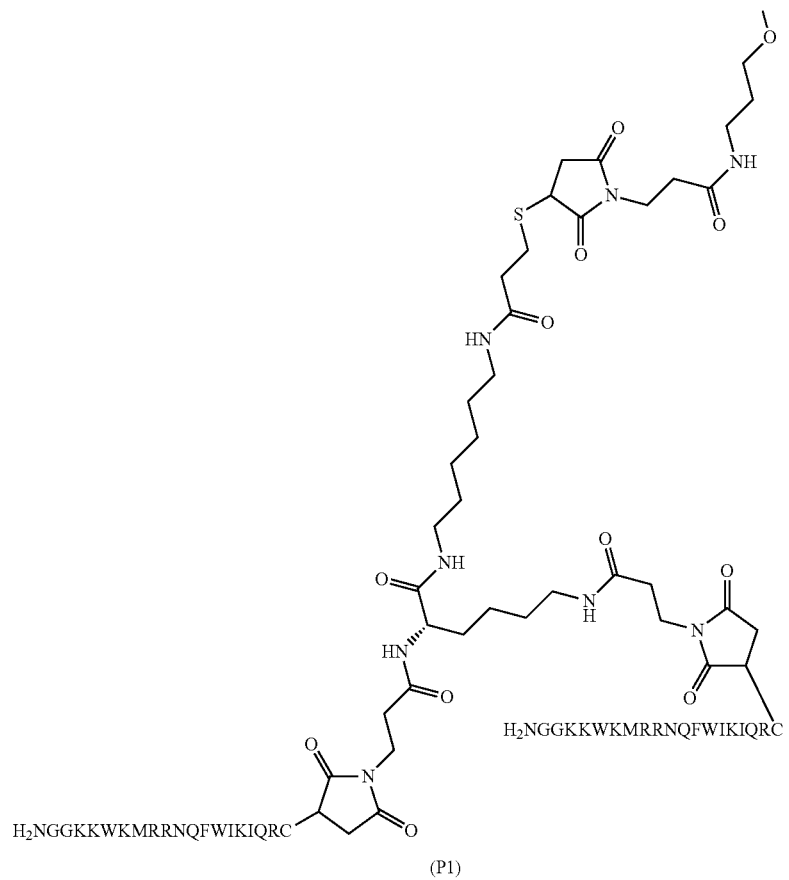
(P1)
Measured mass = ~ 21.8 kDa duplex

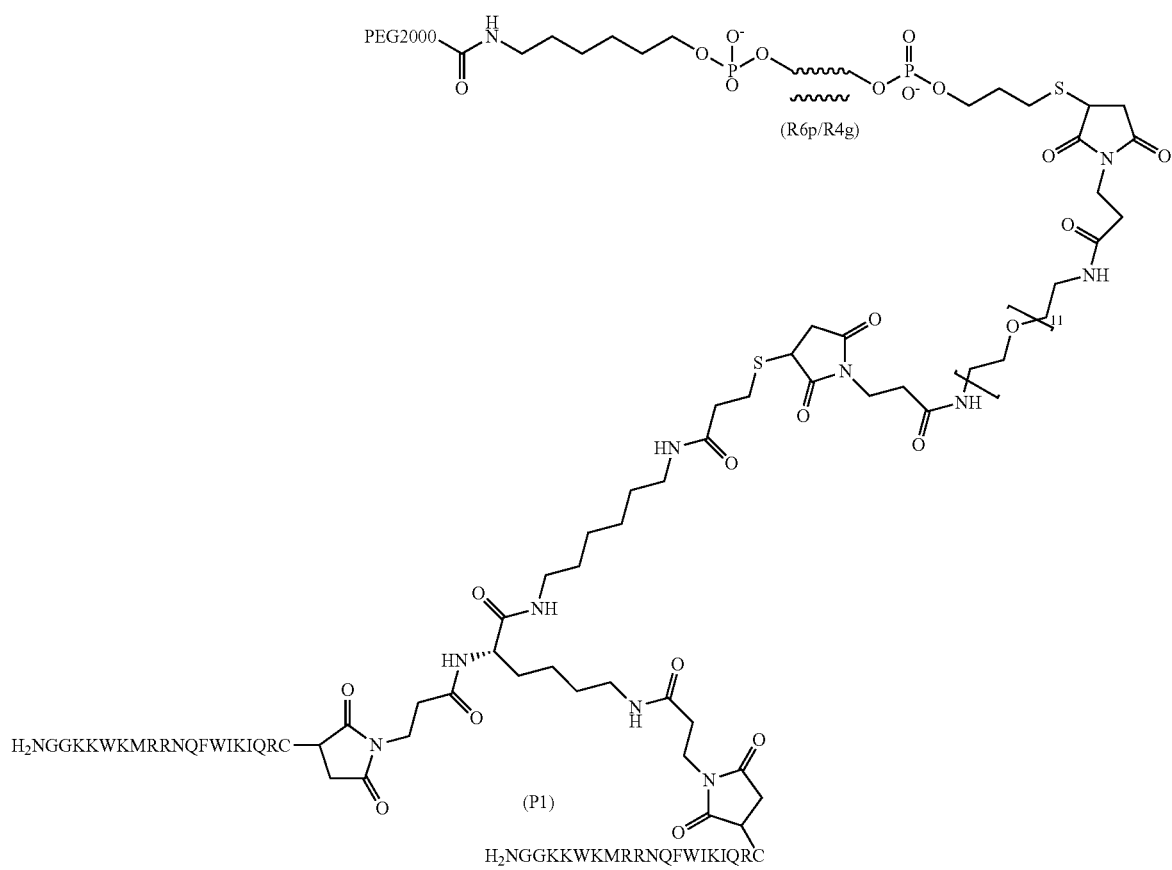
Measured mass = ~ 21.8 kDa duplex

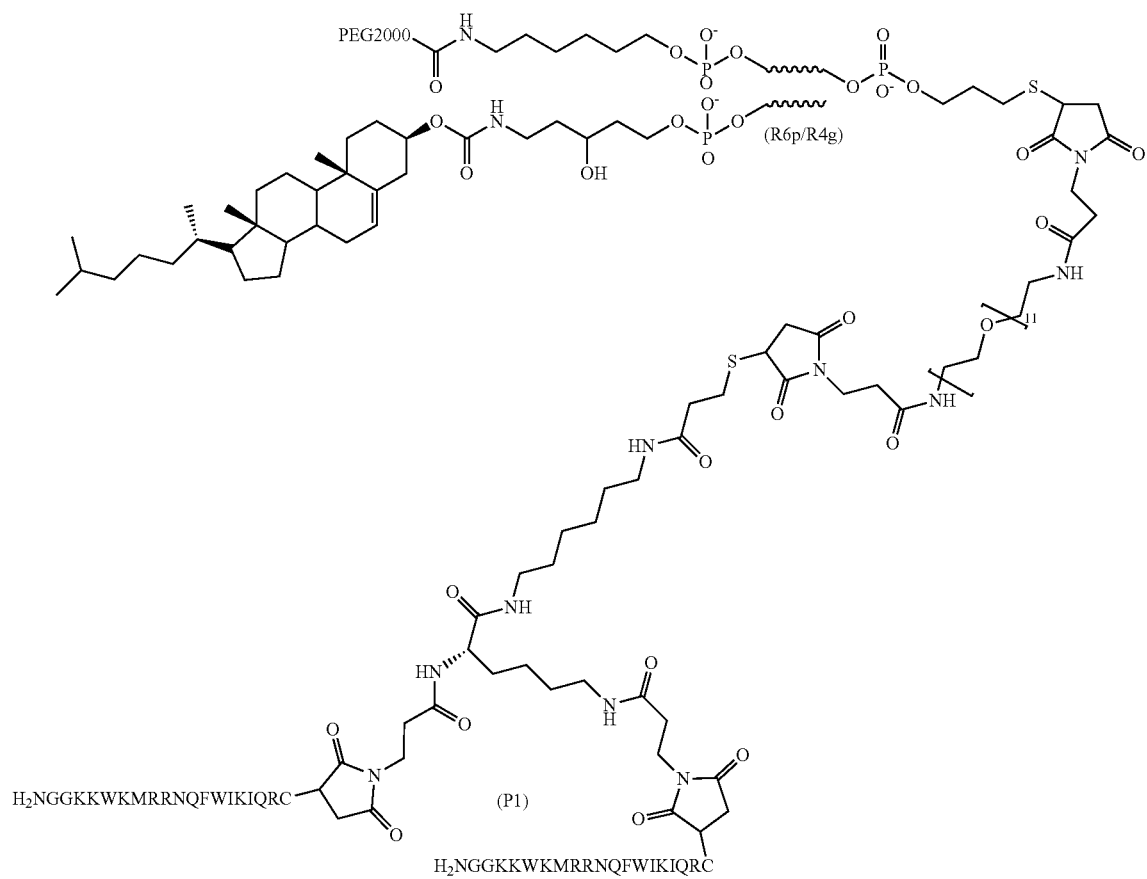
Measured mass = ~ 22.1 kDa duplex
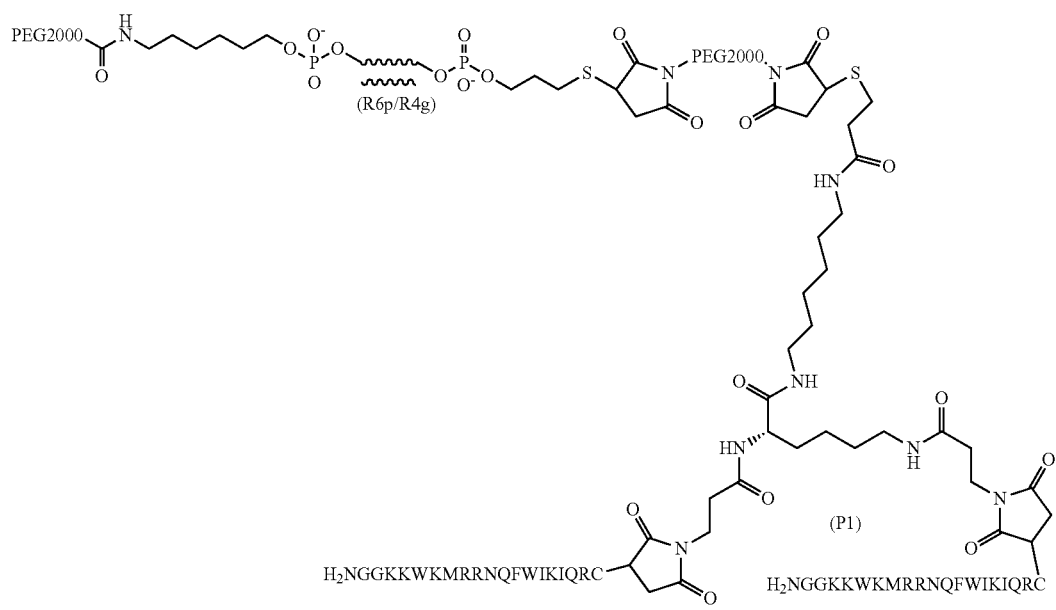
Measured mass = ~ 22.7 kDa duplex -continued
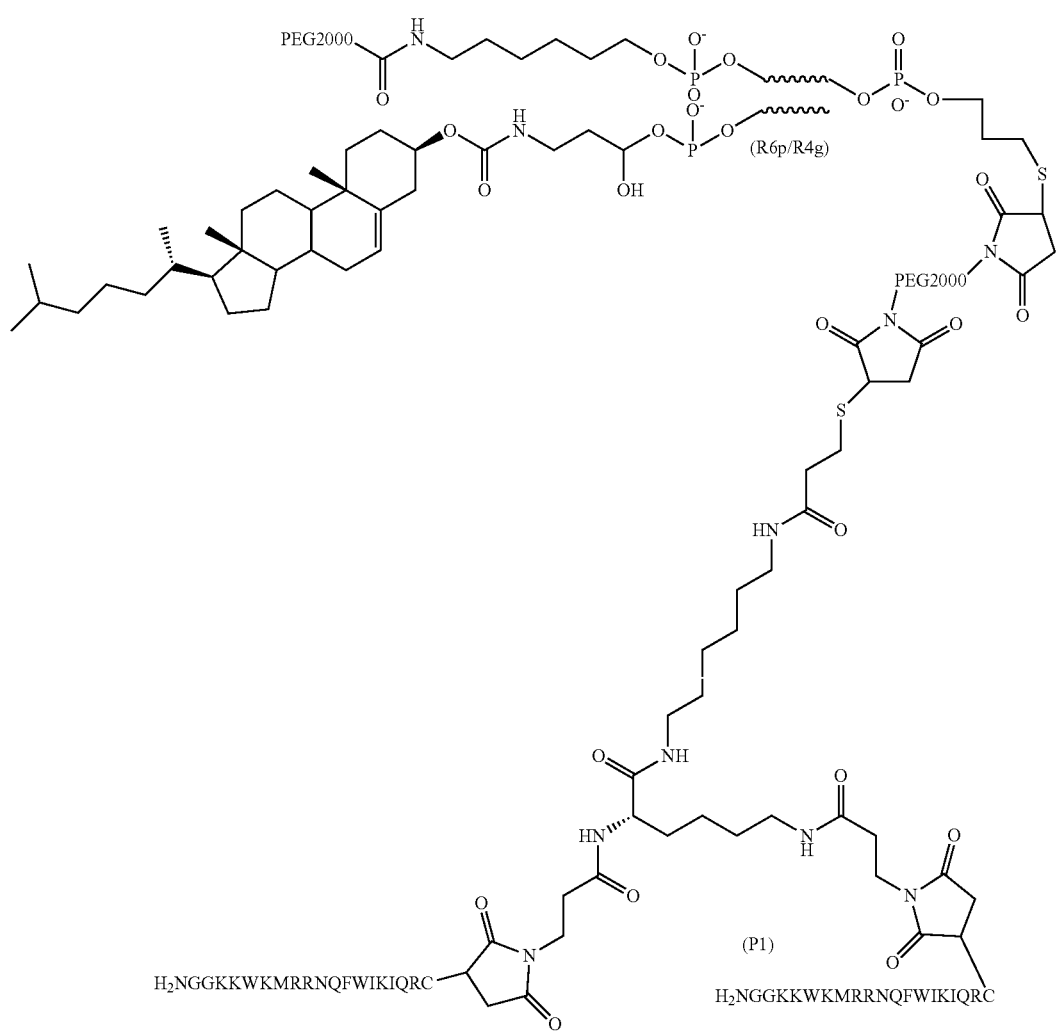
9-12
Measured mass = ~ 23.3 kDa duplex
Example 10
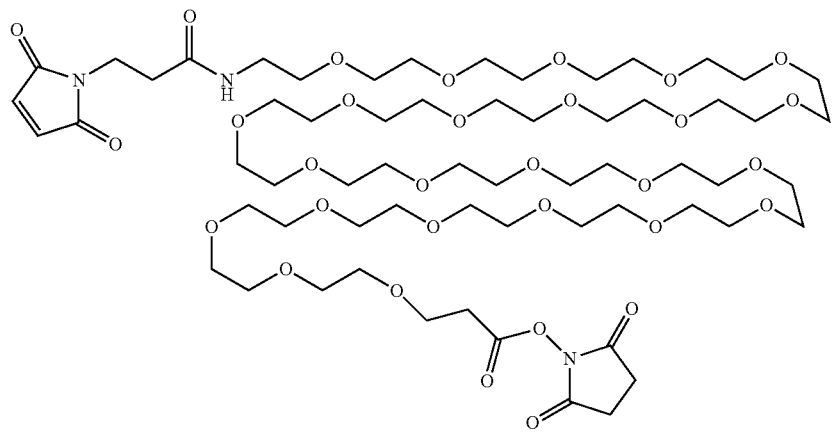
10-1

-continued
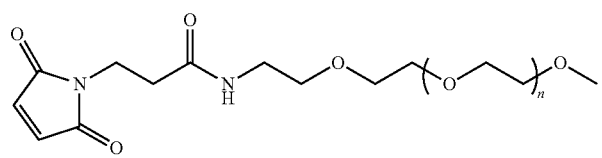
10-2
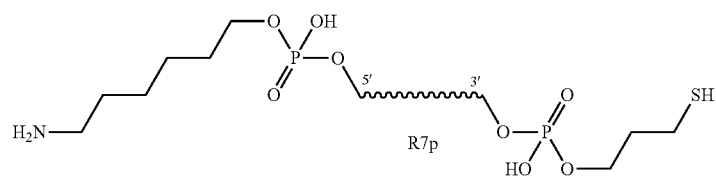
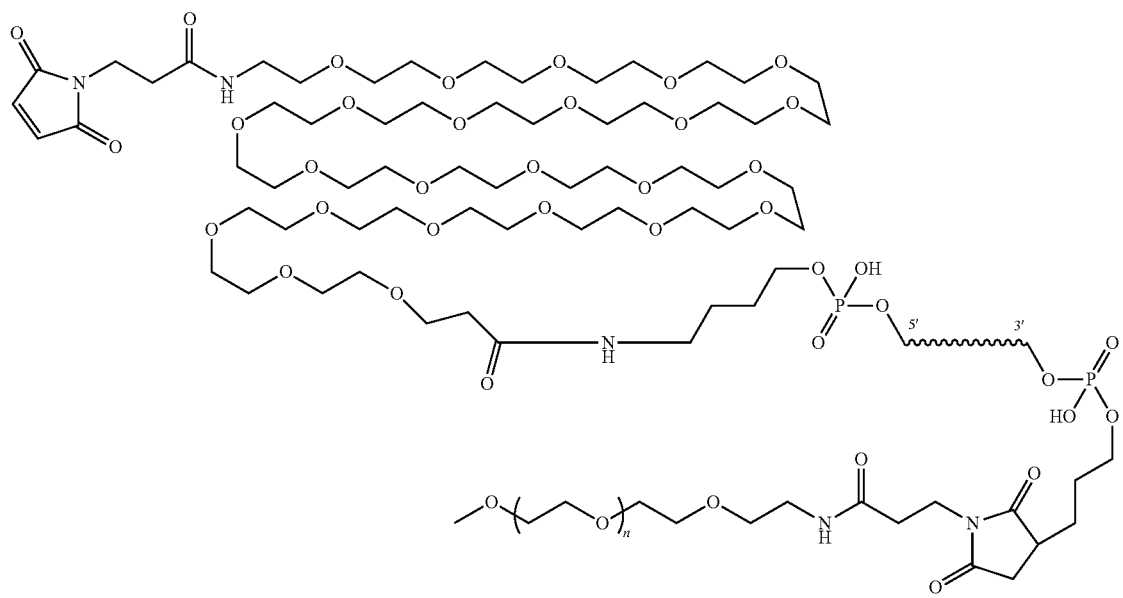
10-3
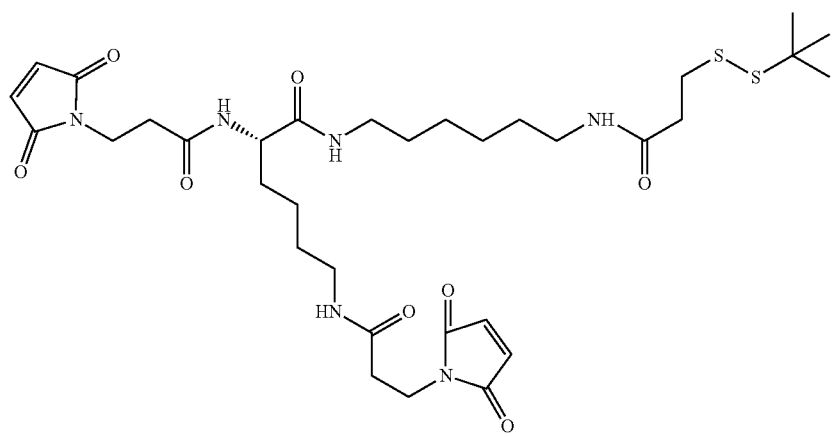
6-5'
1. Formamide/Water = 3/1
   2.5% v/v TEAA, P7
2. 10 eq. TCEP•HCl

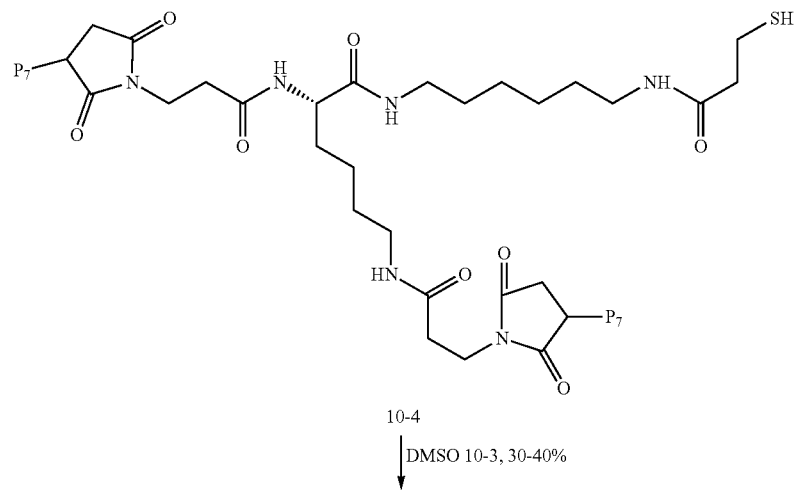
10-4
↓ DMSO 10-3, 30-40%
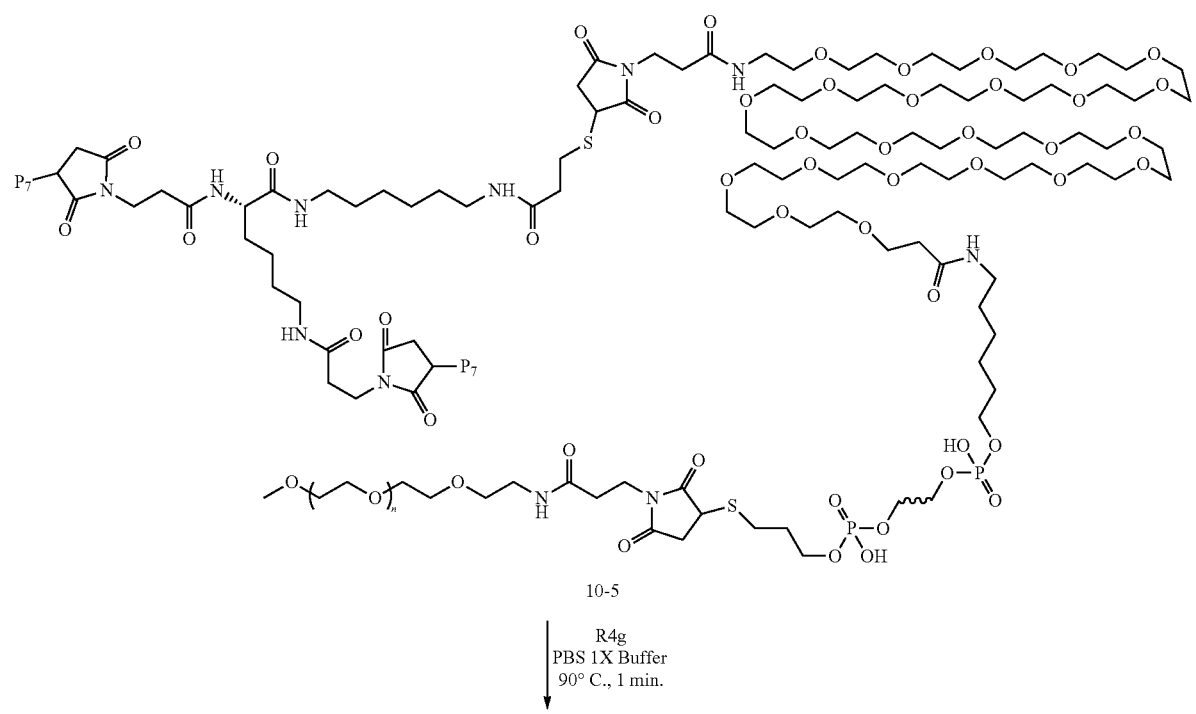
10-5
↓ R4g
PBS 1X Buffer
90° C., 1 min.

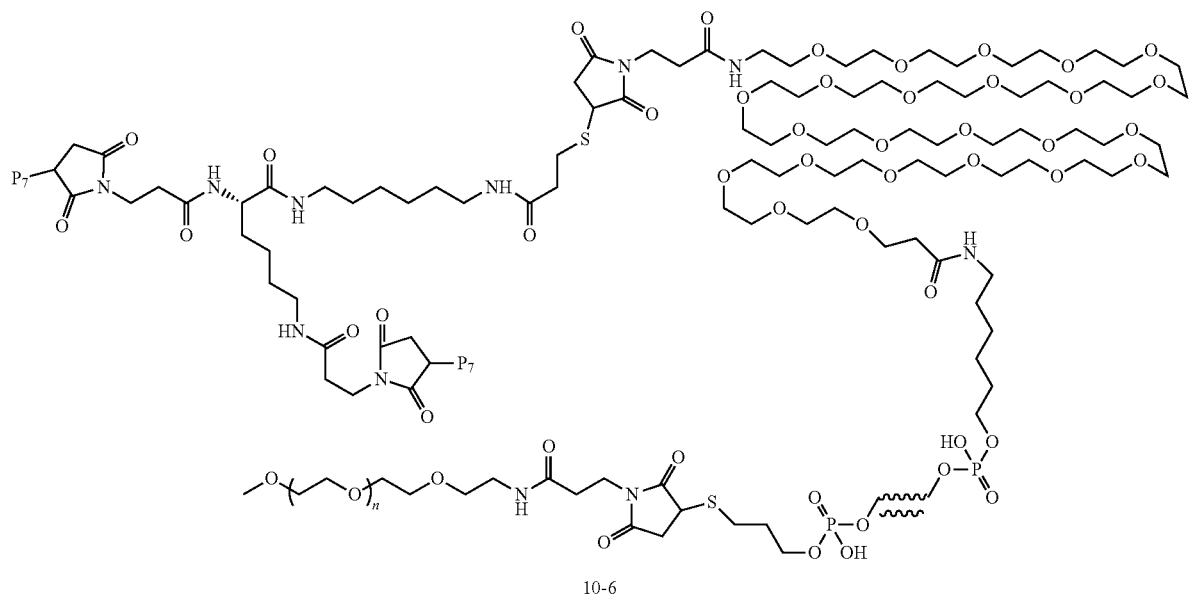

10-6

Step 1

To a solution of R7p (10.0 mg, 1.54 μmol) in 0.5 mL Tris.HCl buffer (pH=8.0) was added polydispersed PEG1000-Mal 10-2 (3.08 mg, 3.08 μmol) in 0.5 mL MeCN at room temperature and the resulting reaction mixture was stirred for 15 min. Upon LC-MS analysis indicated complete consumption of the starting R7p, SMPEG24 10-1 (10.8 mg, 7.71 μmol) in 0.5 mL MeCN was added and the reaction mixture was stirred for additional 2 h. The reaction was quenched by addition of water and centrifugally dialyzed 5 times against water with MW 3000 cutoff membrane. The dialyte was lyophilized to provide crude 10-3 as a white solid and was used for the next step without further purification, MS-9000 with polydispersed PEG unit.

Step 2

A solution of 6-5' (1.70 mg, 2.35 mmol) in 500 μl of formamide/H₂O/2 M TEAA=3/1/0.1 was treated with a solution of peptide P7 (19.6 mg, 5.17 μmol) in 500 μl of formamide/H₂O/2 M TEAA=3/1/0.1. The resulting solution was stirred at room temperature for 2 h. Upon complete consumption of 6-5', TCEP.HCl (6.80 mg, 23.5 μmol) was added and the reaction mixture was heated to 37° C. After 2 h, LC-MS analysis indicated the complete reduction of disulfide bond and the reaction mixture was diluted to 2.5 mL with MeCN/H₂O=1/1. Purification by C3 reverse phase HPLC (40-90% MeCN in H₂O over 15 min) and lyophilization afforded 10-4 as a white solid, MS: 8189.

In a manner identical to that described above for the preparation of 10-4 was prepared the following compound:

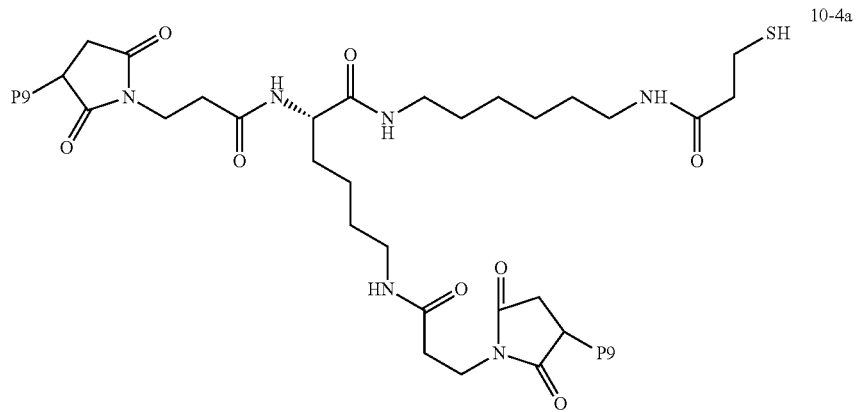

10-4a

Step 3

A solution of 10-3 (6.00 mg, 0.682 μmol) in 400 μL DMSO was treated with a solution of peptide 10-4 (5.67 mg, 0.682 μmol) in 400 μl DMSO. The resulting solution was stirred at room temperature for overnight. The product was purified by size exclusion chromatograph on Superdex™ 75 10/300 column (200 mmol Tris.HCl, 2 M NaCl, pH=8.0). Combined product fractions were diluted with water, and centrifugally dialyzed 5 times against water with MW 10,000 cutoff membrane. The dialyte was lyophilized to provide 10-5 as a white solid, mass-17,200 with polydispersed PEG unit.

Step 4

To a solution of 10-5 (1.90 mg, 0.111 pimp in 400 μL PBS 1× buffer was added a solution of R4g (0.845 mg, 0.122 μmol) in 400 μl PBS 1× buffer. The resulting solution was heated at 90° C. for 1 min and cooled down to room temperature. The annealing reaction mixture was diluted with water, and centrifugally dialyzed four times against water with MW 3000 cutoff membrane. The dialyte was lyophilized to provide 10-6 as a white solid, passenger strand mass~17,200 with polydispersed PEG unit, guide strand=6732.

The following compound was prepared as described above:

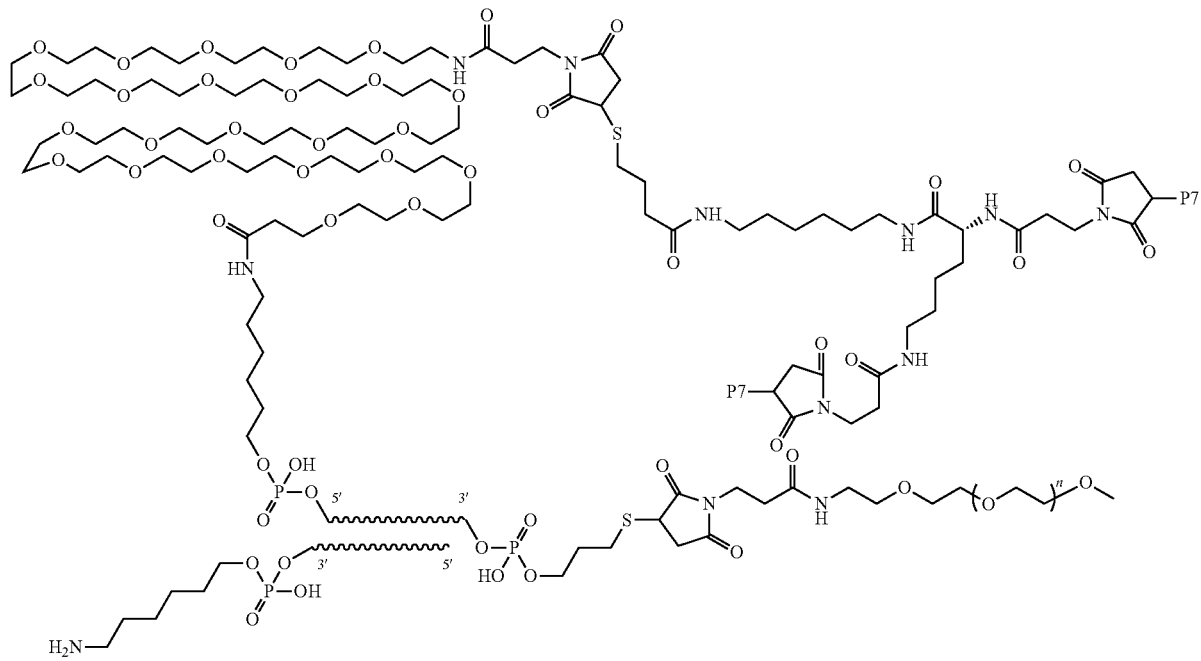

passenger strand mass~17,200 with polydispersed PEG unit, guide strand=6911.

Example 11

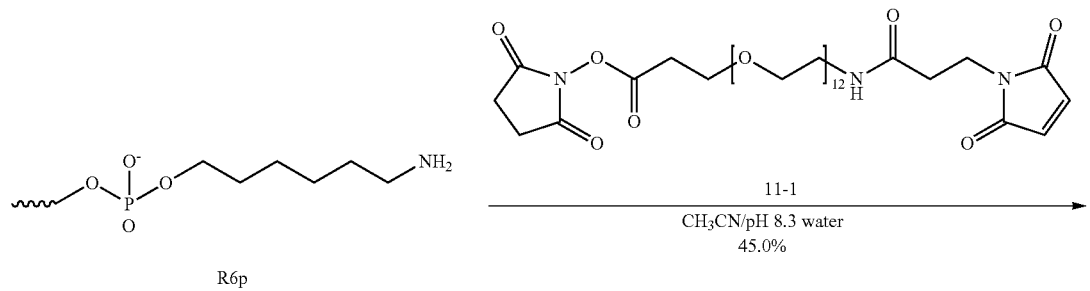

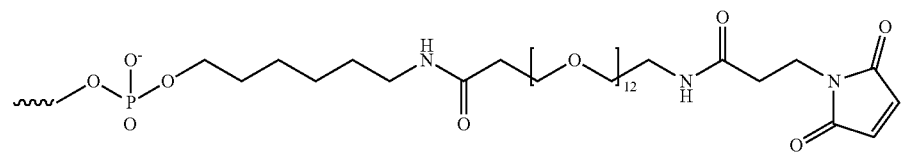

-continued
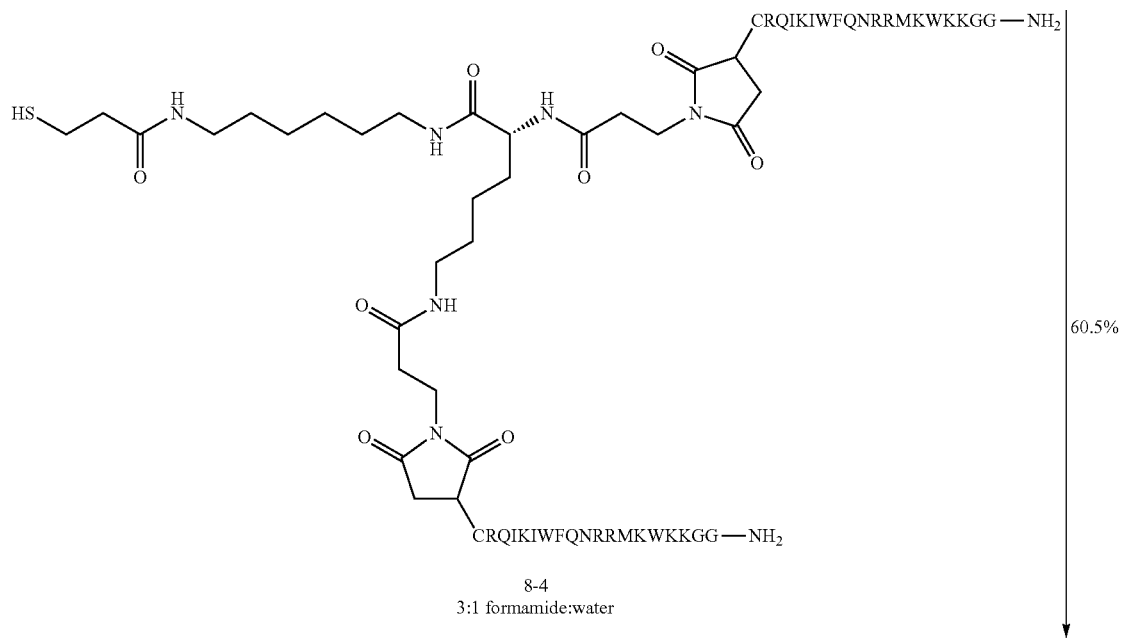
8-4
3:1 formamide:water
60.5%
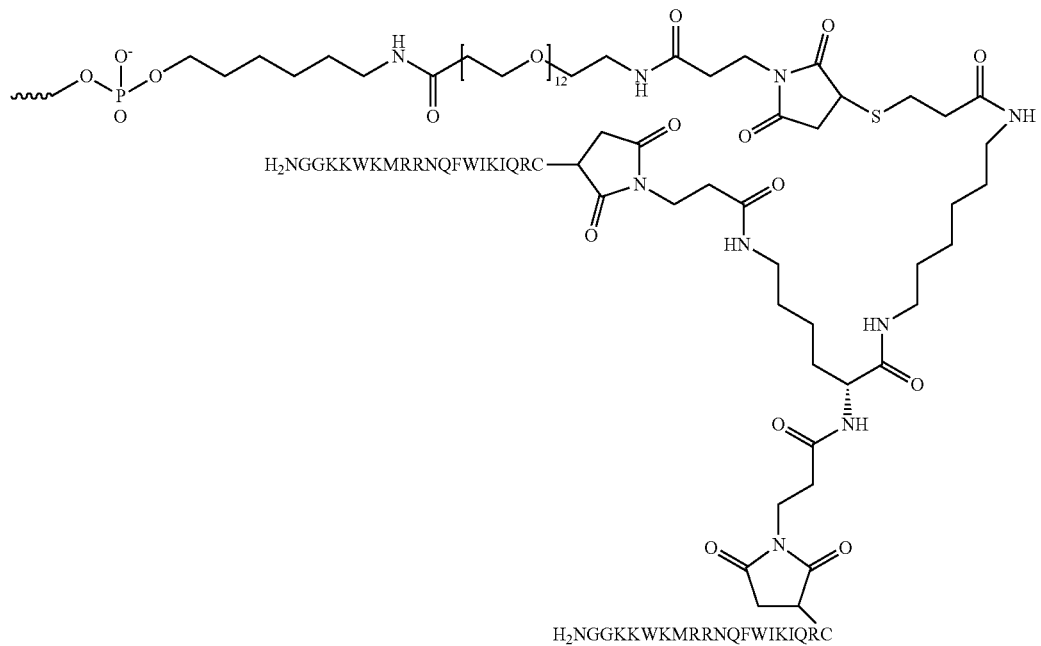
11-3
R4g | PBS pH 7.4
95° C./1 min.
90% recovery

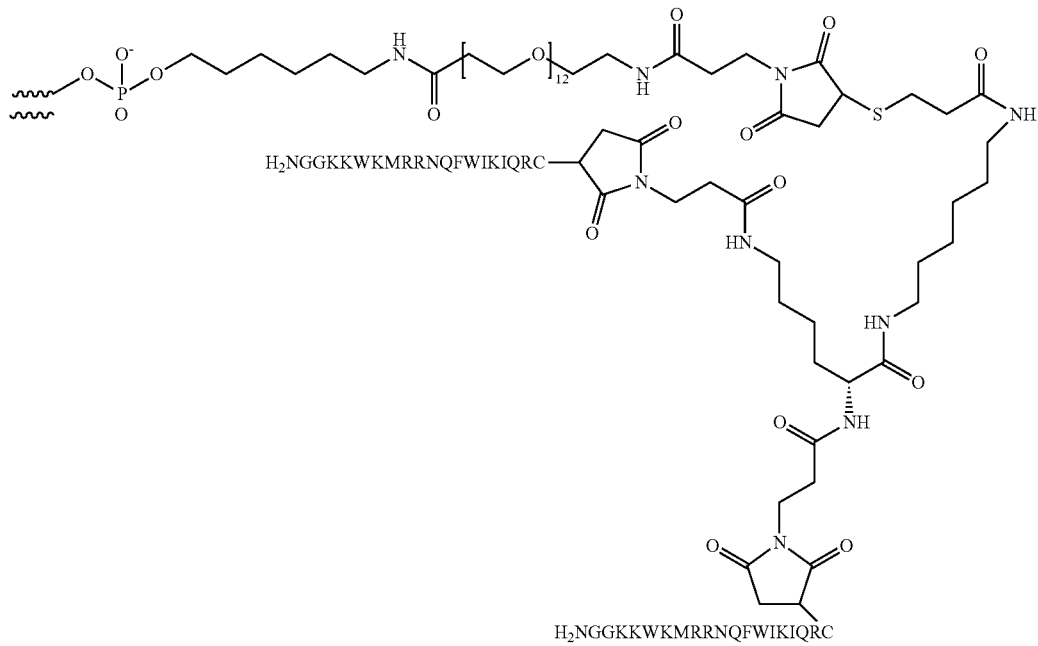

11-4

Step 1

A solution of 25 mg (3.95 μmol) R6p in 2.5 mL pH 8.3 water was treated with a solution of 23.92 mg (0.028 mmol) 11-1 in 500 μL acetonitrile. The resulting solution was stirred for 10 minutes. The crude reaction was purified reverse phase prep LC on a Gilson apparatus using a Waters phenyl Xbridge column (95:5-5:95% A:B linear gradient [A=water with 250 mM TEAA, B=acetonitrile with 250 mM TEAA]). Suspected product peak was diluted with water, and was centrifugally dialyzed four times against water using a MW 3000 dialysis membrane. The dialyte was lyophilized to provide 12.57 mg of the desired conjugate 11-2 as a fluffy white amorphous powder, measured mass=7085.

Step 2

A solution of 5 mg (0.706 μmol) 11-2 in 950 μL 3:1 formamide:water and 150 μL 2M TEAA was treated with a solution of 7.85 mg (1.411 μmol) 8-4 in 1.0 mL 3:1 formamide:water and the resulting solution stirred at RT for 0.5 h. The crude reaction was purified by preparatory anion exchange chromatography on a Gilson apparatus using a 6 mL ResourceQ column and a 100:0-0:100% A:B linear gradient (A=20 mM Tris.HCl, 50% formamide, pH 7.4; B 20 mM Tris.HCl, 400 mM NaClO4, 50% formamide, pH 7.4). Suspected product peak was diluted with water, and was centrifugally dialyzed four times against water using a MW 3000 dialysis membrane. The dialyte was lyophilized to provide 5.4 mg of the desired conjugate 11-3 as an amorphous solid.

Step 3

A slurry of 5.1 mg (0.403 μmol) 11-3 in 500 uL pH 7.4 PBS was treated with a solution of 3.26 mg (0.484 μmol) of R4g added in one portion. The resulting suspension was heated to 95° C. and allowed to cool to room temperature. The resulting solution was cooled and was centrifugally dialyzed three times against water using a MW 3000 dialysis membrane. The dialyte was lyophilized to provide 7.55 mg of the desired duplex product 11-4 as a fluffy white amorphous powder. Duplex was confirmed by MS, measured mass=19378

In a manner similar to that described above for the synthesis of 11-4 was prepared the following compound:

111
112
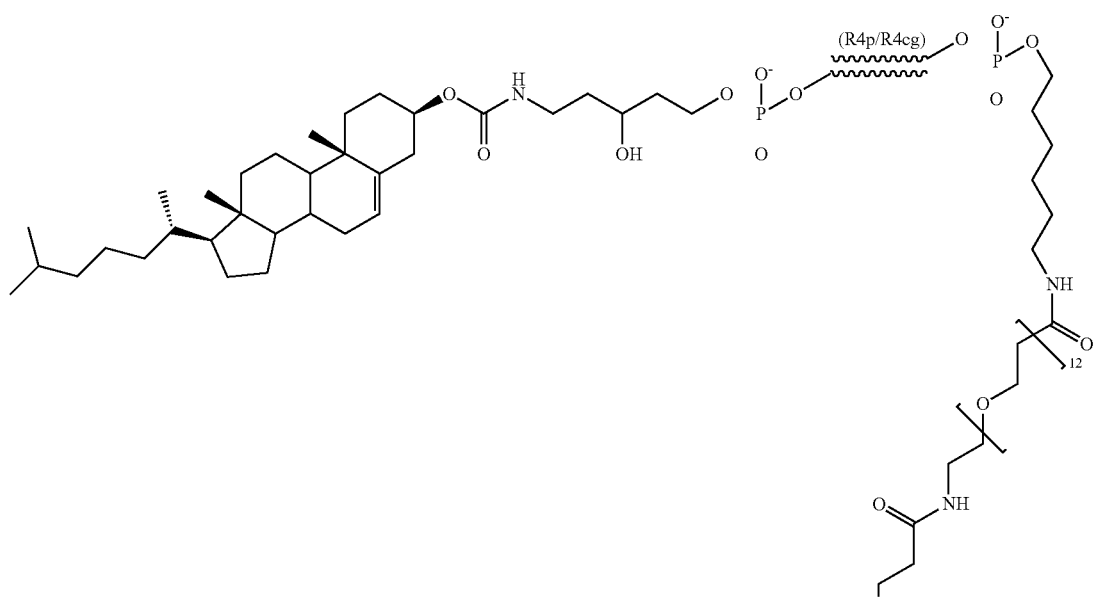
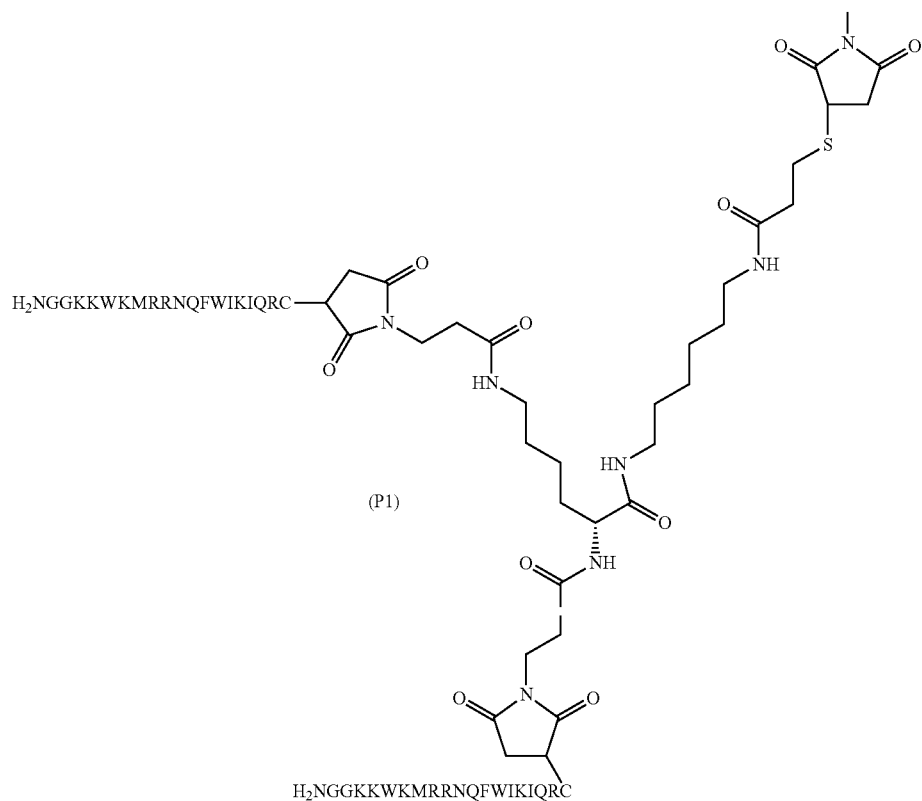
Measured mass = 19979 duplex

Example 12

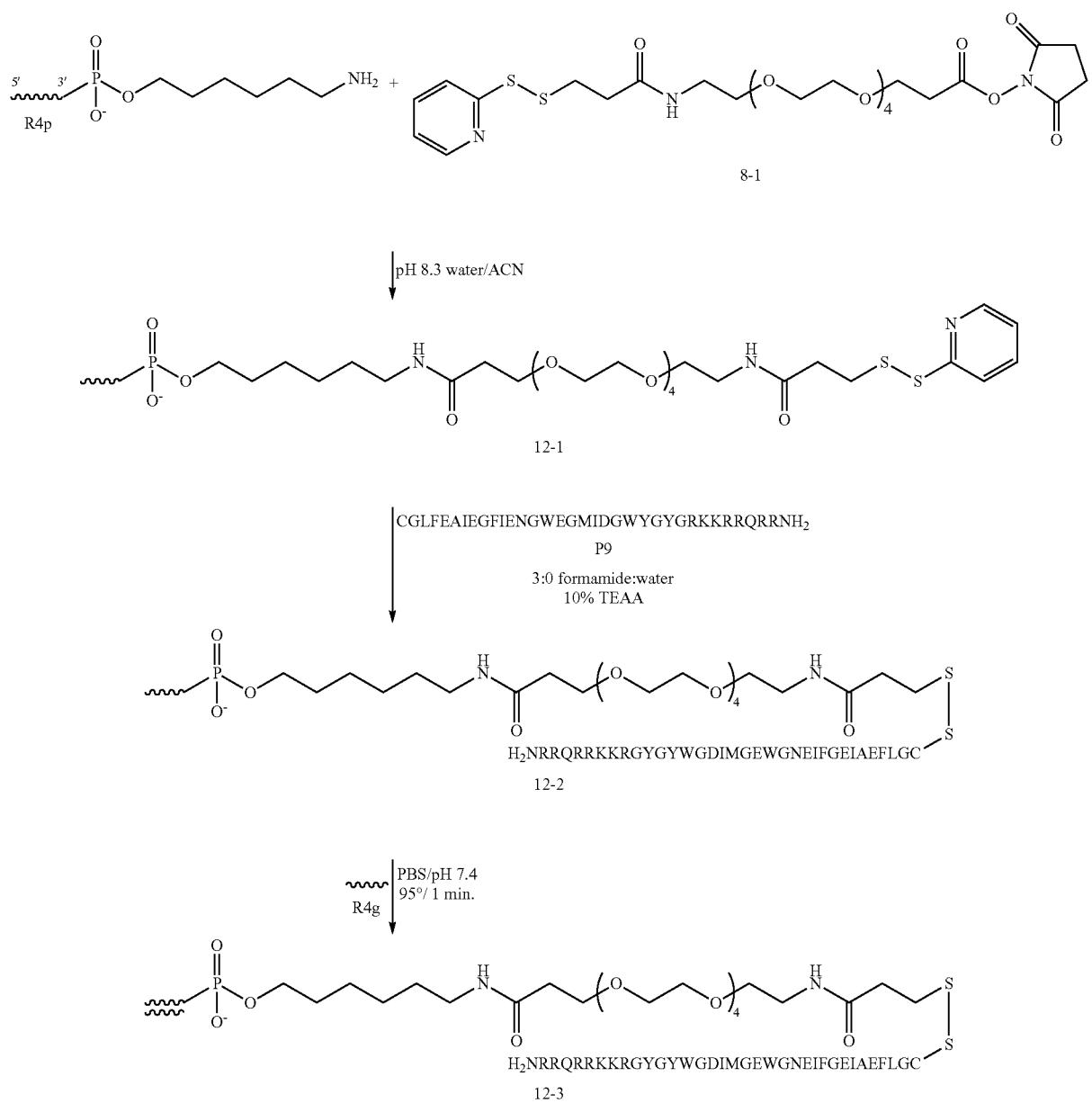

Step 1

A solution of 50.00 mg (7.89 µmol) of R4p in 3600 µl of pH 8.3 water was treated with a solution of 30.90 mg (55.00 µmmol) of 8-1 in 400 µl acetonitrile and the resulting solution was stirred at room temperature for 30 min. The crude reaction was purified by Reverse Phase prep LC (Gilson; 5-95% B gradient; A=200 mM TEAA, B=ACN; 20 min. gradient; Waters Phenyl XBridge column), Suspected product peak was diluted with water, and was centrifugally dialyzed four times against water using a MW 3000 dialysis membrane. The dialyte was frozen and lyophilized overnight to provide 32 mg of the desired product 124 isolated as a fluffy white amorphous powder. 10747

Step 2

A solution of 2.35 mg (0.347 µmol) of 12-1 in 500 µl of 3:1 formamide:water was treated with a solution of 2.83 mg (0.693 mol) of P9 in 450 µl 3:1 formamide:water with 50 µl TEAA added. The reaction was stirred at room temperature for 18 h, and the crude reaction purified by anion exchange prep chromatography (Resource Q column; 10-100% B gradient; A=50% 0.02 mmol Tris/50% formamide; B=50% 0.02 mmol Tris-400 mmol NaOCl4/50% formamide 30-100% A:B gradient over 30 min., 10 ml/min flow). Suspected product peak diluted with water, dialyzed 3× versus water. Aqueous dialyte frozen and lyophilized overnight to give 1.37 mg of desired product 12-2 as a glassy solid. LC/MS measured mass=10747; purity=96%, no residual peptide present.

Step 3

A solution of 1.37 mg (0.131 mol) of 12-2 in 500 µl of pH 7.4 PBS was treated with a solution of 0.792 mg (0.118 µmol)

of R4g in 500 μl of pH 7.4 PBS, and the resulting solution heated at 95 deg. C. for one minute. The resulting solution was cooled to RT, diluted with water, and was dialyzed 3× against water (MW 3000 centrifugal dialysis membrane). The aqueous dialyte was frozen and lyophilized overnight to give 1.45 mg of the desired product 12-3 as a white amorphous powder. LC/MS measured mass passenger=10747, guide=6733, duplex=17481.

Example 13

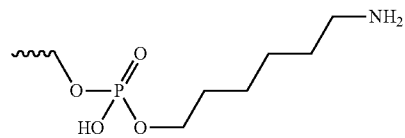

R4p

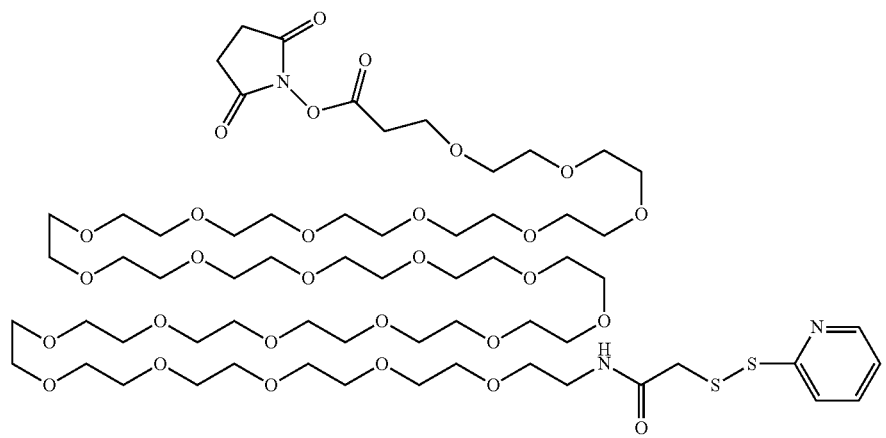

13-1 formamide/pH = 8.0 Tris buffer

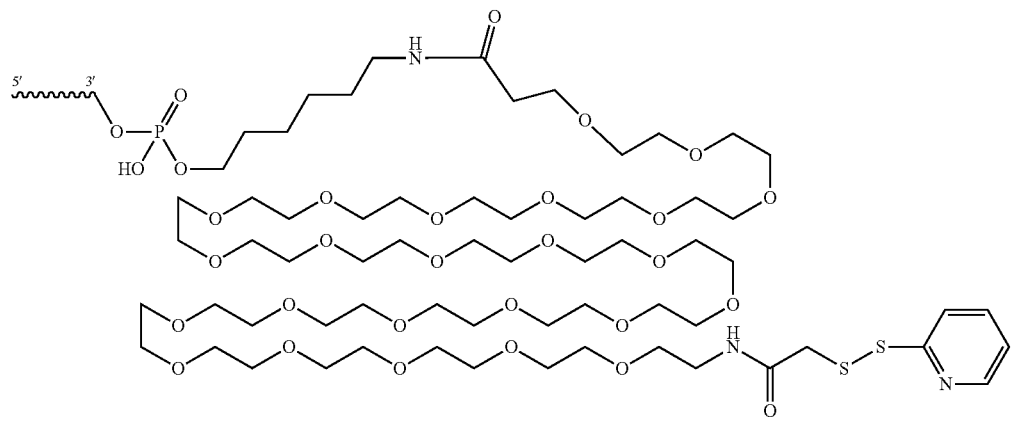

13-2

DMSO, 10-4

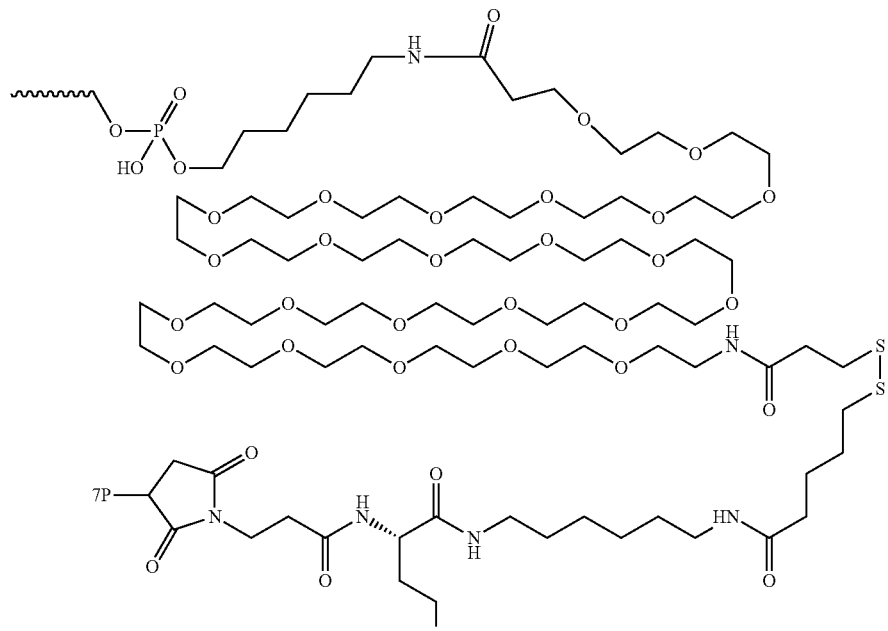
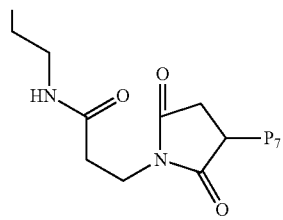
13-3
R4g
PBS 1X Buffer
90° C., 1 min.

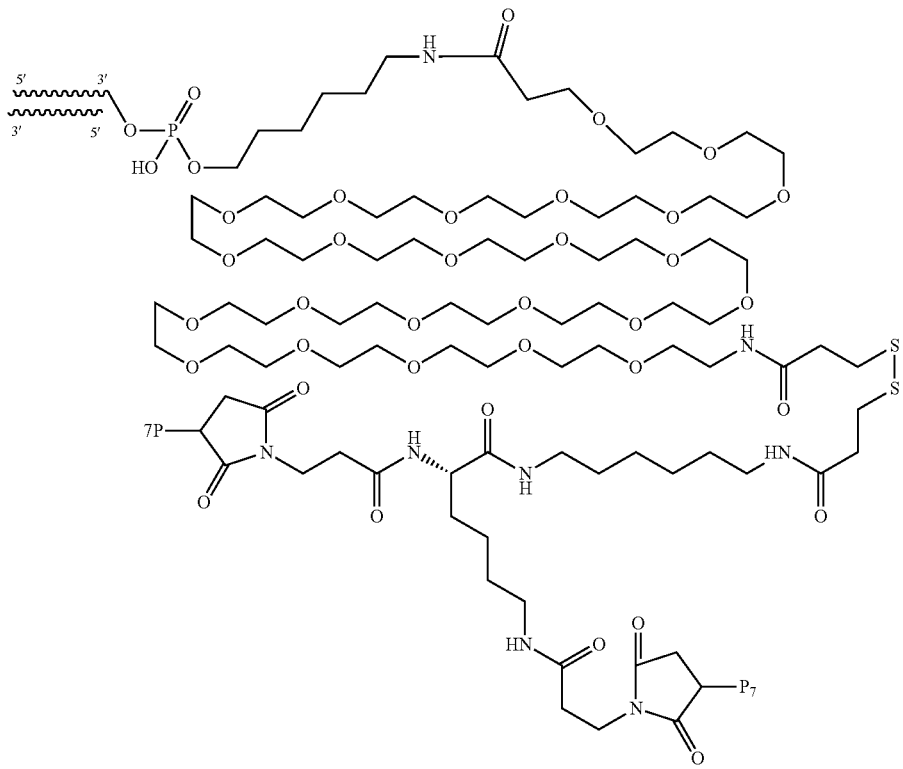

13.4

Step 1

To a solution of R4p (20.0 mg, 3.16 mop in 1.0 mL Tris.HCl buffer (pH=8.0) was added 13-1 (13.65 mg, 9.47 mop in 1.0 mL MeCN at room temperature and the resulting reaction mixture was stirred for 45 min. Upon LC-MS analysis indicated complete consumption of the starting R4p, the reaction mixture was diluted to 2.5 mL with MeCN/H$_2$O=1/1. Purification by X-Bridge™ reverse phase HPLC (10-60% MeCN in H$_2$O over 15 min) and lyophilization afforded 13-2 as a white solid, MS: 7659.

Step 2

A solution of 13-2 (2.00 mg, 0.261 mol) in 400 μL DMSO was treated with a solution of peptide 10-4 (2.57 mg, 0.313 μmol) in 400 μl DMSO. The resulting solution was stirred at room temperature for overnight. The product was purified by anion exchange chromatograph on DNA pack 200 column (50-100% B in A, A: formamide/H$_2$O=1/1, 20 mmol Tris.HCl, pH=7.4, B: formamide/H$_2$O=1/1, 20 mmol Tris.HCl, 400 mmol NaClO$_4$, pH=7.4). Combined product fractions were diluted with water, and centrifugally dialyzed 4 times against water with MW 10,000 cutoff membrane. The dialyte was lyophilized to provide 13-3 as a white solid, mass=15745.

Step 3

To a solution of 13-3 (0.70 mg, 0.044 mmol) in 400 μL PBS 1× buffer was added a solution of R4g (0.33 mg, 0.049 μmol) in 400 μl PBS 1× buffer. The resulting solution was heated at 90° C. for 1 min and cooled down to room temperature. The annealing reaction mixture was diluted with water, and centrifugally dialyzed four times against water with MW 10,000 cutoff membrane. The dialyte was lyophilized to provide 13-4 as a white solid, passenger strand mass=15745, guide strand=6732.

In a manner similar to that described above for the preparation of 13-4 was prepared the following compound:

121 122
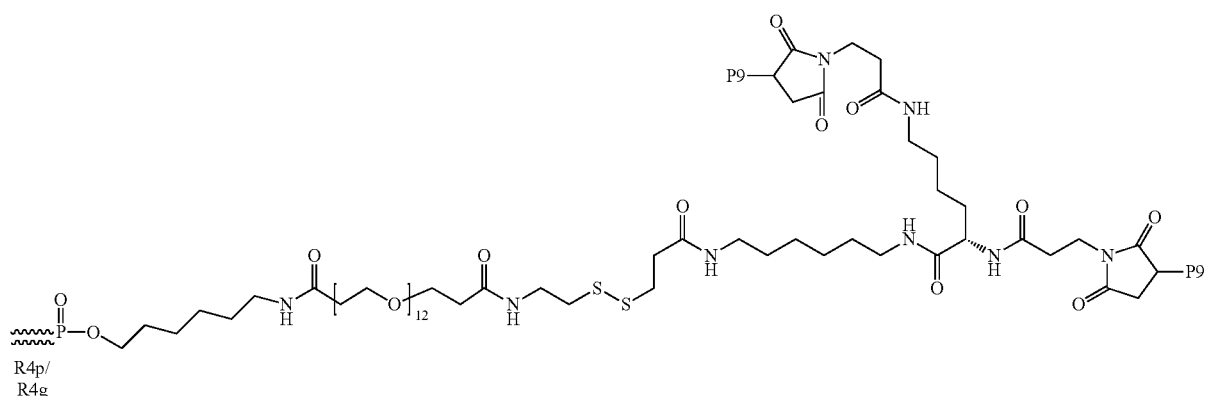
Measured mass = 22548 duplex
Example 14
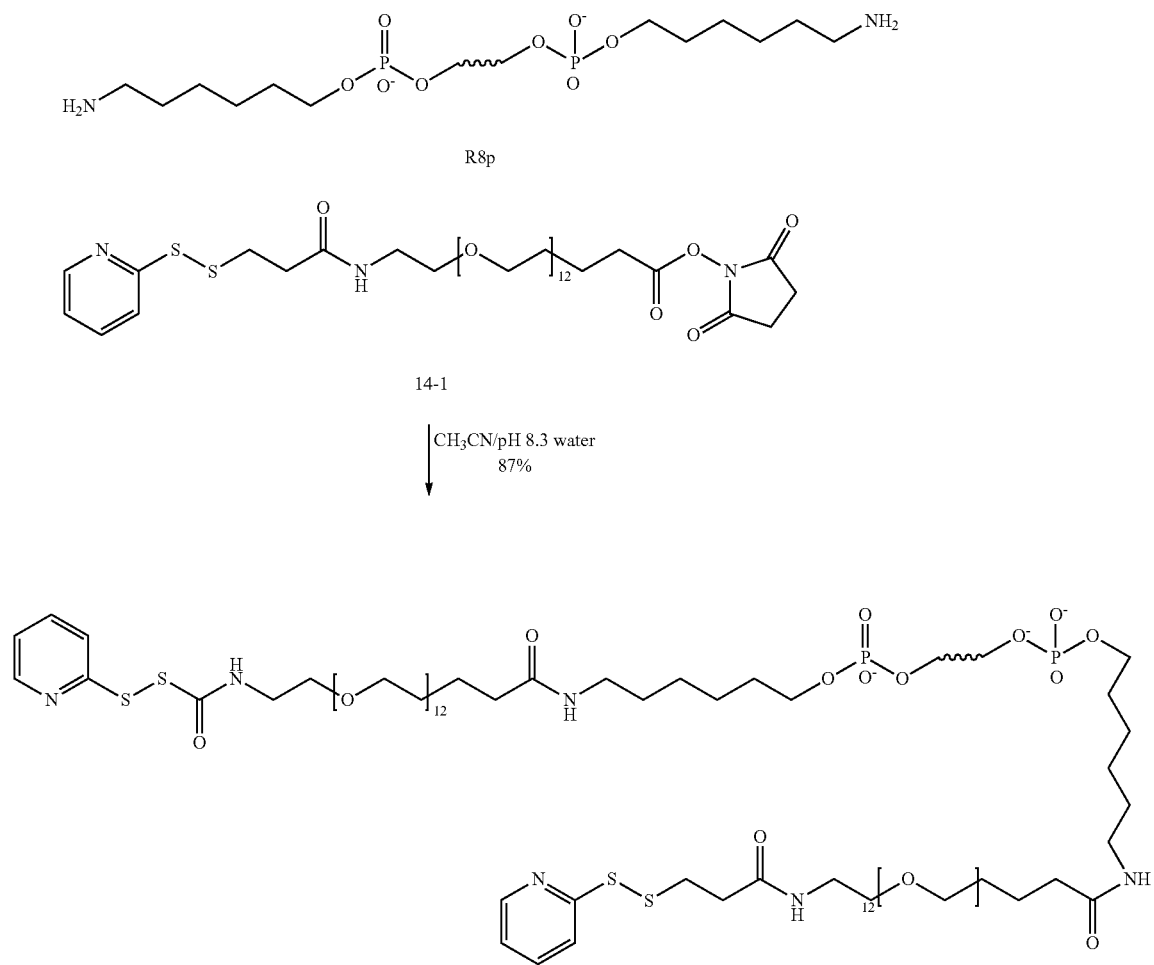

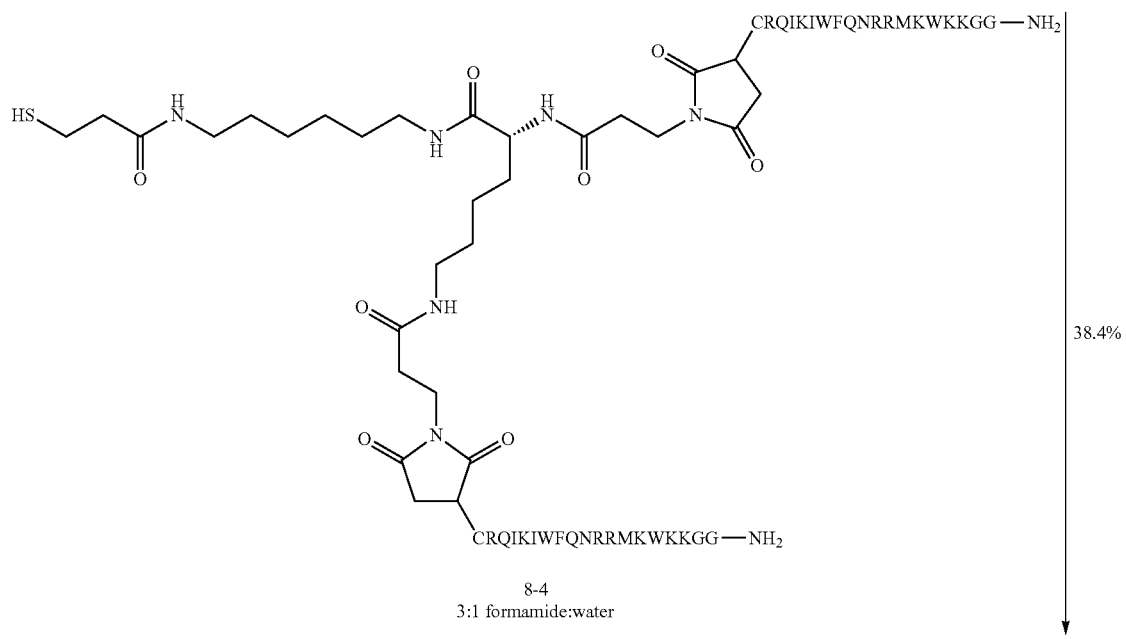
8-4
3:1 formamide:water
38.4%

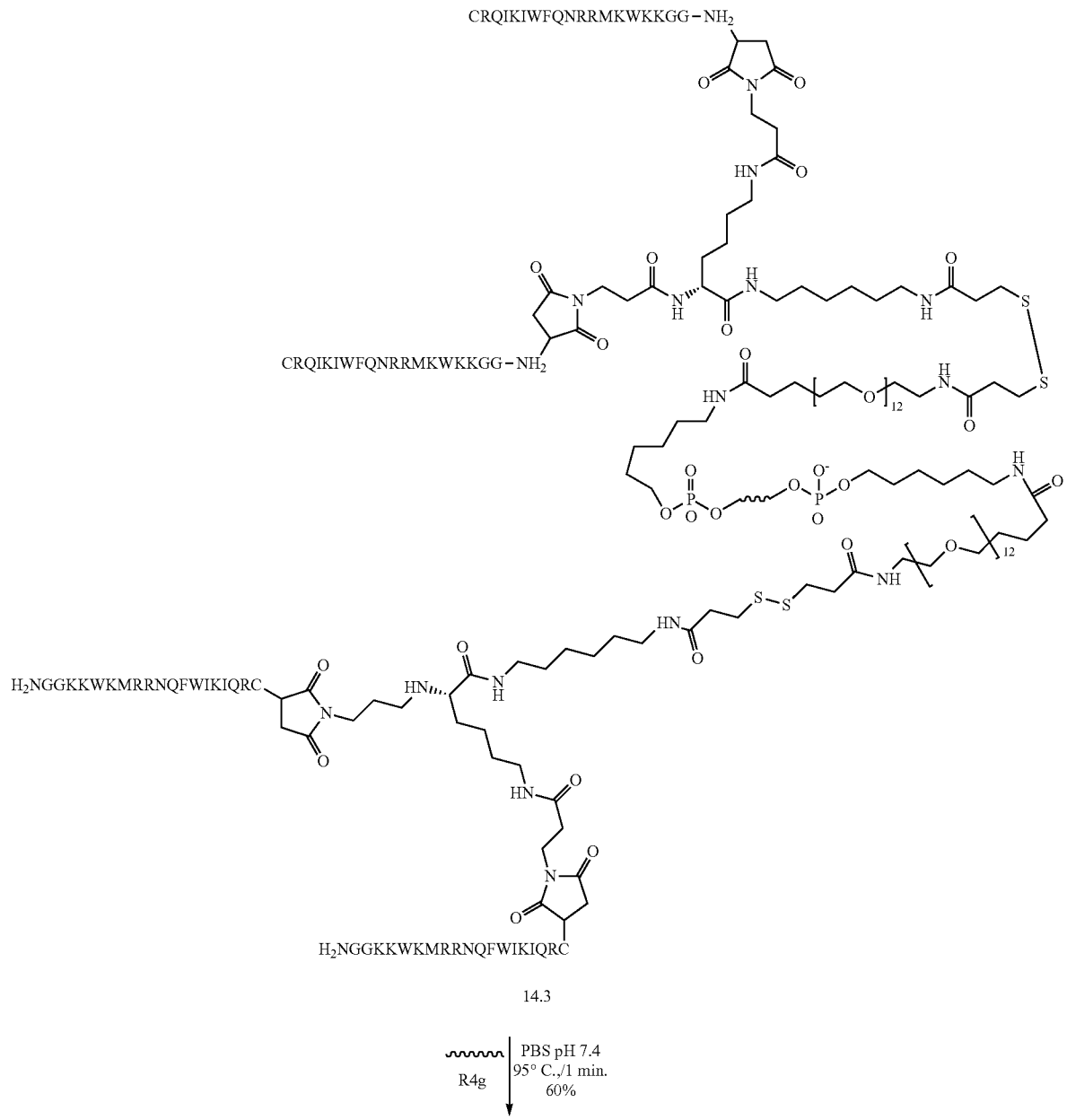

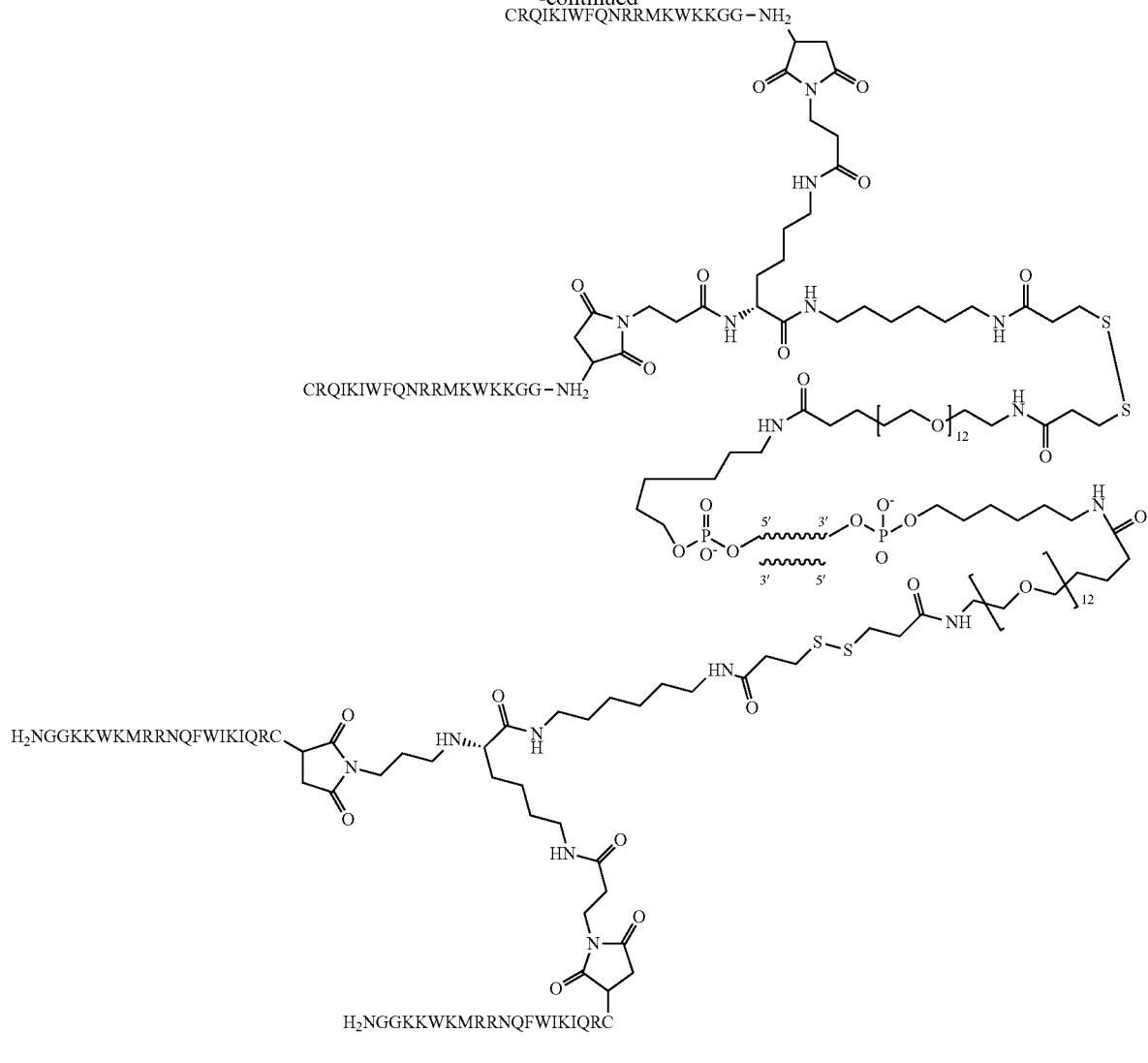

14.4

Step 1

A solution of 20 mg (3.07 μmol) R8p in 1.44 mL pH 8.3 water was treated with a solution of 19.60 mg (0.021 mmol) 14-1 in 160 μL acetonitrile. The resulting solution was stirred for 15 minutes. The crude reaction was purified reverse phase prep LC on a Gilson apparatus using a Waters phenyl Xbridge column (95:5-5:95% A:B linear gradient [A=water with 250 mM TEAA, B=acetonitrile with 250 mM TEAA]). Suspected product peak was diluted with water, and was centrifugally dialyzed four times against water using a MW 3000 dialysis membrane. The dialyte was lyophilized to provide 21.60 mg of the desired conjugate to 14-2 as a fluffy white amorphous powder, measured mass=8106.

Step 2

A solution of 5 mg (0.617 μmol) 14-2 in 950 μL 3:1 formamide:water and 150 μL 2M TEAA was treated with a solution of 13.72 mg (2.467 mmol) 8-3 in 1.0 mL 3:1 formamide:water and the resulting solution stirred at RT for 0.5 h. The crude reaction was purified by preparatory anion exchange chromatography on a Gilson apparatus using a 6 mL ResourceQ column and a 100:0-0:100% A:B linear gradient (A=20 mM Tris.HCl, 50% formamide, pH 7.4; B=20 mM Tris.HCl, 400 mM NaClO4, 50% formamide, pH 7.4). Suspected product peak was diluted with water, and was centrifugally dialyzed four times against water using a MW 3000 dialysis membrane. The dialyte was lyophilized to provide 4.5 mg of the desired conjugate 14-3 as an amorphous solid.

Step 3

A slurry of 1.5 mg (0.079 μmol) 11-3 in 700 μL water was treated with a solution of 0.584 mg (0.087 μmol) of 7-7 added in one portion. The resulting suspension was heated to 95° C. and allowed to cool to room temperature, then decanted into a MW 3000 dialysis membrane. The remaining solid was solubilized using 1:1 formamide:water and combined with the decanted material in the dialysis membrane. The resulting solution was centrifugally dialyzed three times against water using a MW 3000 dialysis membrane. The dialyte was lyophilized to provide 1.26 mg of the desired duplex product 14-4 as a fluffy white amorphous powder. Duplex was confirmed by MS, measured mass=25740.

Example 15

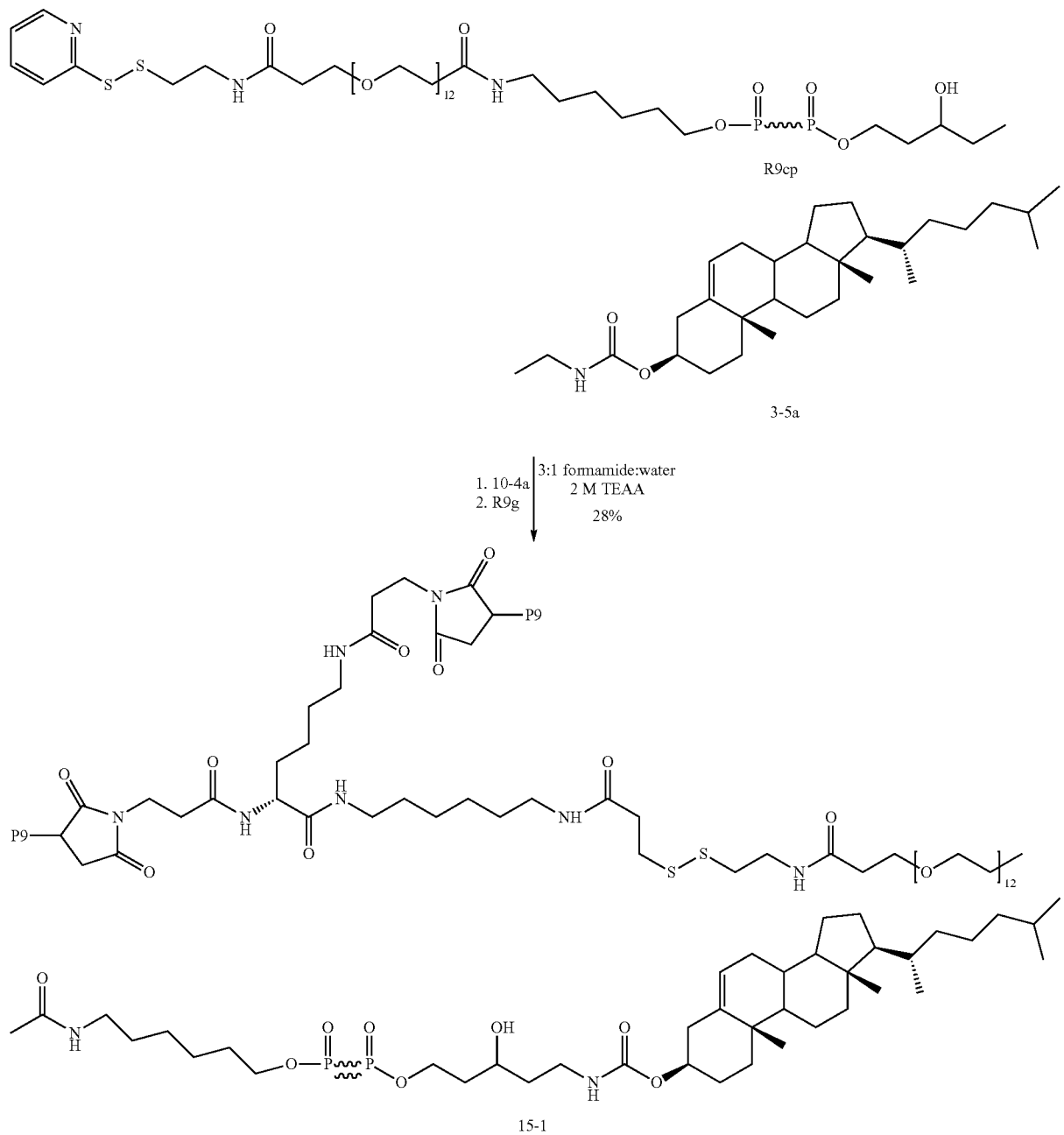

A solution of 5.00 mg (0.573 mmol) of 3-5a in 950 μl of 3:1 formamide:water with 150 μl 2M TEAA was treated with a solution of 10.07 mg (1.145 μmol) of 10-4a in 1 ml of 3:1 formamide:water and the resulting solution stirred at room temperature for 15 min. The crude reaction was treated with 7.77 mg (1.145 μmol) R9g and the duplex purified by preparatory anion exchange chromatography on a Gilson apparatus using 6 mL ResourceQ column and a 95:5-5:95% A:B linear gradient (A=20 mM Tris.HCl, 50% formamide, pH 7.4; B=20 mM Tris.HCl, 400 mM NaClO4, 50% formamide, pH 7.4) Suspected product peak was diluted with water, and was centrifugally dialyzed four times against water using a MW 3000 dialysis membrane. The dialyte was lyophilized to provide 3.93 mg of the desired conjugate 15-1 as a fluffy white amorphous solid, measured mass=24253 (duplex).

Assays

Figure 2:
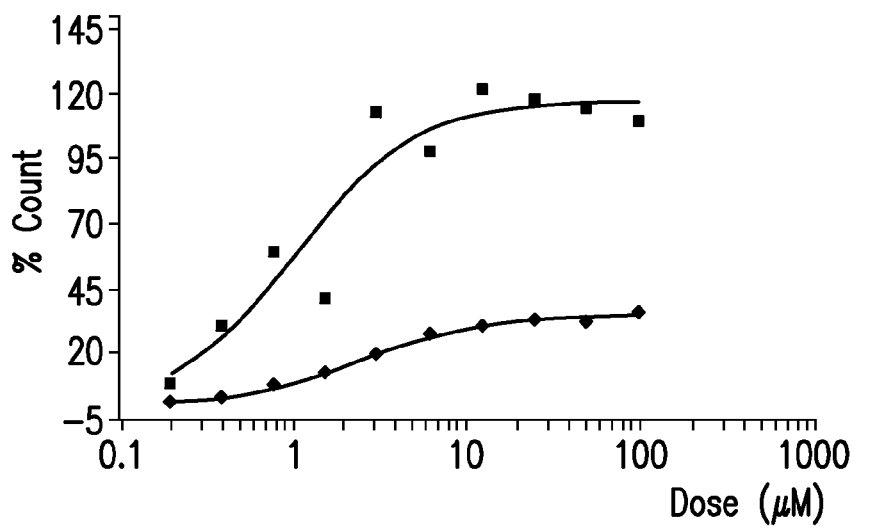
FIG. 2 Percent hemolysis at pH 5.4 and 7.5 for peptide: AcLHLLHHLLHHLHHLLHHLLHLLHHLL-HHLGGGRKKRRQRRRPPQC (SEQ ID NO: 57).
Figure 3:
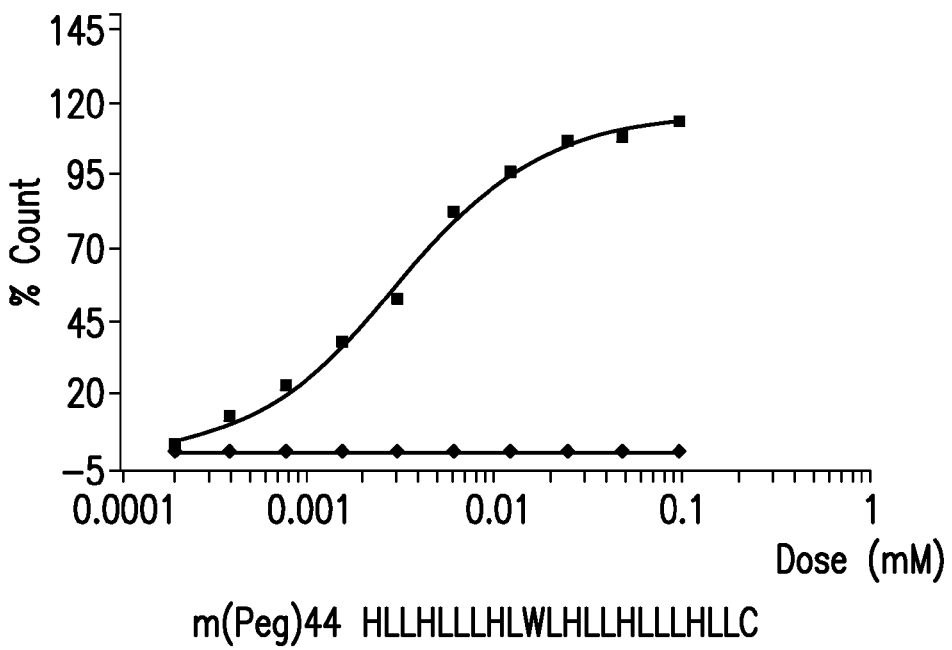
FIG. 3 Percent hemolysis at pH 5.4 and 7.5 for peptide: m(Peg)44HLLHLLLHLWLHLLHLLLHLLC (SEQ ID NO:33).
Figure 4:
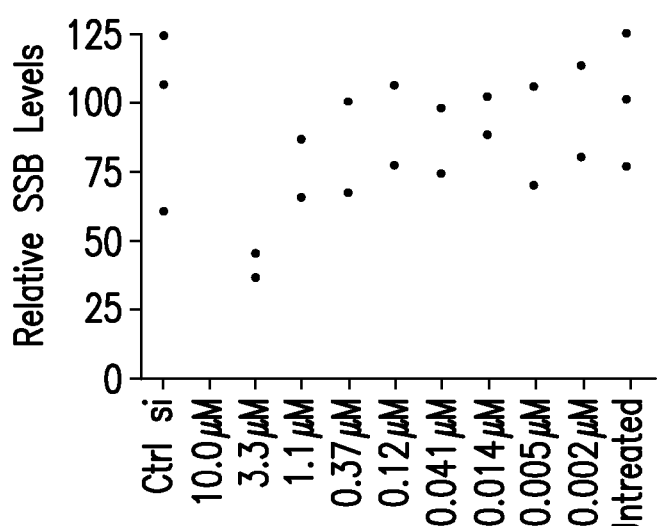
FIG. 4 SSB mRNA levels in HeLa cells treated with compound 3-6 (b-DNA protocol).
Figure 5:
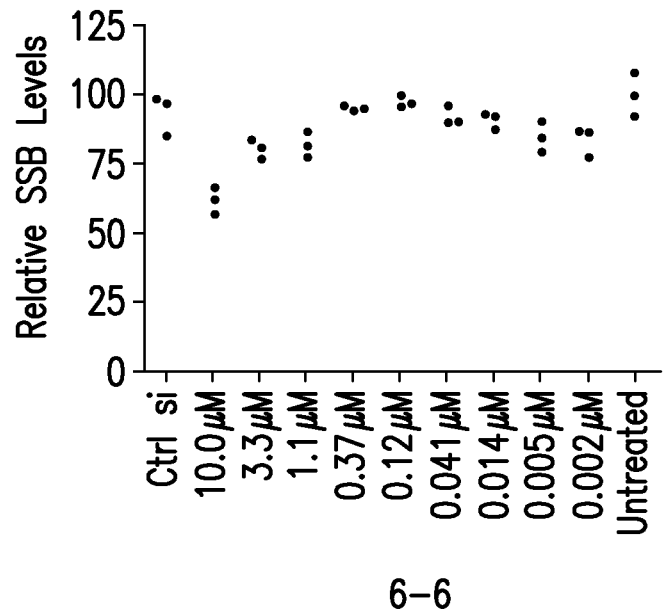
FIG. 5 SSB mRNA levels in HeLa cells treated with compound 6-6 (b-DNA protocol).
Figure 6:
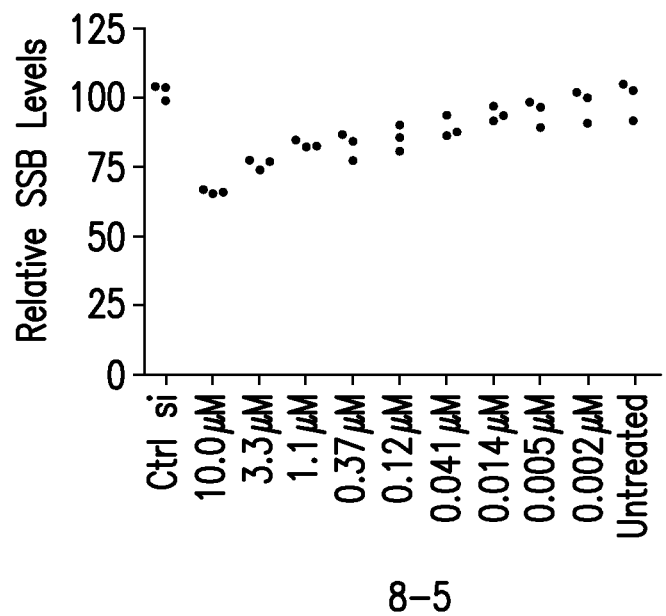
FIG. 6 SSB mRNA levels in HeLa cells treated with compound 8-5 (b-DNA protocol).
Figure 7:
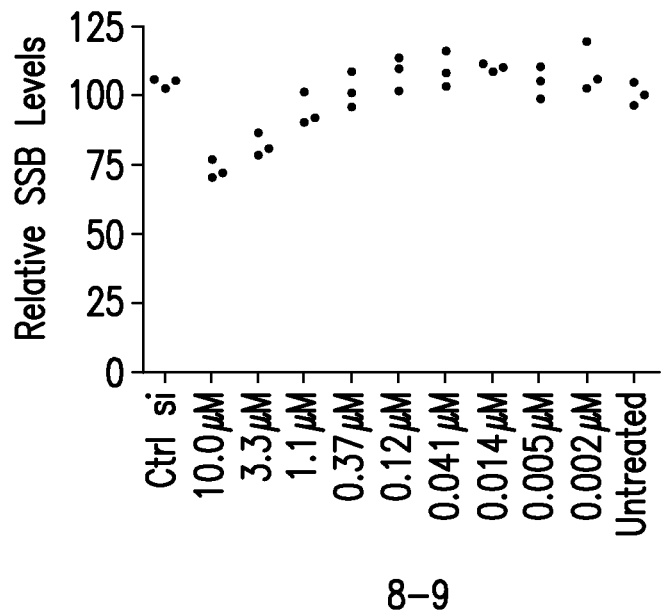
FIG. 7 SSB mRNA levels in HeLa cells treated with compound 8-9 (b-DNA protocol).
Figure 8:
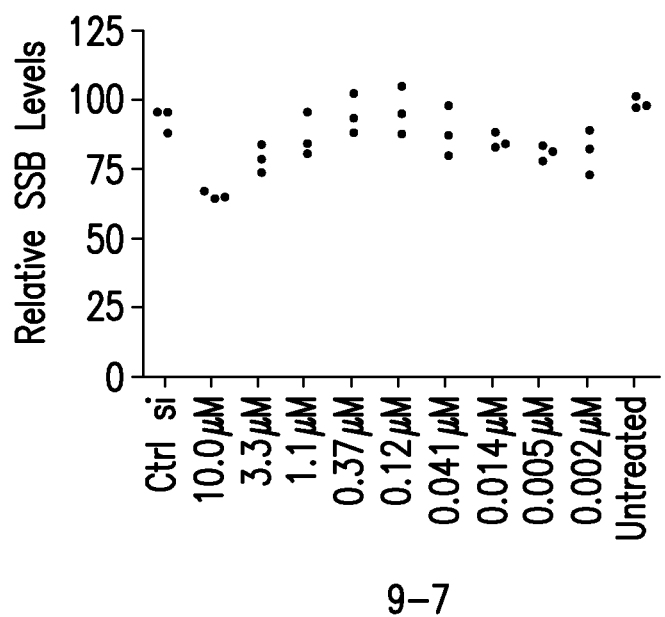
FIG. 8 SSB mRNA levels in HeLa cells treated with compound 9-7 (b-DNA protocol).
Figure 9:
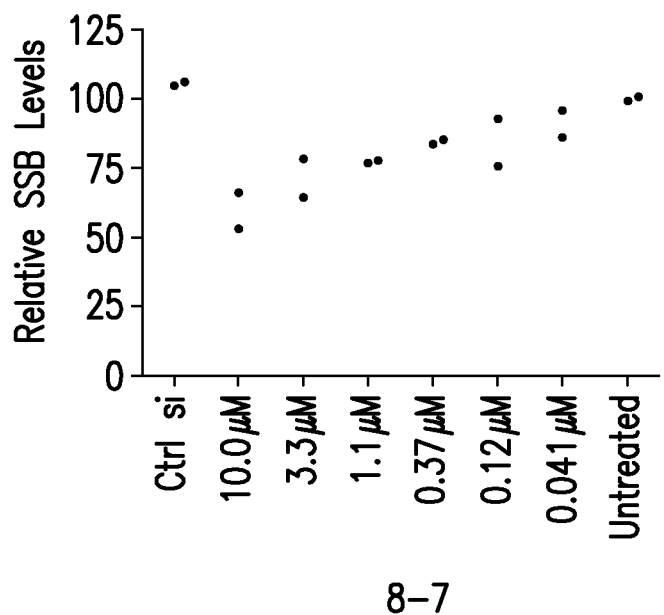
FIG. 9 SSB mRNA levels in HeLa cells treated with compound 8-7 (b-DNA protocol).
Figure 10:
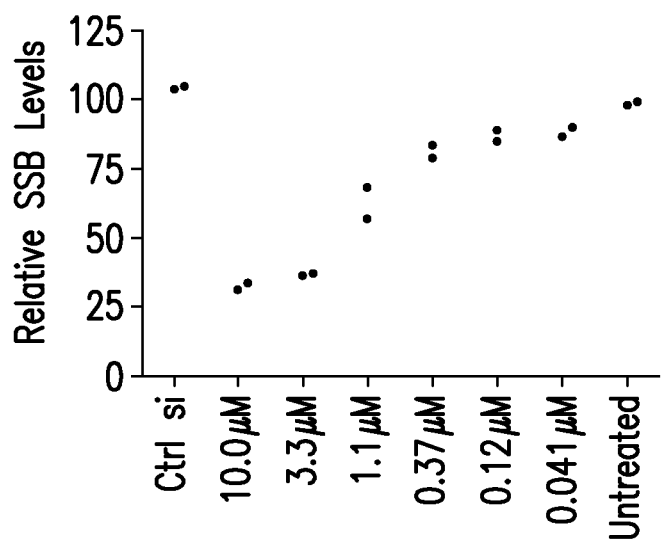
FIG. 10 SSB mRNA levels in HeLa cells treated with compound 13-4 (b-DNA protocol).
Figure 11:
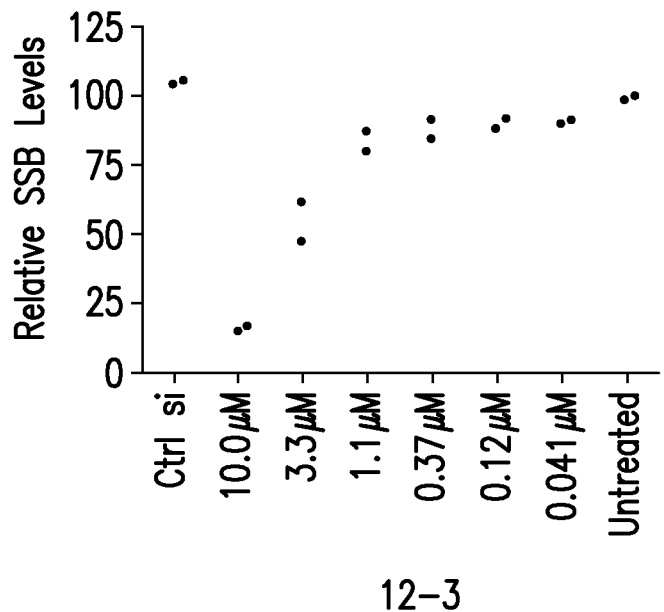
FIG. 11 SSB mRNA levels in HeLa cells treated with compound 12-3 (b-DNA protocol).

RBC Lysis Assay Protocol 2-3 tubes of blood are collected in 10 ml EDTA Vacutainer tubes. The samples are checked for hemolysis by removing a 1-200 μL sample to a microfuge tube and centrifuging in a microfuge at maximum speed for 2 minutes. The supernatants are observed for evidence of hemolysis, with hemolyzed samples discarded. The remaining samples are pooled. 5 ml of pooled blood is removed to a 50 ml centrifuge tube, and is treated with ~35 ml of the appropriate buffer: 100 mM dibasic phosphate at either pH 5.4, or 7.5, For samples that may have solubility problems in phosphate buffers substitute the following: pH 7.5 buffer contains 150 mM NaCl, 20 mM Hepes; pH 5.4 buffer contains 150 mM NaCl, 20 mM MES. The samples are inverted to mix, and are centrifuged at 3000 rpm for 5 minutes. The supernatant is aspirated and the process repeated 2×. The RBC are resuspended to a total volume of 50 ml of the desired pH buffer and are stored on ice. Serial dilutions of compounds to be tested are prepared in a V-bottom or Easy-Wash 96 well plate, either in buffer or water as appropriate. The standard assay uses a 10 point 2-fold dilution series. Compound dilutions typically are prepared at a 10× concentration in 25 μL final volume. The highest concentration tested depends on the material and its respective solubility. A typical concentration is 100 μM. Buffer alone and 1% Triton X-100 in PBS are included as negative and positive controls respectively. Dilutions can be prepared as either duplicates or single wells depending on the number of samples to be tested and the amount of material available for testing. 175 μL of the appropriate pH buffer is added to each well. 50 μL of the washed RBC suspension is added manually using wide bore pipette tips. The samples are triturated approximately 6-8× to mix and are incubated in a 37° C. warm room or incubator for 30 minutes. The plate is covered with a low evaporation lid during this process. The plate is removed from the warm room or incubator and is centrifuged at ~3000 rpm for 5 minutes. 150 μL of the supernatant is transferred to a clear bottom 96 well white plate and the absorbance is read at 541 nM. For calculations, the background absorbance is subtracted from all samples, with each pH grouping treated separately. The % hemolysis is calculated for each sample as a % of the Triton X-100 sample (100% hemolysis). The data is plotted and sample curves are shown below in FIGS. 1-3. The square graph line represents % hemolysis at pH 5.4, and the diamond graph line represents % hemolysis at pH 7.5.

siRNA bDNA Assay General Protocol

The siRNAs described herein were designed to target ubiquitously expressesd gene SSB (Sjogren syndrome antigen B; NM_009278.4). The sequence of the siRNA used is homologus in human, mouse and rat transcripts. To test the silencing activity of siRNA conjugates, HeLa (Human cervical cancer cell line) cells were plated in media (DMEM) supplemented with 10% fetal calf serum (FCS) and allowed to culture overnight (37° C., 5% $CO_2$). On next day, the media was replaced with serum free media containing the siRNA conjugates at concentrations ranging from 10-0.0015 μM and left on cells for total of 72 hrs (37° C., 5% $CO_2$). The SSB mRNA levels were analyzed using branched-DNA assay as per instructions by supplier (Panomics Quantigene 1.0 bDNA Kit #QG0002). The cell viability was assessed using MTS assay (Promega cat#TB245) and all the data was normalized to levels from untreated cells.

As shown in FIGS. 4-11, the HeLa cells were treated with compounds indicated for 72 hrs in dose-dependent manner and the levels of SSB mRNA were analyzed by b-DNA assay.

siRNA Dual Luciferase Assay General Protocol

To test the silencing activity of siRNA conjugates, HEK293T cells stably transfected with luciferase vector were plated in media (DMEM) supplemented with 10% fetal calf serum (FCS) and allowed to culture overnight (37° C., 5% $CO_2$). This reporter cell system contains a Renilla-Firefly Dual-luciferase construct and has the SSB target sites incorporated in the 3' UTR of Renilla luciferase. Next day, the media was replaced with serum free media containing the siRNA conjugates at concentrations ranging from 10-0.01 μM and left on cells for total of 24 hr (37° C., 5% $CO_2$). The Firefly and Renilla protein levels were analyzed using the Dual-Glo assay from Promega as per instructions by supplier (Promega Cat#E2920). The Firefly signal was used as a control for cell viability & Renilla/Firefly luciferase activity was used for specific mRNA knockdown. All data was normalized to levels from untreated cells.

Figure 12:
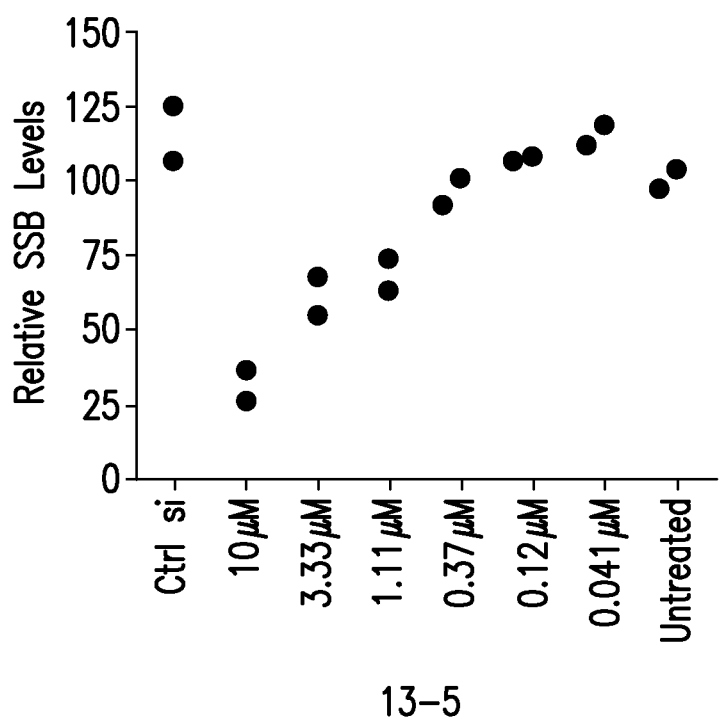
FIG. 12 SSB mRNA levels in HeLa cells treated with compound 13-5 (b-DNA protocol).
Figure 13:
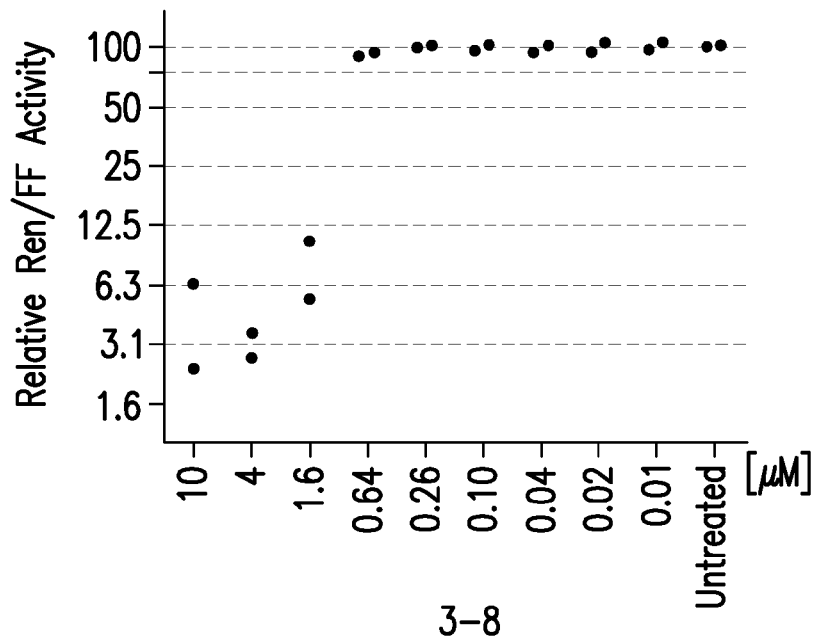
FIG. 13 SSB mRNA levels in HEK293T cells treated with compound 3-8 (Dual Luciferase protocol).
Figure 14:
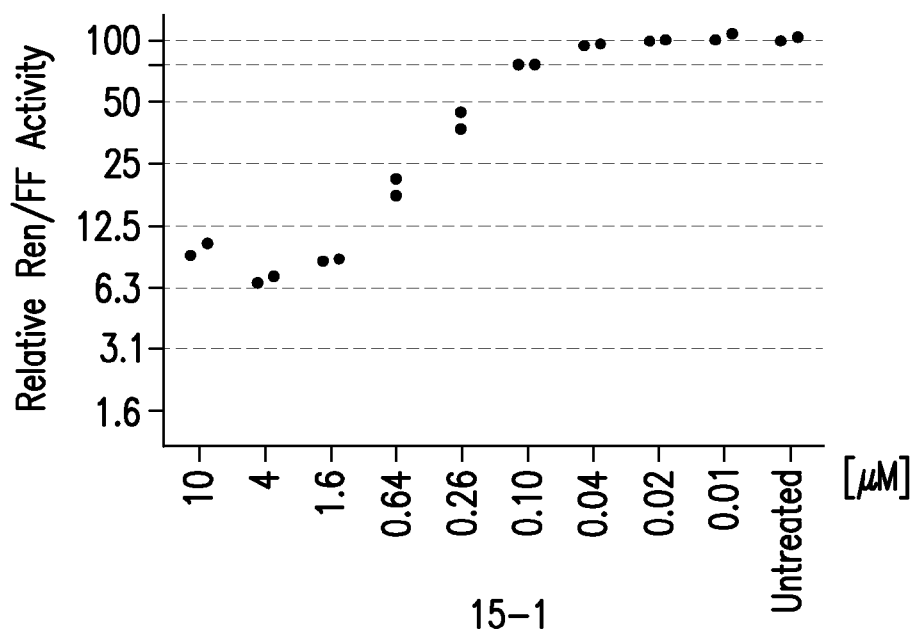
FIG. 14 SSB mRNA levels in HEK293T cells treated with compound 15-1 (Dual Luciferase protocol).

As shown in FIGS. 12-14, the HEK293T cells were treated with compounds indicated for 24 hrs in dose-dependent manner and the levels of SSB mRNA were analyzed by b-DNA assay.

Ocular Screening Protocol

Figure 15:
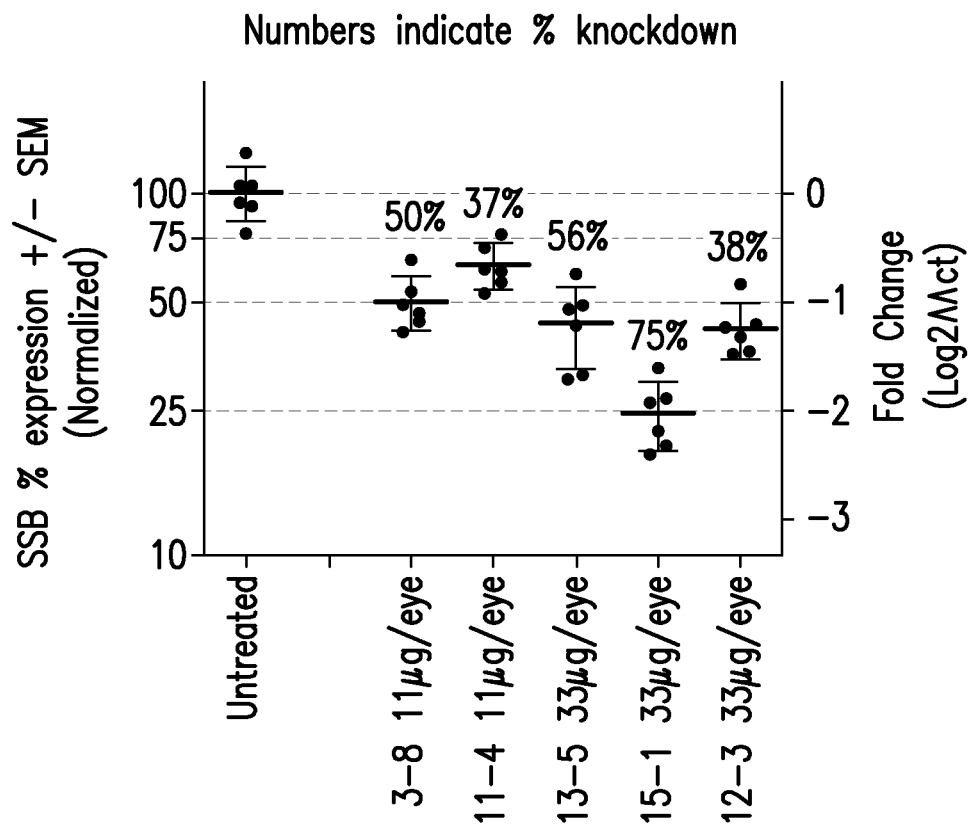
FIG. 15 Relative levels of SSB mRNA in rat retina tissue 3 days after single intravitreal dose of indicated compounds.

All procedures involving animals were performed in accordance with the ARVO Statement for the Use of Animals in Ophthalmic and Vision Research and were approved by the Institutional Animal Care and Use Committee (IACUC) of Merck Research Laboratories, West Point, Pa. Male Brown Norway rats (6-8 weeks) were purchased from Charles River Laboratories. siRNAs were prepared aseptically to minimize the risk of infection. For intravitreal dosing, rats were anesthetized with ketamine/xylazine (40-90/5-10 mg/kg, IM), and 1% proparacaine hydrochloride (1-2 drops) was applied to the eye as topical anesthetic. For intravitreal injection, a pair of clean forceps was used to gently proctose and hold in place the eye, and a 30G sharp-needled syringe was used to inject 5 ul of test siRNA or control vehicle into the vitreous just posterior to the limbus. On the day of sacrifice, rats were euthanized with sodium pentobarbital (150-200 mg/kg, IP). Following enucleation, vitreous, retina, and is RPE/choroid were dissected and frozen. The retinal tissue was homogenized in RLT lysis buffer (Quaigen catalog #79216) and total RNA was purified using the Qiagen Rneasy 96 kit (catalog #74181). The total RNA was then analyzed by quantitative PCR to determine relative mRNA levels of target gene SSB with housekeeping genes like GAPDH and PPIB. FIG. 15 details the relative levels of SSB mRNA in rat retina tissue 3 days after single intravitreal dose the indicated compounds.

SEQUENCE LISTING

<160> NUMBER OF SEQ ID NOS: 59

<210> SEQ ID NO 1
<211> LENGTH: 20
<212> TYPE: PRT
<213> ORGANISM: Artificial Sequence
<220> FEATURE:
<223> OTHER INFORMATION: Completely Synthetic Amino Acid Sequence

<400> SEQUENCE: 1

His Phe His His Phe Phe His His Phe Phe His Phe Phe His His Phe
 1               5                   10                  15

Phe His His Phe
            20

```
<210> SEQ ID NO 2
<211> LENGTH: 15
<212> TYPE: PRT
<213> ORGANISM: Artificial Sequence
<220> FEATURE:
<223> OTHER INFORMATION: Completely Synthetic Amino Acid Sequence

<400> SEQUENCE: 2

Trp His His Trp Trp His Trp Trp His His Trp Trp His His Trp
 1               5                  10                  15

<210> SEQ ID NO 3
<211> LENGTH: 20
<212> TYPE: PRT
<213> ORGANISM: Artificial Sequence
<220> FEATURE:
<223> OTHER INFORMATION: Completely Synthetic Amino Acid Sequence

<400> SEQUENCE: 3

His Trp His His Leu Leu His His Leu Leu His Leu Leu His His Leu
 1               5                  10                  15

Leu His His Leu
            20

<210> SEQ ID NO 4
<211> LENGTH: 20
<212> TYPE: PRT
<213> ORGANISM: Artificial Sequence
<220> FEATURE:
<223> OTHER INFORMATION: Completely Synthetic Amino Acid Sequence

<400> SEQUENCE: 4

His Leu His His Trp Leu His His Leu Leu His Leu Leu His His Leu
 1               5                  10                  15

Leu His His Leu
            20

<210> SEQ ID NO 5
<211> LENGTH: 20
<212> TYPE: PRT
<213> ORGANISM: Artificial Sequence
<220> FEATURE:
<223> OTHER INFORMATION: Completely Synthetic Amino Acid Sequence

<400> SEQUENCE: 5

His Leu His His Leu Trp His His Leu Leu His Leu Leu His His Leu
 1               5                  10                  15

Leu His His Leu
            20

<210> SEQ ID NO 6
<211> LENGTH: 20
<212> TYPE: PRT
<213> ORGANISM: Artificial Sequence
<220> FEATURE:
<223> OTHER INFORMATION: Completely Synthetic Amino Acid Sequence

<400> SEQUENCE: 6

His Leu His His Leu Leu His His Leu Trp His Leu Leu His His Leu
 1               5                  10                  15

Leu His His Leu
            20

<210> SEQ ID NO 7
<211> LENGTH: 20
<212> TYPE: PRT
```

```
<213> ORGANISM: Artificial Sequence
<220> FEATURE:
<223> OTHER INFORMATION: Completely Synthetic Amino Acid Sequence

<400> SEQUENCE: 7

His Leu His His Leu Leu His His Leu Leu His Trp Leu His His Leu
 1               5                   10                  15

Leu His His Leu
            20

<210> SEQ ID NO 8
<211> LENGTH: 20
<212> TYPE: PRT
<213> ORGANISM: Artificial Sequence
<220> FEATURE:
<223> OTHER INFORMATION: Completely Synthetic Amino Acid Sequence

<400> SEQUENCE: 8

His Leu His His Leu Leu His His Leu Leu His Leu Leu His His Trp
 1               5                   10                  15

Leu His His Leu
            20

<210> SEQ ID NO 9
<211> LENGTH: 20
<212> TYPE: PRT
<213> ORGANISM: Artificial Sequence
<220> FEATURE:
<223> OTHER INFORMATION: Completely Synthetic Amino Acid Sequence

<400> SEQUENCE: 9

His Leu His His Leu Leu His His Leu Leu His Leu Leu His His Leu
 1               5                   10                  15

Trp His His Leu
            20

<210> SEQ ID NO 10
<211> LENGTH: 20
<212> TYPE: PRT
<213> ORGANISM: Artificial Sequence
<220> FEATURE:
<223> OTHER INFORMATION: Completely Synthetic Amino Acid Sequence

<400> SEQUENCE: 10

His Pro His His Leu Leu His His Leu Leu His Leu Leu His His Leu
 1               5                   10                  15

Leu His His Leu
            20

<210> SEQ ID NO 11
<211> LENGTH: 20
<212> TYPE: PRT
<213> ORGANISM: Artificial Sequence
<220> FEATURE:
<223> OTHER INFORMATION: Completely Synthetic Amino Acid Sequence

<400> SEQUENCE: 11

His Leu His His Pro Leu His His Leu Leu His Leu Leu His His Leu
 1               5                   10                  15

Leu His His Leu
            20

<210> SEQ ID NO 12
<211> LENGTH: 20
<212> TYPE: PRT
```

```
<213> ORGANISM: Artificial Sequence
<220> FEATURE:
<223> OTHER INFORMATION: Completely Synthetic Amino Acid Sequence

<400> SEQUENCE: 12

His Leu His His Leu Pro His His Leu Leu His Leu Leu His His Leu
1               5                   10                  15

Leu His His Leu
            20

<210> SEQ ID NO 13
<211> LENGTH: 20
<212> TYPE: PRT
<213> ORGANISM: Artificial Sequence
<220> FEATURE:
<223> OTHER INFORMATION: Completely Synthetic Amino Acid Sequence

<400> SEQUENCE: 13

His Leu His His Leu Leu His His Leu Pro His Leu Leu His His Leu
1               5                   10                  15

Leu His His Leu
            20

<210> SEQ ID NO 14
<211> LENGTH: 20
<212> TYPE: PRT
<213> ORGANISM: Artificial Sequence
<220> FEATURE:
<223> OTHER INFORMATION: Completely Synthetic Amino Acid Sequence

<400> SEQUENCE: 14

His Leu His His Leu Leu His His Leu Leu His Leu Leu His His Leu
1               5                   10                  15

Pro His His Leu
            20

<210> SEQ ID NO 15
<211> LENGTH: 20
<212> TYPE: PRT
<213> ORGANISM: Artificial Sequence
<220> FEATURE:
<223> OTHER INFORMATION: Completely Synthetic Amino Acid Sequence

<400> SEQUENCE: 15

His Leu His His Leu Leu His His Leu Leu His Leu Leu His His Leu
1               5                   10                  15

Leu His His Pro
            20

<210> SEQ ID NO 16
<211> LENGTH: 20
<212> TYPE: PRT
<213> ORGANISM: Artificial Sequence
<220> FEATURE:
<223> OTHER INFORMATION: Completely Synthetic Amino Acid Sequence

<400> SEQUENCE: 16

Glu Leu Glu Glu Leu Leu Glu Glu Leu Leu His Leu Leu His His Leu
1               5                   10                  15

Leu His His Leu
            20

<210> SEQ ID NO 17
<211> LENGTH: 20
<212> TYPE: PRT
```

```
<213> ORGANISM: Artificial Sequence
<220> FEATURE:
<223> OTHER INFORMATION: Completely Synthetic Amino Acid Sequence

<400> SEQUENCE: 17

Glu Leu His His Leu Leu His Glu Leu Leu His Leu Leu His Glu Leu
1               5                   10                  15

Leu His His Leu
            20

<210> SEQ ID NO 18
<211> LENGTH: 21
<212> TYPE: PRT
<213> ORGANISM: Artificial Sequence
<220> FEATURE:
<223> OTHER INFORMATION: Completely Synthetic Amino Acid Sequence

<400> SEQUENCE: 18

Gly Leu Trp Arg Ala Leu Trp Arg Leu Leu Arg Ser Leu Trp Arg Leu
1               5                   10                  15

Leu Trp Arg Ala Cys
            20

<210> SEQ ID NO 19
<211> LENGTH: 33
<212> TYPE: PRT
<213> ORGANISM: Artificial Sequence
<220> FEATURE:
<223> OTHER INFORMATION: Completely Synthetic Amino Acid Sequence

<400> SEQUENCE: 19

Gly Leu Phe Glu Ala Ile Glu Gly Phe Ile Glu Asn Gly Trp Glu Gly
1               5                   10                  15

Met Ile Asp Gly Trp Tyr Gly Tyr Gly Arg Lys Lys Arg Arg Gln Arg
            20                  25                  30

Arg

<210> SEQ ID NO 20
<211> LENGTH: 20
<212> TYPE: PRT
<213> ORGANISM: Artificial Sequence
<220> FEATURE:
<223> OTHER INFORMATION: Completely Synthetic Amino Acid Sequence

<400> SEQUENCE: 20

His Leu His His Leu Leu His His Leu Leu His Leu Leu His His Leu
1               5                   10                  15

Leu His His Leu
            20

<210> SEQ ID NO 21
<211> LENGTH: 20
<212> TYPE: PRT
<213> ORGANISM: Artificial Sequence
<220> FEATURE:
<223> OTHER INFORMATION: Completely Synthetic Amino Acid Sequence

<400> SEQUENCE: 21

His Trp His His Trp Trp His His Trp Trp His Trp Trp His His Trp
1               5                   10                  15

Trp His His Trp
            20

<210> SEQ ID NO 22
```

```
<211> LENGTH: 20
<212> TYPE: PRT
<213> ORGANISM: Artificial Sequence
<220> FEATURE:
<223> OTHER INFORMATION: Completely Synthetic Amino Acid Sequence

<400> SEQUENCE: 22

His Leu His His Leu Leu His His Trp Leu His Leu Leu His His Leu
1               5                   10                  15

Leu His His Leu
            20

<210> SEQ ID NO 23
<211> LENGTH: 20
<212> TYPE: PRT
<213> ORGANISM: Artificial Sequence
<220> FEATURE:
<223> OTHER INFORMATION: Completely Synthetic Amino Acid Sequence

<400> SEQUENCE: 23

His Leu His His Leu Leu His His Leu Leu His Leu Trp His His Leu
1               5                   10                  15

Leu His His Leu
            20

<210> SEQ ID NO 24
<211> LENGTH: 20
<212> TYPE: PRT
<213> ORGANISM: Artificial Sequence
<220> FEATURE:
<223> OTHER INFORMATION: Completely Synthetic Amino Acid Sequence

<400> SEQUENCE: 24

His Leu His His Leu Leu His His Leu Leu His Leu Leu His His Leu
1               5                   10                  15

Leu His His Trp
            20

<210> SEQ ID NO 25
<211> LENGTH: 20
<212> TYPE: PRT
<213> ORGANISM: Artificial Sequence
<220> FEATURE:
<223> OTHER INFORMATION: Completely Synthetic Amino Acid Sequence

<400> SEQUENCE: 25

His His His His His His His His His Leu Leu Leu Leu Leu Leu Leu
1               5                   10                  15

Leu Leu Leu Leu
            20

<210> SEQ ID NO 26
<211> LENGTH: 14
<212> TYPE: PRT
<213> ORGANISM: Artificial Sequence
<220> FEATURE:
<223> OTHER INFORMATION: Completely Synthetic Amino Acid Sequence

<400> SEQUENCE: 26

His His His His His His His Leu Leu Leu Leu Leu Leu Leu
1               5                   10

<210> SEQ ID NO 27
<211> LENGTH: 15
<212> TYPE: PRT
<213> ORGANISM: Artificial Sequence
```

```
<220> FEATURE:
<223> OTHER INFORMATION: Completely Synthetic Amino Acid Sequence

<400> SEQUENCE: 27

Leu Thr Thr Leu Leu Thr Leu Leu Thr Thr Leu Leu Thr Thr Leu
1               5                   10                  15

<210> SEQ ID NO 28
<211> LENGTH: 20
<212> TYPE: PRT
<213> ORGANISM: Artificial Sequence
<220> FEATURE:
<223> OTHER INFORMATION: Completely Synthetic Amino Acid Sequence

<400> SEQUENCE: 28

Lys Leu Leu Lys Leu Leu Lys Leu Trp Leu Lys Leu Leu Lys Leu Leu
1               5                   10                  15

Leu Lys Leu Leu
            20

<210> SEQ ID NO 29
<211> LENGTH: 29
<212> TYPE: PRT
<213> ORGANISM: Artificial Sequence
<220> FEATURE:
<223> OTHER INFORMATION: Completely Synthetic Amino Acid Sequence

<400> SEQUENCE: 29

Leu His Leu Leu His His Leu Leu His His Leu His His Leu Leu His
1               5                   10                  15

His Leu Leu His Leu Leu His His Leu Leu His His Leu
            20                  25

<210> SEQ ID NO 30
<211> LENGTH: 13
<212> TYPE: PRT
<213> ORGANISM: Artificial Sequence
<220> FEATURE:
<223> OTHER INFORMATION: Completely Synthetic Amino Acid Sequence

<400> SEQUENCE: 30

Phe Leu Gly Gly Ile Ile Ser Phe Phe Lys Arg Leu Phe
1               5                   10

<210> SEQ ID NO 31
<211> LENGTH: 13
<212> TYPE: PRT
<213> ORGANISM: Artificial Sequence
<220> FEATURE:
<223> OTHER INFORMATION: Completely Synthetic Amino Acid Sequence

<400> SEQUENCE: 31

Phe Ile Gly Gly Ile Ile Ser Phe Ile Lys Lys Leu Phe
1               5                   10

<210> SEQ ID NO 32
<211> LENGTH: 13
<212> TYPE: PRT
<213> ORGANISM: Artificial Sequence
<220> FEATURE:
<223> OTHER INFORMATION: Completely Synthetic Amino Acid Sequence

<400> SEQUENCE: 32

Phe Ile Gly Gly Ile Ile Ser Leu Ile Lys Lys Leu Phe
1               5                   10
```

```
<210> SEQ ID NO 33
<211> LENGTH: 21
<212> TYPE: PRT
<213> ORGANISM: Artificial Sequence
<220> FEATURE:
<223> OTHER INFORMATION: Completely Synthetic Amino Acid Sequence

<400> SEQUENCE: 33

His Leu Leu His Leu Leu Leu His Leu Trp Leu His Leu Leu His Leu
 1               5                  10                  15

Leu Leu His Leu Leu
            20

<210> SEQ ID NO 34
<211> LENGTH: 27
<212> TYPE: PRT
<213> ORGANISM: Artificial Sequence
<220> FEATURE:
<223> OTHER INFORMATION: Completely Synthetic Amino Acid Sequence

<400> SEQUENCE: 34

Gly Ile Gly Gly Ala Val Leu Lys Val Leu Thr Thr Gly Leu Pro Ala
 1               5                  10                  15

Leu Ile Ser Trp Ile Lys Arg Lys Arg Gln Gln
            20                  25

<210> SEQ ID NO 35
<211> LENGTH: 18
<212> TYPE: PRT
<213> ORGANISM: Artificial Sequence
<220> FEATURE:
<223> OTHER INFORMATION: Completely Synthetic Amino Acid Sequence

<400> SEQUENCE: 35

Arg Gln Ile Lys Ile Trp Phe Gln Asn Arg Arg Met Lys Trp Lys Lys
 1               5                  10                  15

Gly Gly

<210> SEQ ID NO 36
<211> LENGTH: 12
<212> TYPE: PRT
<213> ORGANISM: Artificial Sequence
<220> FEATURE:
<223> OTHER INFORMATION: Completely Synthetic Amino Acid Sequence

<400> SEQUENCE: 36

Arg Lys Lys Arg Arg Gln Arg Arg Pro Pro Gln
 1               5                  10

<210> SEQ ID NO 37
<211> LENGTH: 24
<212> TYPE: PRT
<213> ORGANISM: Artificial Sequence
<220> FEATURE:
<223> OTHER INFORMATION: Completely Synthetic Amino Acid Sequence

<400> SEQUENCE: 37

Gly Ala Leu Phe Leu Gly Trp Leu Gly Ala Ala Gly Ser Thr Met Gly
 1               5                  10                  15

Ala Pro Lys Lys Lys Arg Lys Val
            20

<210> SEQ ID NO 38
<211> LENGTH: 37
<212> TYPE: PRT
<213> ORGANISM: Artificial Sequence
```

```
<220> FEATURE:
<223> OTHER INFORMATION: Completely Synthetic Amino Acid Sequence

<400> SEQUENCE: 38

Gly Gly Gly Ala Arg Lys Lys Ala Ala Lys Ala Ala Arg Lys Lys Ala
1               5                   10                  15

Ala Lys Ala Ala Arg Lys Lys Ala Ala Lys Ala Ala Arg Lys Lys Ala
                20                  25                  30

Ala Lys Ala Ala Lys
            35

<210> SEQ ID NO 39
<211> LENGTH: 27
<212> TYPE: PRT
<213> ORGANISM: Artificial Sequence
<220> FEATURE:
<223> OTHER INFORMATION: Completely Synthetic Amino Acid Sequence

<400> SEQUENCE: 39

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
                20                  25

<210> SEQ ID NO 40
<211> LENGTH: 9
<212> TYPE: PRT
<213> ORGANISM: Artificial Sequence
<220> FEATURE:
<223> OTHER INFORMATION: Completely Synthetic Amino Acid Sequence

<400> SEQUENCE: 40

Arg Arg Arg Arg Arg Arg Arg Arg Arg
1               5

<210> SEQ ID NO 41
<211> LENGTH: 31
<212> TYPE: PRT
<213> ORGANISM: Artificial Sequence
<220> FEATURE:
<223> OTHER INFORMATION: Completely Synthetic Amino Acid Sequence

<400> SEQUENCE: 41

Trp Glu Ala Lys Leu Ala Lys Ala Leu Ala Lys Ala Leu Ala Lys His
1               5                   10                  15

Ile Leu Ala Lys Ala Leu Ala Lys Ala Leu Lys Ala Cys Glu Ala
                20                  25                  30

<210> SEQ ID NO 42
<211> LENGTH: 32
<212> TYPE: PRT
<213> ORGANISM: Artificial Sequence
<220> FEATURE:
<223> OTHER INFORMATION: Completely Synthetic Amino Acid Sequence

<400> SEQUENCE: 42

Trp Glu Ala Ala Leu Ala Glu Ala Leu Ala Glu Ala Leu Ala Glu His
1               5                   10                  15

Leu Ala Glu Ala Leu Ala Glu Ala Glu Ala Leu Glu Ala Leu Ala Ala
                20                  25                  30

<210> SEQ ID NO 43
<211> LENGTH: 12
<212> TYPE: PRT
<213> ORGANISM: Artificial Sequence
```

```
<220> FEATURE:
<223> OTHER INFORMATION: Completely Synthetic Amino Acid Sequence
<221> NAME/KEY: VARIANT
<222> LOCATION: 2, 4, 6, 8, 10, 12
<223> OTHER INFORMATION: Xaa = norleucine
<221> NAME/KEY: CARBOHYD
<222> LOCATION: (1)...(1)
<223> OTHER INFORMATION: NHC12H25

<400> SEQUENCE: 43

Asp Xaa Lys Xaa Lys Xaa His Xaa Lys Xaa His Xaa
 1               5                  10

<210> SEQ ID NO 44
<211> LENGTH: 21
<212> TYPE: PRT
<213> ORGANISM: Artificial Sequence
<220> FEATURE:
<223> OTHER INFORMATION: Completely Synthetic Amino Acid Sequence

<400> SEQUENCE: 44

Lys Leu Leu Lys Leu Leu Leu Lys Leu Trp Leu Lys Leu Leu Lys Leu
 1               5                  10                  15

Leu Leu Lys Leu Leu
            20

<210> SEQ ID NO 45
<211> LENGTH: 23
<212> TYPE: PRT
<213> ORGANISM: Artificial Sequence
<220> FEATURE:
<223> OTHER INFORMATION: Completely Synthetic Amino Acid Sequence

<400> SEQUENCE: 45

Gly Leu Phe Glu Ala Ile Ala Gly Phe Ile Glu Asn Gly Trp Glu Gly
 1               5                  10                  15

Met Ile Asp Gly Trp Tyr Gly
            20

<210> SEQ ID NO 46
<211> LENGTH: 24
<212> TYPE: PRT
<213> ORGANISM: Artificial Sequence
<220> FEATURE:
<223> OTHER INFORMATION: Completely Synthetic Amino Acid Sequence

<400> SEQUENCE: 46

Gly Leu Phe His Ala Ile Ala Ala His Phe Ile His Gly Gly Trp His
 1               5                  10                  15

Gly Leu Ile His Gly Trp Tyr Gly
            20

<210> SEQ ID NO 47
<211> LENGTH: 23
<212> TYPE: PRT
<213> ORGANISM: Artificial Sequence
<220> FEATURE:
<223> OTHER INFORMATION: Completely Synthetic Amino Acid Sequence

<400> SEQUENCE: 47

Gly Leu Phe Glu Ala Ile Ala Glu Phe Ile Glu Gly Gly Trp Glu Gly
 1               5                  10                  15

Leu Ile Glu Gly Trp Tyr Gly
            20

<210> SEQ ID NO 48
```

```
<211> LENGTH: 23
<212> TYPE: PRT
<213> ORGANISM: Artificial Sequence
<220> FEATURE:
<223> OTHER INFORMATION: Completely Synthetic Amino Acid Sequence

<400> SEQUENCE: 48

Gly Leu Phe Glu Ala Ile Glu Gly Phe Ile Glu Asn Gly Trp Glu Gly
1               5                   10                  15

Met Ile Asp Gly Trp Tyr Gly
            20

<210> SEQ ID NO 49
<211> LENGTH: 23
<212> TYPE: PRT
<213> ORGANISM: Artificial Sequence
<220> FEATURE:
<223> OTHER INFORMATION: Completely Synthetic Amino Acid Sequence

<400> SEQUENCE: 49

Gly Leu Phe Lys Ala Ile Ala Lys Phe Ile Lys Gly Gly Trp Lys Gly
1               5                   10                  15

Leu Ile Lys Gly Trp Tyr Gly
            20

<210> SEQ ID NO 50
<211> LENGTH: 33
<212> TYPE: PRT
<213> ORGANISM: Artificial Sequence
<220> FEATURE:
<223> OTHER INFORMATION: Completely Synthetic Amino Acid Sequence

<400> SEQUENCE: 50

Gly Leu Phe Glu Ala Ile Ala Gly Phe Ile Glu Asn Gly Trp Glu Gly
1               5                   10                  15

Met Ile Asp Gly Trp Tyr Gly Tyr Gly Arg Lys Lys Arg Gln Arg
            20                  25                  30

Arg

<210> SEQ ID NO 51
<211> LENGTH: 41
<212> TYPE: PRT
<213> ORGANISM: Artificial Sequence
<220> FEATURE:
<223> OTHER INFORMATION: Completely Synthetic Amino Acid Sequence

<400> SEQUENCE: 51

Gly Leu Phe Glu Ala Ile Ala Gly Phe Ile Glu Asn Gly Trp Glu Gly
1               5                   10                  15

Met Ile Asp Gly Trp Tyr Gly Arg Gln Ile Lys Ile Trp Phe Gln Asn
            20                  25                  30

Arg Arg Met Lys Trp Lys Lys Gly Gly
        35                  40

<210> SEQ ID NO 52
<211> LENGTH: 34
<212> TYPE: PRT
<213> ORGANISM: Artificial Sequence
<220> FEATURE:
<223> OTHER INFORMATION: Completely Synthetic Amino Acid Sequence

<400> SEQUENCE: 52

Gly Leu Phe His Ala Ile Ala Ala His Phe Ile His Gly Gly Trp His
1               5                   10                  15
```

```
Gly Leu Ile His Gly Trp Tyr Gly Tyr Gly Arg Lys Lys Arg Arg Gln
            20                  25                  30

Arg Arg

<210> SEQ ID NO 53
<211> LENGTH: 33
<212> TYPE: PRT
<213> ORGANISM: Artificial Sequence
<220> FEATURE:
<223> OTHER INFORMATION: Completely Synthetic Amino Acid Sequence

<400> SEQUENCE: 53

Gly Leu Phe Glu Ala Ile Ala Glu Phe Ile Glu Gly Gly Trp Glu Gly
1               5                   10                  15

Leu Ile Glu Gly Trp Tyr Gly Tyr Gly Arg Lys Lys Arg Arg Gln Arg
            20                  25                  30

Arg

<210> SEQ ID NO 54
<211> LENGTH: 33
<212> TYPE: PRT
<213> ORGANISM: Artificial Sequence
<220> FEATURE:
<223> OTHER INFORMATION: Completely Synthetic Amino Acid Sequence

<400> SEQUENCE: 54

Gly Leu Phe Glu Ala Ile Glu Gly Phe Ile Glu Asn Gly Trp Glu Gly
1               5                   10                  15

Met Ile Asp Gly Trp Tyr Gly Tyr Gly Arg Lys Lys Arg Arg Gln Arg
            20                  25                  30

Arg

<210> SEQ ID NO 55
<211> LENGTH: 33
<212> TYPE: PRT
<213> ORGANISM: Artificial Sequence
<220> FEATURE:
<223> OTHER INFORMATION: Completely Synthetic Amino Acid Sequence

<400> SEQUENCE: 55

Gly Leu Phe Lys Ala Ile Ala Lys Phe Ile Lys Gly Gly Trp Lys Gly
1               5                   10                  15

Leu Ile Lys Gly Trp Tyr Gly Tyr Gly Arg Lys Lys Arg Arg Gln Arg
            20                  25                  30

Arg

<210> SEQ ID NO 56
<211> LENGTH: 33
<212> TYPE: PRT
<213> ORGANISM: Artificial Sequence
<220> FEATURE:
<223> OTHER INFORMATION: Completely Synthetic Amino Acid Sequence

<400> SEQUENCE: 56

Gly Phe Phe Ala Leu Ile Pro Lys Ile Ile Ser Ser Pro Leu Phe Lys
1               5                   10                  15

Thr Leu Leu Ser Ala Val Gly Ser Ala Leu Ser Ser Ser Gly Glu Gln
            20                  25                  30

Glu

<210> SEQ ID NO 57
<211> LENGTH: 44
```

```
<212> TYPE: PRT
<213> ORGANISM: Artificial Sequence
<220> FEATURE:
<223> OTHER INFORMATION: Completely Synthetic Amino Acid Sequence

<400> SEQUENCE: 57

Leu His Leu Leu His His Leu Leu His His Leu His His Leu Leu His
 1               5                  10                  15

His Leu Leu His Leu Leu His His Leu Leu His His Leu Gly Gly Gly
                20                  25                  30

Arg Lys Lys Arg Arg Gln Arg Arg Arg Pro Pro Gln
            35                  40

<210> SEQ ID NO 58
<211> LENGTH: 44
<212> TYPE: PRT
<213> ORGANISM: Artificial Sequence
<220> FEATURE:
<223> OTHER INFORMATION: Completely Synthetic Amino Acid Sequence

<400> SEQUENCE: 58

Arg Lys Lys Arg Arg Gln Arg Arg Arg Pro Pro Gln Gly Gly Gly Leu
 1               5                  10                  15

His Leu Leu His His Leu Leu His His Leu His His Leu Leu His His
                20                  25                  30

Leu Leu His Leu Leu His His Leu Leu His His Leu
            35                  40

<210> SEQ ID NO 59
<211> LENGTH: 22
<212> TYPE: PRT
<213> ORGANISM: Artificial Sequence
<220> FEATURE:
<223> OTHER INFORMATION: Completely Synthetic Amino Acid Sequence

<400> SEQUENCE: 59

Leu Ile Arg Leu Trp Ser His Ile His Ile Trp Phe Gln Trp Arg Arg
 1               5                  10                  15

Leu Lys Trp Lys Lys Lys
            20
```

What is claimed is:

1. A modular composition comprising 1) an siRNA; 2) one or more linkers, which may be the same or different, selected from the following linkers, wherein the linkers are attached to the siRNA at any 3' and/or 5' end;

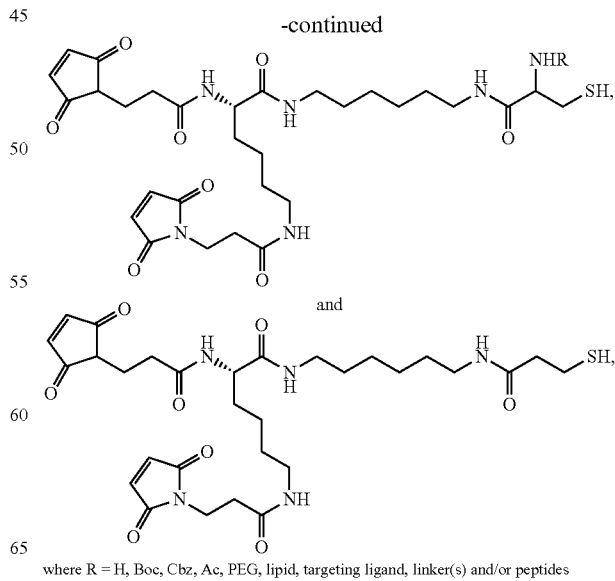

where R = H, Boc, Cbz, Ac, PEG, lipid, targeting ligand, linker(s) and/or peptides and n=0 to 750;

and 3) one or more peptides, which may be the same or different, selected from SEQ ID NOs 1-59, wherein the peptides are attached to the linkers.

2. The modular composition of claim 1 wherein the linkers are attached to the guide strand of the siRNA at the 3' and/or 5' end.

3. The modular composition of claim 1 wherein the linkers are attached to the passenger strand of the siRNA at the 3' and/or 5' end.

4. A modular composition comprising 1) an siRNA; 2) one or more linkers, which may be the same or different, selected from the following linkers, wherein the linkers are attached to the siRNA at any 3' and/or 5' end;

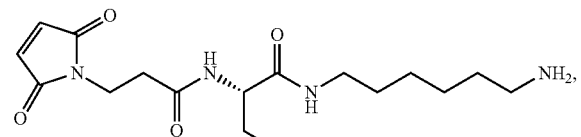

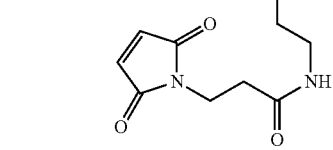

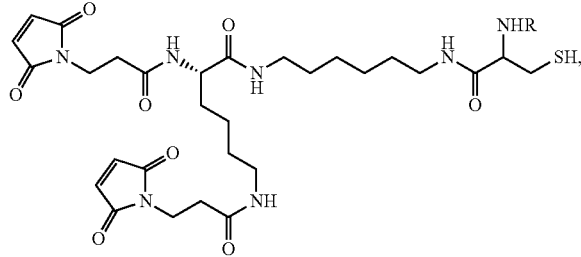

-continued
and

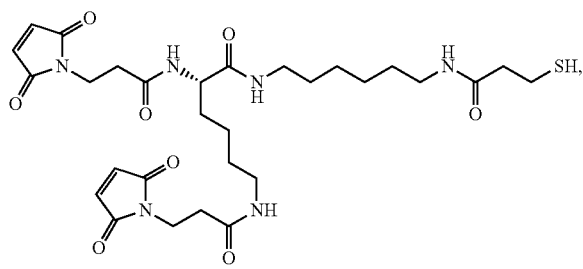

where R = H, Boc, Cbz, Ac, PEG, lipid, targeting ligand, linker(s) and/or peptides.

and n=0 to 750;

and 3) one or more peptides, which may be the same or different, selected from SEQ ID NOs: 28, 29, 33, 35, 36, 40, 50, 51, 52, 53, 54, 55, 56, 57, 58, and 59, wherein the peptides are attached to the linkers.

5. The modular composition of claim 4 wherein the linkers are attached to the guide strand of the siRNA at the 3' and/or 5' end.

6. The modular composition of claim 4 wherein the linkers are attached to the passenger strand of the siRNA at the 3' and/or 5' end.

* * * * *